United States Patent [19]

Deeley et al.

[11] Patent Number: 5,766,880
[45] Date of Patent: Jun. 16, 1998

[54] ISOLATED NUCLEIC ACID MOLECULES ENCODING MULTIDRUG RESISTANCE PROTEINS

[75] Inventors: Roger G. Deeley; Susan P.C. Cole, both of Kingston, Canada

[73] Assignee: Queen's University at Kingston, Kingston, Canada

[21] Appl. No.: 463,092

[22] Filed: Jun. 5, 1995

Related U.S. Application Data

[63] Continuation-in-part of Ser. No. 407,207, Mar. 20, 1995, which is a continuation-in-part of Ser. No. 141,893, Oct. 26, 1993, Pat. No. 5,489,519, which is a continuation-in-part of Ser. No. 29,340, Mar. 8, 1993, abandoned, which is a continuation-in-part of Ser. No. 966,923, Oct. 27, 1992, abandoned.

[51] Int. Cl.$^6$ .................... C12P 21/00; C07H 21/04; C12N 15/63; C12N 5/08
[52] U.S. Cl. .................... 435/69.1; 435/243; 435/320.1; 435/366; 435/372; 536/23.5; 536/24.31
[58] Field of Search .................... 435/69.1, 243, 435/320.1, 366, 372; 514/44; 536/23.1, 23.5, 24.31

[56] References Cited

U.S. PATENT DOCUMENTS

| | | | |
|---|---|---|---|
| 4,912,039 | 3/1990 | Riordan | 435/69.1 |
| 5,166,059 | 11/1992 | Pastan et al. | 435/69.7 |
| 5,198,344 | 3/1993 | Croop et al. | 435/69.1 |
| 5,206,352 | 4/1993 | Roninson et al. | 536/24.31 |
| 5,489,519 | 2/1996 | Deeley et al. | 435/69.1 |

OTHER PUBLICATIONS

Abbaszadegan, M.R. et al. (1994)"Analysis of Multidrug Resistance-associated Protein (MRP) Messenger RNA in Normal and Malignant Hematopoietic Cells" *Cancer Research* 54: 4676–4679.

Almquist, K.C. et al. (1995) "Characterization of the $M_T$ 190.000 Multidrug Resistance Protein (MRP) in Drug-Selected and Transfected Human Tumor Cells" *Cancer Research* 55: 102–110.

Barrand, M.A. et al. (1992) "Chemosensitisation and Drug Accumulation Effects of Cyclosporin A, PSC-833 and Verapamil in Human MDR Large Cell Lung Cancer Cells Expressing a 190K Membrane Protein Distinct from P–glycoprotein" *Eur. J. Cancer* 29A(3):408–415.

Bordow, S.B. et al. (1994) "Expression of the Multidrug Resistance-associated Protein (MRP) Gene Correlates with Amplification and Overexpression of the N–myc Oncogene in Childhood Neuroblastoma" *Cancer Research* 54:5036–5040.

Brock, I. et al. (1995) "Sequential Coexpression of the Multidrug Resistance Genes MRP and mdr 1 and Their Products in VP–16 (Etoposide)–selected H69 Small Cell Lung Cancer Cells" *Cancer Research* 55: 459–462.

Burger, H. et al. (1994) "Expression of the Multidrug Resistance–Associated Protein (MRP) in Acute and Chronic Leukemias" *Leukemia* 8(6):990–997.

Chen, C-J. et al. (1986) "Internal Duplication and Homology with Bacterial Transport Proteins in the mdr1 (P–Glycoprotein) Gene from Multidrug–Resistant Human Cells" *Cell* 47:381–389.

Cole, S.P.C. et al. (1993) "A Novel ATP–Binding Cassette Transporter Gene Overexpressed in Multidrug–Resistant Human Lung Tumor Cells" *Proc. Am. Assoc. Cancer. Res.* 34:579 (Abstract).

Cole, S.P.C. et al. (1989) "Effect of Calcium Antagonists on the Chemosensitivity of Two Multidrug–Resistant Human Tumor Cell Lines Which do not Overexpress P–glycoprotein" *Br. J. Cancer* 59:42–46.

Cole, S.P.C. et al. (1992) "Elevated Expression of Annexin II (Lipocortin II, p. 36) in a Multidrug Resistant Small Cell Lung Cancer Cell Line" *J. Cancer* 65:498–502.

Cole, S.P.C. et al. (1993) "MRP: A Novel ATP–Binding Cassette Transporter Gene Isolated From a Multidrug Resistant Small Cell Lung Cancer Cell Line" *Third International LASLC Workshop on Lung Tumor and Differentiation Antigens* (Abstract).

Cole, S.P.C. and R.G. Deeley (1993) "Multidrug Resistance–Associated Protein: Sequence Correction" *Science* 260: 879.

Cole, S.P.C. et al. (1992) "Overexpression of a Transporter Gene in a Multidrug–Resistant Human Lung Cancer Cell Line" *Science* 258:1650–1654.

Cole, S.P.C. (1990) "Patterns of Cross–Resistance in a Multidrug–Resistant Small–Cell Lung Carcinoma Cell Line" *Cancer Chemother.Pharmacol.* 26:250–256.

Cole, S.P.C. et al. (1994) "Pharmacological Characterization of Multidrug Resistant MRP–transfected Human Tumor Cells" *Cancer Research* 54:5902–5910.

Cole, S.P.C. (1991) "The 1991 Merck Frosst Award. Multidrug Resistance in Small Cell Lung Cancer" *Can. J. Physiol. Pharmacol.* 70:313–329.

DelaFlor–Weiss, E. et al. (1992) "Transfer and Expression of the Human Multidrug Resistance Gene in Mouse Erythroleukemia Cells" *Blood* 80(12):3106–3111.

Flens, M.J. et al. (1994) "Immunochemical Detection of the Multidrug Resistance–associated Protein MRP in Human Multidrug–resistant Tumor Cells by Monoclonal Antibodies" *Cancer Research* 54: 4557–4563.

Fojo, A.T. et al. (1985) "Amplification of DNA Sequences in Human Multidrug–Resistant KB Carcinoma Cells" *Proc. Natl. Acad. Sci. USA* 82:7661–7665.

(List continued on next page.)

*Primary Examiner*—George C. Elliott
*Assistant Examiner*—Robert Schwarteman
*Attorney, Agent, or Firm*—Carol Miernicki Steeg; Catherine J. Kara; Giulio A. DeConti, Jr.

[57] ABSTRACT

A novel protein associated with multidrug resistance in living cells and capable of conferring multidrug resistance on a cell is disclosed. Nucleic acids encoding the novel multidrug resistance protein are also disclosed. Transformant cell lines which express the nucleic acid encoding the novel protein are also disclosed. Antibodies which bind the novel multidrug resistance protein are also disclosed. Diagnostic and treatment methods using the novel proteins, nucleic acids, antibodies and cell lines of the invention are also encompassed by the invention.

16 Claims, 21 Drawing Sheets

OTHER PUBLICATIONS

Grant, C.E. et al. (1994) "Overexpression of Multidrug Resistance–Associated Protein (MRP) Increases Resistance to Natural Product Drugs" *Cancer Research* 54: 357–361.

Gros, P. et al. (1986) "Isolation and Characterization of DNA Sequences Amplified in Multidrug–Resistant Hamster Cells" *Proc. Natl. Acad. Sci. USA* 83:337–341.

Higgins, C.F. (1992) "ABC Transporters: From Microorganisms to Man" *Annu. Rev. Cell Biol.* 8:67–113.

Hipfner, D.R. (1994) "Detection of the $M_r$ 190.000 Multidrug Resistance Protein, MRP, with Monoclonal Antibodies" *Cancer Research* 54: 5788–5792.

Hyde, S.C. et al. (1990) "Structural Model of ATP–Binding Protein Associated With Cystic Fibrosis, Multidrug Resistance and Bacterial Transport" (1990) *Nature* 346:362–365.

Jeditschky, G. et al. (1994) "ATP–Dependent Transport of Glutathione S–Conjugates by the Multidrug Resistance–Associated Protein" *Cancer Research* 54: 4833–4836.

Jirsch, R.G. et al. (1993) "Inwardly Rectifying $K^+$ Channels and Volume–regulated Anion Channels in Multidrug–resistant Small Cell Lung Cancer Cells" *Cancer Research* 53:1–5.

Krebes, K.A. et al. (1993) "Peripheral Blood Mononuclear Cells Express Antigens Associated with Multidrug Resistance in a Small Cell Lung Cancer Cell Line" *Anticancer Research* 13: 317–322.

Krishnamachary, N. and M.S. Center (1993) "The MRP Gene Associated with a Non–P glycoprotein Multidrug Resistance Encodes a 190–kDa Membrane Bound Glycoprotein" *Cancer Research* 55: 3658–3661.

Kruh, G.D. et al. (1994) "Expression Complementary DNA Library Transfer Establishes mrp as a Multidrug Resistance Gene" *Cancer Research* 54:1649–1652.

Kuss, B.J. et al. (1994) "Deletion of Gene for Multidrug Resistance in Acute Myeloid Leukaemia with Inversion in Chromosome 16: Prognostic Implications" *The Lancet* 343:1531–1534.

Leier, Inka et al. (1994) "The MRP Gene Encodes an ATP–dependent Export Pump for Leukotriene $C_4$ and Structurally Related Conjugates" *The Journal of Biological Chemistry* 269(45): 27807–27810.

Marquardt, D. et al. (1990) "Mechanisms of Multidrug Resistance in HL60 Cells: Detection of Resistance–Associated Proteins with Antibodies Against Synthetic Peptides That Correspond to the Deduced Sequence of P–Glycoprotein" *Cancer Res.* 50:1426–1430.

Mirski, S.E.L. et al. (1987) "Multidrug Resistance in a Human Small Cell Lung Cancer Cell Line Selected in Adriamycin" *Cancer Research* 47:2594–2598.

Ouellette, M. et al. (1990) "The Amplified H Circle of Methotrexate–Resistant Leishmania Tarentolae Contains a Novel P–glycoprotein Gene" *EMBO J.* 9(4):1027–1033.

Papadopoulou, B. et al. (1994) "Contribution of the *Leishmania* P–glycoprotein–related Gene ltpgpA to Oxyanion Resistance" *Journal of Biological Chemistry* 269(16): 11980–11986.

Podda, S. et al. (1992) "Transfer and Expression of the Human Multiple Drug Resistance Gene into Live Mice" *Proc. Natl. Acad. Sci. USA* 89:9676–9680.

Riordan, J.R. et al. (1985) "Amplification of P–glycoprotein Genes in Multidrug–Resistant Mammalian Cell Lines" *Nature* 316:817–819;.

Rivoltini, L. et al. (1990) "Modulation of Multidrug Resistance By Verapamil of mdr1 Anti–Sense Oligodeoxynucleotide Does Not Change The High Susceptibility to Lymphokine–Activated Killers in mdr–Resistant Human Carcinoma (LoVo) Line" *Int. J. Cancer* 46:727–732.

Roninson, I.B. et al. (1984) "Amplification of Specific DNA Sequences Correlates with Multi–drug Resistance in Chinese Hamster Cells" *Nature* 309:626–628.

Roninson, I.B. et al. (1986) "Isolation of Human mdr DNA Sequences Amplified in Multidrug–Resistant KB Carcinoma Cells" *Proc. Natl. Acad. Sci. USA* 83:4538–4542.

Slovak, M.L. et al. (1993) "Localization of a Novel Multidrug Resistance–associated Gene in the HT1080/DR4 and H69AR Human Tumor Cell Lines" *Cancer Research* 53: 3221–3225.

Sumizawa, T. et al. (1994) "Non–P–Glycoprotein–Mediated Multidrug–Resistant Human KB Cells Selected in Medium Containing Adriamycin, Cepharanthine, and Mezerein" *Somatic Cell and Molecular Genetics* 20(5): 423–435.

Sugawara, I. et al. (1994) "Expression of Multidrug Resistance–associated Protein (MRP) in Anaplastic Carcinoma of the Thyroid" *Cancer Letters* 82: 185–188.

Szczypka, M.S. (1994) "A Yeast Metal Resistant Protein Similar to Human Cystic Fibrosis Transmembrane Conductance Regulator (CFTR) and Multidrug Resistance–associated Protein" *Journal of Biological Chemistry* 269(36): 22853–22857.

Ueda, K. et al. (1986) "The mdr1 Gene, Responsible For Multidrug–Resistance, Codes For P–Glycoprotein" *Biochem. and Biophys. Res. Comm.* 141(3):956–962.

Zaman, G.J.R. et al. (1994) "The Human Multidrug Resistance–associated Protein MRP is a Plasma Membrane Drug–efflux Pump" *Proc. Natl. Acad. Sci USA* 91: 8822–8826.

Zaman et al. (1994) Proc. Natl. Acad. Sci. USA 91:8822–8826. Sep. 1994.

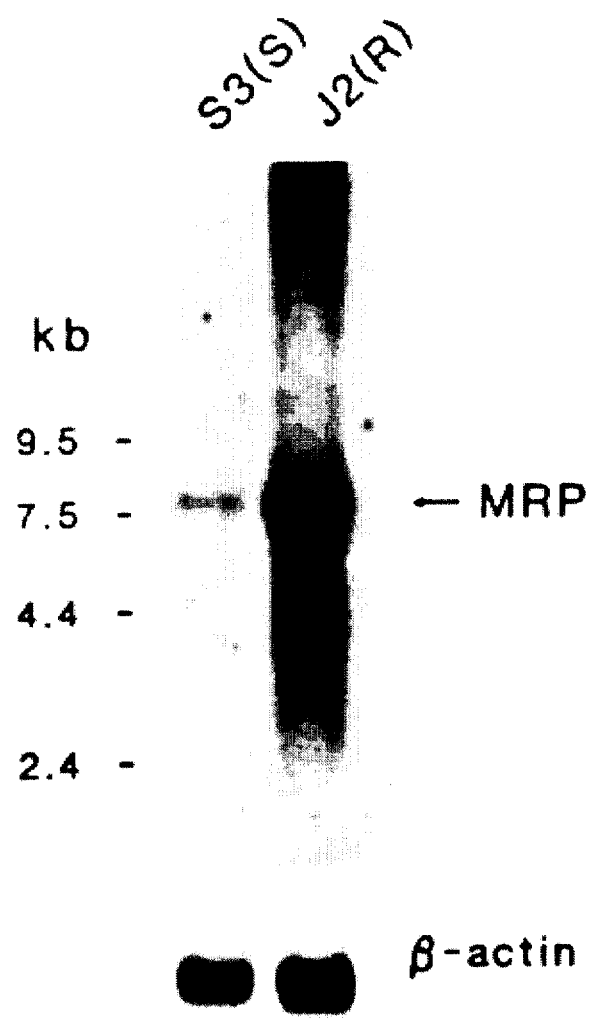
FIG. IC

| | | |
|---|---|---|
| Hum/MRP | MALRGFCSADGSDPLWDWNVTWNTSNPDFTKCFQNTV | 37 |
| Hum/MRP | LVWVPCFYLWACFPFYFLYLSRHDRGYIQMTPLNKTK | 74 |
| | : | |
| Lei/PgpA | MVDNGHVT | 8 |
| Hum/MRP | TALGFLLWIVCWADLFY-SFWERSRGIFLAPVFLVSP | 110 |
| | :. : .: : .. : : .. : | |
| Lei/PgpA | IAMADLGTVVEIAQVRCQQEAQRKFAEQLDELWGGEP | 45 |
| Hum/MRP | TLLGITTLLATFLIQLERRKGVQSSGIMLTFWLVALV | 147 |
| | : .. :: :. . | |
| Lei/PgpA | AYTPTVEDQASWFQQL-----------YYGWIGDYI | 70 |
| Hum/MRP | CALAILRSKIMTALKEDAQVDLFRDITFYVYFSLLLI | 184 |
| | . : : : :. . : | |
| Lei/PgpA | YKAAA--GNITEA---DLPPPTRSTRTYHIGRKLSRQ | 102 |
| Hum/MRP | QLVLSCFSDRSPLFSETIHDPNPCPESSASFLSRITF | 221 |
| | : : . : : . | |
| Lei/PgpA | AHADIDASRRWQGYIGCEVVYKSCAEAKG------VL | 133 |
| Hum/MRP | WWITGLIVRGYRQPLEGSDLWSLNKEDTSEQVVPVLV | 258 |
| | .:. : : : : . | |
| Lei/PgpA | RWVGHLQQSDYPRSLVAGVEWRMP-----------P | 158 |
| Hum/MRP | KNWKKECAKTRKQPVKVVYSSKDPAQPKESSKVDANE | 295 |
| | . .. : :: . : | |
| Lei/PgpA | RHRRLAVLGSAAALHNGVVHGERLFWPHEDNYLCSCE | 195 |
| Hum/MRP | EVEALIVKS------PQKEWNPSLFKVLYKTFGPYFL | 326 |
| | :: : ::: : : :.. :.: | |
| Lei/PgpA | PVEQLYVKSKYNLIPPRPPPSPDLLRTLFKVHWYHVW | 232 |

Fig. 3A-1

```
Hum/MRP   MSFFFKAIHDLMMFSGPQILKLLIKFVNDTKAPDWQG      363
            .  :  :.    .    :  .:     ..:..:    :    :
Lei/PgpA  AQILPKLLSDVTALMLPVLLEYFVKYLNADNATWGWG      269

Hum/MRP   YFYTVLLFVTACLQTLVLHQYFHICFVSGMRIKTAVI      400
            .  .:.   .:       :  : ::              :
Lei/PgpA  LGLALTIFLTNVIQSCSAHKYDHISIRTAALFETSSM      306

Hum/MRP   GAVYRKALVITNSA--RKSSTVGEIVNLMSVDAQRFM      435
            ..  :  . .       :      :: : :.    :
Lei/PgpA  ALLFEKCFTVSRRSLQRPDMSVGRIMNMVGNDVDNIG      343

Hum/MRP   DLATYINMIWSAPLQVILALYLLWLNLGPSVLAGVAV      472
            :  :.     :::::::..: : ::    .:    .  : ::
Lei/PgpA  SLNWYVMYFWSAPLQLVLCLLLLIRLVGWLRVPGMAV      380

Hum/MRP   MVLMVPVNAVMAMKTKTYQVAHMKSKDNRIKLMNEIL      509
            .   . .:. ::                 : :::   :: .:
Lei/PgpA  LFVTLPLQAVISKHVQDVSERMASVVDLRIKRTNELL      417

Hum/MRP   NGIKVLKLYAWELAFKDKVLAIRQEELKVLKKSAYLS      546
            :......:.   ::   :    ..    :   ::. :.
Lei/PgpA  SGVRIVKFMGWEPVFLARIQDARSRELRCLRDVHVAN      454

Hum/MRP   AVGTFTWVCTPFLVALCTFAVYVTIDENNILDAQTAF      583
            :      ::  ::     .   .:          .:        :
Lei/PgpA  VFFMFVNDATPTLVIAVVFILYHV--SGKVLKPEVVF      489

Hum/MRP   VSLALFNILRFPLNILPMVISSIVQASVSLKRLRIFL      620
            .:.:.  .:     .  .:  .::::.:   ::   ::.   :.
Lei/PgpA  PTIALLNTMRVSFFMIPIIISSILQCFVSAKRVTAFI      526

Hum/MRP   SHEE---------------LEPDSIE-------      631
            .                        : :
Lei/PgpA  ECPDTHSQVQDIASIDVPDAAAIFKGASIHTYLPVKL      563
```

Fig. 3A-2

```
Hum/MRP   ------------------RRPVKD---------GGGT           641
          ::  :  .
Lei/PgpA  PRCKSRLTAMQRSTLWFRRRGVPETEWYEVDSPDASA            600

Hum/MRP   NSITVRNATFTWARSDPPT------------------           660
          :.  :    :
Lei/PgpA  SSLAVHSTTVHMGSTQTVITDSDGAAGEDEKGEVEEG            637

Hum/MRP   -------------LNGITFSIPEGALVAVVGQVGCGKL           685
                       :  . .  ::  :   :.:   :  ::
Lei/PgpA  DREYYQLVSKELLRNVSLTIPKGKLTMVIGSTGSGKS            674
                                         A

Hum/MRP   SLLSALLAEMDKVEGHVAIKGSVAYVPQQAWIQNDSL           722
          ::  ::. :        :  .     :.::::::::: :   :
Lei/PgpA  TLLGALMGEYSVESGELWAERSIAYVPQQAWIMNATL           711

Hum/MRP   RENILFGCQLEEPYYRSVIQACALLPDLEILPSGDRT           759
          :  ::::         ::   ::   ::    .  :     :
Lei/PgpA  RGNILFFDEERAEDLQDVIRCCQLEADLAQFCGGLDT           748

Hum/MRP   EIGEKGVNLSGGQKQRVSLARAVYSNADIYLFDDPLS           796
          ::::  :::::::::  :::::::::: :  :.::.:::::
Lei/PgpA  EIGEMGVNLSGGQKARVSLARAVYANRDVYLLDDPLS           785
              C                       B

Hum/MRP   AVDAHVGKHIFENVIGPKGMLKNKTRILVTHSMSYLP           833
          :.::::::   :    ::      :  :.  :::..:   ::   ::
Lei/PgpA  ALDAHVGQRIVQDVI--LGRLRGKTRVLATHQIHLLP           820

Hum/MRP   QVDVIIVMSGGKISEMGSYQELLARDGAFAEFLRTYA           870
          :  :.:. : :    :  :      . :   :.  :  ::
Lei/PgpA  LADYIVVLQHGSIVFAGDFAAFSA--TALEETLR---           852

Hum/MRP   STEQEQDAEENGVTGVSGPGKEAKQMENGMLVTDSAG           907
          :    :       :        .           . :.::
Lei/PgpA  -------GELKGSKDVESCSSD---------VDTESAT           874
```

Fig. 3A-3

| | | |
|---|---|---|
| Hum/MRP | KQLQRQLSSSSSYSGDISRHHNSTAELQKAEAKKEET | 944 |
| Lei/PgpA | AETAPYVAKAKGLNAE---QETSLAGGEDPLRSDVEA | 908 |
| | | |
| Hum/MRP | WKLMEADKAQTGQVKLSVYWDYMKAIGLFISFLSIF- | 980 |
| Lei/PgpA | GRLMTTEEKATGKVPWSTYVAYLKSCGGLEAWGCLLA | 945 |
| | | |
| Hum/MRP | -LFMCNHVSALASNYWLSLWTDDPIVNGTQEHTKVRL | 1016 |
| Lei/PgpA | TFALTECVTA-ASSVWLSIWSTGSLMWSADTY<u>LYVYL</u> | 981 |
| | | |
| Hum/MRP | SVYGALGISQGIAVFGYSMAVSIGGILASRCLHVDLL | 1053 |
| Lei/PgpA | <u>FIVFLEIFGS</u>PLRFFLCYYLIRIG----SRNMHRDLL | 1014 |
| | | |
| Hum/MRP | HSILRSPMSFFERTPSGNLVNRFSKELDTVDSMIPEV | 1090 |
| Lei/PgpA | ESIGVARMSFFDTTPVGRVLNRFTKDMSILDNTLNDG | 1051 |
| | | |
| Hum/MRP | IKMFMGSLFNVIGACIVILLATPIAAIIPPLGLIYF | 1127 |
| Lei/PgpA | YLYLLEYFFSMCS<u>TVIIMVVQPFVLVAIV</u>PCVYSYY | 1088 |
| | | |
| Hum/MRP | FVQRFYVASSRQLKRLESVSRSPVYSHFNETLLGVSV | 1164 |
| Lei/PgpA | KLMQVYNASNRETRRIKSIAHSPVFTLLEESLQGQRT | 1125 |
| | | |
| Hum/MRP | IRAFEEQERFIHQSDLKVDENQKAYYPSIVANRWLAV | 1201 |
| Lei/PgpA | IATYGKLHLVLQEALGRLDVVYSALYMQNVSNRWLGV | 1162 |
| | | |
| Hum/MRP | RLECVGNCIVLFAALFAVISR----HSLSAGLVGLSV | 1234 |
| Lei/PgpA | RLE<u>FLSCVVTFMVAFIGVI</u>GKMEGASSQNIGLISLSL | 1199 |

Fig. 3A-4

```
Hum/MRP   SYSLQVTTYLNWLVRMSSEMETNIVAVERLKEYS-ET      1270
          :. .:   ::::::    : :    :::.   :    :
Lei/PgpA  TMSMTLTETLNWLVRQVAMVEANMNSVERVLHYTQEV      1236

Hum/MRP   EKE-----APWQIQETRPPSSWP--------------      1288
          : :           :    :   :   .
Lei/PgpA  EHEHVPEMGELVAQLVRSESGRGANVTETVVIESAGA      1273

Hum/MRP   --------QVGRVEFRNYCLRYREDLDFVLRHINVTI      1317
              :  :  . .   .::::  :  .:::  .       :
Lei/PgpA  ASSALHPVQAGSLVLEGVQMRYREGLPLVLRGVSFQI      1310

Hum/MRP   NGGEKVGIVGRTGAGKSSLTLGLFRINESAEGEIIID      1354
          ::::::::::: :::  :  :  :    :    : : .
Lei/PgpA  APREKVGIVGRTGSGKSTLLLTFMRMVEVCGGVIHVN      1347
                       A

Hum/MRP   GINIAKIGLHDLRFKITIIPQDPVLFSGSLRMNLDPF      1391
          :      ::  .::         :::::::: :  .: :.:::
Lei/PgpA  GREMSAYGLRELRRHFSMIPQDPVLFDGTVRQNVDPF      1384

Hum/MRP   SQYSDEEVWTSLELAHLKDFVSALPDKLDHECAEGGE      1428
            :  :::   :::    :.. :       . .:   :::
Lei/PgpA  LEASSAEVWAALELVGLRERVASESEGIDSRVLEGGS      1421

Hum/MRP   NLSVGQRQLVCLARALLRKTK-ILVLDEATAAVDLET      1464
          : :::::::.:.::::::..    ...:::::  .:
Lei/PgpA  NYSVGQRQLMCMARALLKRGSGFILMDEATANIDPAL      1458
             C                     B

Hum/MRP   DDLIQSTIRTQFEDCTVLTIAHRLNTIMDYTRVIVLD      1501
          :   ::  :.    :    .::.:::::::  :.    :  ..::.:
Lei/PgpA  DRQIQATVMSAFSAYTVITIAHRLHTVAQYDKIIVMD      1495

Hum/MRP   KGEIQEYGAPSDL-LQQRGLFYSMAKDAGLV            1531
          :  . :   :   :  .:   .    .:  ::           :
Lei/PgpA  HGVVAEMGSPRELVMNHQSMFHSMVESLGSRGSKDFY      1532

Lei/PgpA  ELLMGRRIVQPAVLSD                            1548
```

Annexin II GAPDH

Protein A

Protein G

FIG. 12A
FIG. 12B
FIG. 12C
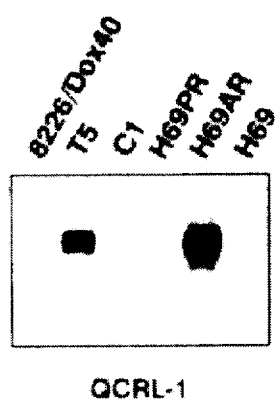
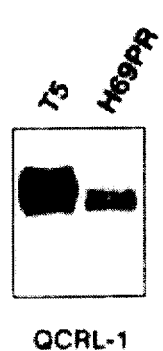
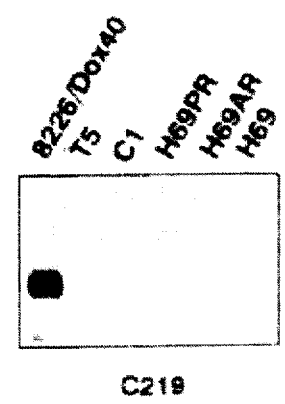

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 5011 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 196..4788

( x i ) SEQUENCE DESCRIPTION: SEQ ID NO:1:

```
CAGGCGGCGT  TGCGGCCCCG  GCCCCGGCTC  CCTGCGCCGC  CGCCGCCGCC  GCCGCCGCCG      60

CCGCCGCCGC  CGCCGCCAGC  GCTAGCGCCA  GCAGCCGGGC  CCGATCACCC  GCCGCCCGGT     120

GCCCGCCGCC  GCCCGCCGCCA  GCAACCGGGC  CCGATCACCC  GCCGCCCGGT  GCCCGCCGCC    180
```

-continued

| | | | | | | | | | | | | | | | |
|---|---|---|---|---|---|---|---|---|---|---|---|---|---|---|---|
| GCCCGCGCCA | CCGGC | ATG | GCG | CTC | CGG | GGC | TTC | TGC | AGC | GCC | GAT | GGC | TCC | | 231 |
| | | Met | Ala | Leu | Arg | Gly | Phe | Cys | Ser | Ala | Asp | Gly | Ser | | |
| | | 1 | | 5 | | | | | | 10 | | | | | |

| GAC | CCG | CTC | TGG | GAC | TGG | AAT | GTC | ACG | TGG | AAT | ACC | AGC | AAC | CCC | GAC | 279 |
|---|---|---|---|---|---|---|---|---|---|---|---|---|---|---|---|---|
| Asp | Pro | Leu | Trp | Asp | Trp | Asn | Val | Thr | Trp | Asn | Thr | Ser | Asn | Pro | Asp | |
| | | 15 | | | | 20 | | | | | 25 | | | | | |

| TTC | ACC | AAG | TGC | TTT | CAG | AAC | ACG | GTC | CTC | GTG | TGG | GTG | CCT | TGT | TTT | 327 |
|---|---|---|---|---|---|---|---|---|---|---|---|---|---|---|---|---|
| Phe | Thr | Lys | Cys | Phe | Gln | Asn | Thr | Val | Leu | Val | Trp | Val | Pro | Cys | Phe | |
| | 30 | | | | | 35 | | | | | 40 | | | | | |

| TAC | CTC | TGG | GCC | TGT | TTC | CCC | TTC | TAC | TTC | CTC | TAT | CTC | TCC | CGA | CAT | 375 |
|---|---|---|---|---|---|---|---|---|---|---|---|---|---|---|---|---|
| Tyr | Leu | Trp | Ala | Cys | Phe | Pro | Phe | Tyr | Phe | Leu | Tyr | Leu | Ser | Arg | His | |
| 45 | | | | 50 | | | | | 55 | | | | | 60 | | |

| GAC | CGA | GGC | TAC | ATT | CAG | ATG | ACA | CCT | CTC | AAC | AAA | ACC | AAA | ACT | GCC | 423 |
|---|---|---|---|---|---|---|---|---|---|---|---|---|---|---|---|---|
| Asp | Arg | Gly | Tyr | Ile | Gln | Met | Thr | Pro | Leu | Asn | Lys | Thr | Lys | Thr | Ala | |
| | | | | 65 | | | | | 70 | | | | | 75 | | |

| TTG | GGA | TTT | TTG | CTG | TGG | ATC | GTC | TGC | TGG | GCA | GAC | CTC | TTC | TAC | TCT | 471 |
|---|---|---|---|---|---|---|---|---|---|---|---|---|---|---|---|---|
| Leu | Gly | Phe | Leu | Leu | Trp | Ile | Val | Cys | Trp | Ala | Asp | Leu | Phe | Tyr | Ser | |
| | | | 80 | | | | | 85 | | | | | 90 | | | |

| TTC | TGG | GAA | AGA | AGT | CGG | GGC | ATA | TTC | CTG | GCC | CCA | GTG | TTT | CTG | GTC | 519 |
|---|---|---|---|---|---|---|---|---|---|---|---|---|---|---|---|---|
| Phe | Trp | Glu | Arg | Ser | Arg | Gly | Ile | Phe | Leu | Ala | Pro | Val | Phe | Leu | Val | |
| | | 95 | | | | | 100 | | | | | 105 | | | | |

| AGC | CCA | ACT | CTC | TTG | GGC | ATC | ACC | ACG | CTG | CTT | GCT | ACC | TTT | TTA | ATT | 567 |
|---|---|---|---|---|---|---|---|---|---|---|---|---|---|---|---|---|
| Ser | Pro | Thr | Leu | Leu | Gly | Ile | Thr | Thr | Leu | Leu | Ala | Thr | Phe | Leu | Ile | |
| 110 | | | | | 115 | | | | | 120 | | | | | | |

| CAG | CTG | GAG | AGG | AGG | AAG | GGA | GTT | CAG | TCT | TCA | GGG | ATC | ATG | CTC | ACT | 615 |
|---|---|---|---|---|---|---|---|---|---|---|---|---|---|---|---|---|
| Gln | Leu | Glu | Arg | Arg | Lys | Gly | Val | Gln | Ser | Ser | Gly | Ile | Met | Leu | Thr | |
| 125 | | | | 130 | | | | | 135 | | | | | 140 | | |

| TTC | TGG | CTG | GTA | GCC | CTA | GTG | TGT | GCC | CTA | GCC | ATC | CTG | AGA | TCC | AAA | 663 |
|---|---|---|---|---|---|---|---|---|---|---|---|---|---|---|---|---|
| Phe | Trp | Leu | Val | Ala | Leu | Val | Cys | Ala | Leu | Ala | Ile | Leu | Arg | Ser | Lys | |
| | | | | 145 | | | | | 150 | | | | | 155 | | |

| ATT | ATG | ACA | GCC | TTA | AAA | GAG | GAT | GCC | CAG | GTG | GAC | CTG | TTT | CGT | GAC | 711 |
|---|---|---|---|---|---|---|---|---|---|---|---|---|---|---|---|---|
| Ile | Met | Thr | Ala | Leu | Lys | Glu | Asp | Ala | Gln | Val | Asp | Leu | Phe | Arg | Asp | |
| | | | 160 | | | | | 165 | | | | | 170 | | | |

| ATC | ACT | TTC | TAC | GTC | TAC | TTT | TCC | CTC | TTA | CTC | ATT | CAG | CTC | GTC | TTG | 759 |
|---|---|---|---|---|---|---|---|---|---|---|---|---|---|---|---|---|
| Ile | Thr | Phe | Tyr | Val | Tyr | Phe | Ser | Leu | Leu | Leu | Ile | Gln | Leu | Val | Leu | |
| | | 175 | | | | | 180 | | | | | 185 | | | | |

| TCC | TGT | TTC | TCA | GAT | CGC | TCA | CCC | CTG | TTC | TCG | GAA | ACC | ATC | CAC | GAC | 807 |
|---|---|---|---|---|---|---|---|---|---|---|---|---|---|---|---|---|
| Ser | Cys | Phe | Ser | Asp | Arg | Ser | Pro | Leu | Phe | Ser | Glu | Thr | Ile | His | Asp | |
| 190 | | | | | 195 | | | | | 200 | | | | | | |

| CCT | AAT | CCC | TGC | CCA | GAG | TCC | AGC | GCT | TCC | TTC | CTG | TCG | AGG | ATC | ACC | 855 |
|---|---|---|---|---|---|---|---|---|---|---|---|---|---|---|---|---|
| Pro | Asn | Pro | Cys | Pro | Glu | Ser | Ser | Ala | Ser | Phe | Leu | Ser | Arg | Ile | Thr | |
| 205 | | | | 210 | | | | | 215 | | | | | 220 | | |

| TTC | TGG | TGG | ATC | ACA | GGG | TTG | ATT | GTC | CGG | GGC | TAC | CGC | CAG | CCC | CTG | 903 |
|---|---|---|---|---|---|---|---|---|---|---|---|---|---|---|---|---|
| Phe | Trp | Trp | Ile | Thr | Gly | Leu | Ile | Val | Arg | Gly | Tyr | Arg | Gln | Pro | Leu | |
| | | | | 225 | | | | | 230 | | | | | 235 | | |

| GAG | GGC | AGT | GAC | CTC | TGG | TCC | TTA | AAC | AAG | GAG | GAC | ACG | TCG | GAA | CAA | 951 |
|---|---|---|---|---|---|---|---|---|---|---|---|---|---|---|---|---|
| Glu | Gly | Ser | Asp | Leu | Trp | Ser | Leu | Asn | Lys | Glu | Asp | Thr | Ser | Glu | Gln | |
| | | | 240 | | | | | 245 | | | | | 250 | | | |

| GTC | GTG | CCT | GTT | TTG | GTA | AAG | AAC | TGG | AAG | AAG | GAA | TGC | GCC | AAG | ACT | 999 |
|---|---|---|---|---|---|---|---|---|---|---|---|---|---|---|---|---|
| Val | Val | Pro | Val | Leu | Val | Lys | Asn | Trp | Lys | Lys | Glu | Cys | Ala | Lys | Thr | |
| | | 255 | | | | | 260 | | | | | 265 | | | | |

| AGG | AAG | CAG | CCG | GTG | AAG | GTT | GTG | TAC | TCC | TCC | AAG | GAT | CCT | GCC | CAG | 1047 |
|---|---|---|---|---|---|---|---|---|---|---|---|---|---|---|---|---|
| Arg | Lys | Gln | Pro | Val | Lys | Val | Val | Tyr | Ser | Ser | Lys | Asp | Pro | Ala | Gln | |
| 270 | | | | | 275 | | | | | 280 | | | | | | |

| CCG | AAA | GAG | AGT | TCC | AAG | GTG | GAT | GCG | AAT | GAG | GAG | GTG | GAG | GCT | TTG | 1095 |
|---|---|---|---|---|---|---|---|---|---|---|---|---|---|---|---|---|
| Pro | Lys | Glu | Ser | Ser | Lys | Val | Asp | Ala | Asn | Glu | Glu | Val | Glu | Ala | Leu | |
| 285 | | | | 290 | | | | | 295 | | | | | 300 | | |

| ATC | GTC | AAG | TCC | CCA | CAG | AAG | GAG | TGG | AAC | CCC | TCT | CTG | TTT | AAG | GTG | 1143 |
|---|---|---|---|---|---|---|---|---|---|---|---|---|---|---|---|---|
| Ile | Val | Lys | Ser | Pro | Gln | Lys | Glu | Trp | Asn | Pro | Ser | Leu | Phe | Lys | Val | |
| | | | | 305 | | | | | 310 | | | | | 315 | | |

| | | | | | | | | | | | | | | | | |
|---|---|---|---|---|---|---|---|---|---|---|---|---|---|---|---|---|
| TTA | TAC | AAG | ACC | TTT | GGG | CCC | TAC | TTC | CTC | ATG | AGC | TTC | TTC | TTC | AAG | 1191 |
| Leu | Tyr | Lys | Thr<br>320 | Phe | Gly | Pro | Tyr<br>325 | Phe | Leu | Met | Ser | Phe<br>330 | Phe | Phe | Lys | |
| GCC | ATC | CAC | GAC | CTG | ATG | ATG | TTT | TCC | GGG | CCG | CAG | ATC | TTA | AAG | TTG | 1239 |
| Ala | Ile | His<br>335 | Asp | Leu | Met | Met | Phe<br>340 | Ser | Gly | Pro | Gln | Ile<br>345 | Leu | Lys | Leu | |
| CTC | ATC | AAG | TTC | GTG | AAT | GAC | ACG | AAG | GCC | CCA | GAC | TGG | CAG | GGC | TAC | 1287 |
| Leu | Ile | Lys<br>350 | Phe | Val | Asn | Asp<br>355 | Thr | Lys | Ala | Pro | Asp<br>360 | Trp | Gln | Gly | Tyr | |
| TTC | TAC | ACC | GTG | CTG | CTG | TTT | GTC | ACT | GCC | TGC | CTG | CAG | ACC | CTC | GTG | 1335 |
| Phe<br>365 | Tyr | Thr | Val | Leu<br>370 | Leu | Phe | Val | Thr | Ala<br>375 | Cys | Leu | Gln | Thr | Leu<br>380 | Val | |
| CTG | CAC | CAG | TAC | TTC | CAC | ATC | TGC | TTC | GTC | AGT | GGC | ATG | AGG | ATC | AAG | 1383 |
| Leu | His | Gln | Tyr | Phe<br>385 | His | Ile | Cys | Phe | Val<br>390 | Ser | Gly | Met | Arg | Ile<br>395 | Lys | |
| ACC | GCT | GTC | ATT | GGG | GCT | GTC | TAT | CGG | AAG | GCC | CTG | GTG | ATC | ACC | AAT | 1431 |
| Thr | Ala | Val | Ile<br>400 | Gly | Ala | Val | Tyr | Arg<br>405 | Lys | Ala | Leu | Val | Ile<br>410 | Thr | Asn | |
| TCA | GCC | AGA | AAA | TCC | TCC | ACG | GTC | GGG | GAG | ATT | GTC | AAC | CTC | ATG | TCT | 1479 |
| Ser | Ala | Arg | Lys<br>415 | Ser | Ser | Thr | Val<br>420 | Gly | Glu | Ile | Val | Asn<br>425 | Leu | Met | Ser | |
| GTG | GAC | GCT | CAG | AGG | TTC | ATG | GAC | TTG | GCC | ACG | TAC | ATT | AAC | ATG | ATC | 1527 |
| Val | Asp | Ala<br>430 | Gln | Arg | Phe | Met | Asp<br>435 | Leu | Ala | Thr | Tyr | Ile<br>440 | Asn | Met | Ile | |
| TGG | TCA | GCC | CCC | CTG | CAA | GTC | ATC | CTT | GCT | CTC | TAC | CTC | CTG | TGG | CTG | 1575 |
| Trp<br>445 | Ser | Ala | Pro | Leu | Gln<br>450 | Val | Ile | Leu | Ala | Leu<br>455 | Tyr | Leu | Leu | Trp | Leu<br>460 | |
| AAT | CTG | GGC | CCT | TCC | GTC | CTG | GCT | GGA | GTG | GCG | GTG | ATG | GTC | CTC | ATG | 1623 |
| Asn | Leu | Gly | Pro | Ser<br>465 | Val | Leu | Ala | Gly | Val<br>470 | Ala | Val | Met | Val | Leu<br>475 | Met | |
| GTG | CCC | GTC | AAT | GCT | GTG | ATG | GCG | ATG | AAG | ACC | AAG | ACG | TAT | CAG | GTG | 1671 |
| Val | Pro | Val | Asn<br>480 | Ala | Val | Met | Ala | Met<br>485 | Lys | Thr | Lys | Thr | Tyr<br>490 | Gln | Val | |
| GCC | CAC | ATG | AAG | AGC | AAA | GAC | AAT | CGG | ATC | AAG | CTG | ATG | AAC | GAA | ATT | 1719 |
| Ala | His | Met<br>495 | Lys | Ser | Lys | Asp | Asn<br>500 | Arg | Ile | Lys | Leu | Met<br>505 | Asn | Glu | Ile | |
| CTC | AAT | GGG | ATC | AAA | GTG | CTA | AAG | CTT | TAT | GCC | TGG | GAG | CTG | GCA | TTC | 1767 |
| Leu | Asn<br>510 | Gly | Ile | Lys | Val | Leu<br>515 | Lys | Leu | Tyr | Ala | Trp<br>520 | Glu | Leu | Ala | Phe | |
| AAG | GAC | AAG | GTG | CTG | GCC | ATC | AGG | CAG | GAG | GAG | CTG | AAG | GTG | CTG | AAG | 1815 |
| Lys<br>525 | Asp | Lys | Val | Leu | Ala<br>530 | Ile | Arg | Gln | Glu | Glu<br>535 | Leu | Lys | Val | Leu | Lys<br>540 | |
| AAG | TCT | GCC | TAC | CTG | TCA | GCC | GTG | GGC | ACC | TTC | ACC | TGG | GTC | TGC | ACG | 1863 |
| Lys | Ser | Ala | Tyr | Leu<br>545 | Ser | Ala | Val | Gly | Thr<br>550 | Phe | Thr | Trp | Val | Cys<br>555 | Thr | |
| CCC | TTT | CTG | GTG | GCC | TTG | TGC | ACA | TTT | GCC | GTC | TAC | GTG | ACC | ATT | GAC | 1911 |
| Pro | Phe | Leu | Val<br>560 | Ala | Leu | Cys | Thr | Phe<br>565 | Ala | Val | Tyr | Val | Thr<br>570 | Ile | Asp | |
| GAG | AAC | AAC | ATC | CTG | GAT | GCC | CAG | ACA | GCC | TTC | GTG | TCT | TTG | GCC | TTG | 1959 |
| Glu | Asn | Asn<br>575 | Ile | Leu | Asp | Ala | Gln<br>580 | Thr | Ala | Phe | Val | Ser<br>585 | Leu | Ala | Leu | |
| TTC | AAC | ATC | CTC | CGG | TTT | CCC | CTG | AAC | ATT | CTC | CCC | ATG | GTC | ATC | AGC | 2007 |
| Phe | Asn<br>590 | Ile | Leu | Arg | Phe | Pro<br>595 | Leu | Asn | Ile | Leu | Pro<br>600 | Met | Val | Ile | Ser | |
| AGC | ATC | GTG | CAG | GCG | AGT | GTC | TCC | CTC | AAA | CGC | CTG | AGG | ATC | TTT | CTC | 2055 |
| Ser | Ile<br>605 | Val | Gln | Ala | Ser<br>610 | Val | Ser | Leu | Lys | Arg<br>615 | Leu | Arg | Ile | Phe | Leu<br>620 | |
| TCC | CAT | GAG | GAG | CTG | GAA | CCT | GAC | AGC | ATC | GAG | CGA | CGG | CCT | GTC | AAA | 2103 |
| Ser | His | Glu | Glu | Leu<br>625 | Glu | Pro | Asp | Ser | Ile<br>630 | Glu | Arg | Arg | Pro | Val<br>635 | Lys | |

| | | | | | | | | | | | | | | | | |
|---|---|---|---|---|---|---|---|---|---|---|---|---|---|---|---|---|
| GAC | GGC | GGG | GGC | ACG | AAC | AGC | ATC | ACC | GTG | AGG | AAT | GCC | ACA | TTC | ACC | 2151 |
| Asp | Gly | Gly | Gly | Thr | Asn | Ser | Ile | Thr | Val | Arg | Asn | Ala | Thr | Phe | Thr | |
| | | | 640 | | | | 645 | | | | | | 650 | | | |
| TGG | GCC | AGG | AGC | GAC | CCT | CCC | ACA | CTG | AAT | GGC | ATC | ACC | TTC | TCC | ATC | 2199 |
| Trp | Ala | Arg | Ser | Asp | Pro | Pro | Thr | Leu | Asn | Gly | Ile | Thr | Phe | Ser | Ile | |
| | | 655 | | | | 660 | | | | | 665 | | | | | |
| CCC | GAA | GGT | GCT | TTG | GTG | GCC | GTG | GTG | GGC | CAG | GTG | GGC | TGC | GGA | AAG | 2247 |
| Pro | Glu | Gly | Ala | Leu | Val | Ala | Val | Val | Gly | Gln | Val | Gly | Cys | Gly | Lys | |
| | 670 | | | | 675 | | | | | 680 | | | | | | |
| TTG | TCC | CTG | CTC | TCA | GCC | CTC | TTG | GCT | GAG | ATG | GAC | AAA | GTG | GAG | GGG | 2295 |
| Leu | Ser | Leu | Leu | Ser | Ala | Leu | Leu | Ala | Glu | Met | Asp | Lys | Val | Glu | Gly | |
| 685 | | | | 690 | | | | | 695 | | | | | 700 | | |
| CAC | GTG | GCT | ATC | AAG | GGC | TCC | GTG | GCC | TAT | GTG | CCA | CAG | CAG | GCC | TGG | 2343 |
| His | Val | Ala | Ile | Lys | Gly | Ser | Val | Ala | Tyr | Val | Pro | Gln | Gln | Ala | Trp | |
| | | | | 705 | | | | | 710 | | | | | 715 | | |
| ATT | CAG | AAT | GAT | TCT | CTC | CGA | GAA | AAC | ATC | CTT | TTT | GGA | TGT | CAG | CTG | 2391 |
| Ile | Gln | Asn | Asp | Ser | Leu | Arg | Glu | Asn | Ile | Leu | Phe | Gly | Cys | Gln | Leu | |
| | | | 720 | | | | | 725 | | | | | 730 | | | |
| GAG | GAA | CCA | TAT | TAC | AGG | TCC | GTG | ATA | CAG | GCC | TGT | GCC | CTC | CTC | CCA | 2439 |
| Glu | Glu | Pro | Tyr | Tyr | Arg | Ser | Val | Ile | Gln | Ala | Cys | Ala | Leu | Leu | Pro | |
| | | 735 | | | | | 740 | | | | | 745 | | | | |
| GAC | CTG | GAA | ATC | CTG | CCC | AGT | GGG | GAT | CGG | ACA | GAG | ATT | GGC | GAG | AAG | 2487 |
| Asp | Leu | Glu | Ile | Leu | Pro | Ser | Gly | Asp | Arg | Thr | Glu | Ile | Gly | Glu | Lys | |
| | 750 | | | | | 755 | | | | | 760 | | | | | |
| GGC | GTG | AAC | CTG | TCT | GGG | GGA | CAG | AAG | CAG | CGC | GTG | AGC | CTG | GCC | CGG | 2535 |
| Gly | Val | Asn | Leu | Ser | Gly | Gly | Gln | Lys | Gln | Arg | Val | Ser | Leu | Ala | Arg | |
| 765 | | | | | 770 | | | | | 775 | | | | | 780 | |
| GCC | GTG | TAC | TCC | AAC | GCT | GAC | ATT | TAC | CTC | TTC | GAT | GAT | CCC | CTC | TCA | 2583 |
| Ala | Val | Tyr | Ser | Asn | Ala | Asp | Ile | Tyr | Leu | Phe | Asp | Asp | Pro | Leu | Ser | |
| | | | | 785 | | | | | 790 | | | | | 795 | | |
| GCA | GTG | GAT | GCC | CAT | GTG | GGA | AAA | CAC | ATC | TTT | GAA | AAT | GTG | ATT | GGC | 2631 |
| Ala | Val | Asp | Ala | His | Val | Gly | Lys | His | Ile | Phe | Glu | Asn | Val | Ile | Gly | |
| | | | 800 | | | | | 805 | | | | | 810 | | | |
| CCC | AAG | GGG | ATG | CTG | AAG | AAC | AAG | ACG | CGG | ATC | TTG | GTC | ACG | CAC | AGC | 2679 |
| Pro | Lys | Gly | Met | Leu | Lys | Asn | Lys | Thr | Arg | Ile | Leu | Val | Thr | His | Ser | |
| | 815 | | | | | 820 | | | | | 825 | | | | | |
| ATG | AGC | TAC | TTG | CCG | CAG | GTG | GAC | GTC | ATC | ATC | GTC | ATG | AGT | GGC | GGC | 2727 |
| Met | Ser | Tyr | Leu | Pro | Gln | Val | Asp | Val | Ile | Ile | Val | Met | Ser | Gly | Gly | |
| 830 | | | | | 835 | | | | | 840 | | | | | | |
| AAG | ATC | TCT | GAG | ATG | GGC | TCC | TAC | CAG | GAG | CTG | CTG | GCT | CGA | GAC | GGC | 2775 |
| Lys | Ile | Ser | Glu | Met | Gly | Ser | Tyr | Gln | Glu | Leu | Leu | Ala | Arg | Asp | Gly | |
| 845 | | | | | 850 | | | | | 855 | | | | | 860 | |
| GCC | TTC | GCT | GAG | TTC | CTG | CGT | ACC | TAT | GCC | AGC | ACA | GAG | CAG | GAG | CAG | 2823 |
| Ala | Phe | Ala | Glu | Phe | Leu | Arg | Thr | Tyr | Ala | Ser | Thr | Glu | Gln | Glu | Gln | |
| | | | | 865 | | | | | 870 | | | | | 875 | | |
| GAT | GCA | GAG | GAG | AAC | GGG | GTC | ACG | GGC | GTC | AGC | GGT | CCA | GGG | AAG | GAA | 2871 |
| Asp | Ala | Glu | Glu | Asn | Gly | Val | Thr | Gly | Val | Ser | Gly | Pro | Gly | Lys | Glu | |
| | | | 880 | | | | | 885 | | | | | 890 | | | |
| GCA | AAG | CAA | ATG | GAG | AAT | GGC | ATG | CTG | GTG | ACG | GAC | AGT | GCA | GGG | AAG | 2919 |
| Ala | Lys | Gln | Met | Glu | Asn | Gly | Met | Leu | Val | Thr | Asp | Ser | Ala | Gly | Lys | |
| | | 895 | | | | | 900 | | | | | 905 | | | | |
| CAA | CTG | CAG | AGA | CAG | CTC | AGC | AGC | TCC | TCC | TCC | TAT | AGT | GGG | GAC | ATC | 2967 |
| Gln | Leu | Gln | Arg | Gln | Leu | Ser | Ser | Ser | Ser | Ser | Tyr | Ser | Gly | Asp | Ile | |
| | 910 | | | | | 915 | | | | | 920 | | | | | |
| AGC | AGG | CAC | CAC | AAC | AGC | ACC | GCA | GAA | CTG | CAG | AAA | GCT | GAG | GCC | AAG | 3015 |
| Ser | Arg | His | His | Asn | Ser | Thr | Ala | Glu | Leu | Gln | Lys | Ala | Glu | Ala | Lys | |
| 925 | | | | | 930 | | | | | 935 | | | | | 940 | |
| AAG | GAG | GAG | ACC | TGG | AAG | CTG | ATG | GAG | GCT | GAC | AAG | GCG | CAG | ACA | GGG | 3063 |
| Lys | Glu | Glu | Thr | Trp | Lys | Leu | Met | Glu | Ala | Asp | Lys | Ala | Gln | Thr | Gly | |
| | | | | 945 | | | | | 950 | | | | | 955 | | |

```
CAG GTC AAG CTT TCC GTG TAC TGG GAC TAC ATG AAG GCC ATC GGA CTC    3111
Gln Val Lys Leu Ser Val Tyr Trp Asp Tyr Met Lys Ala Ile Gly Leu
        960                 965                 970

TTC ATC TCC TTC CTC AGC ATC TTC CTT TTC ATG TGT AAC CAT GTG TCC    3159
Phe Ile Ser Phe Leu Ser Ile Phe Leu Phe Met Cys Asn His Val Ser
        975                 980                 985

GCG CTG GCT TCC AAC TAT TGG CTC AGC CTC TGG ACT GAT GAC CCC ATC    3207
Ala Leu Ala Ser Asn Tyr Trp Leu Ser Leu Trp Thr Asp Asp Pro Ile
        990                 995                 1000

GTC AAC GGG ACT CAG GAG CAC ACG AAA GTC CGG CTG AGC GTC TAT GGA    3255
Val Asn Gly Thr Gln Glu His Thr Lys Val Arg Leu Ser Val Tyr Gly
        1005                1010                1015                1020

GCC CTG GGC ATT TCA CAA GGG ATC GCC GTG TTT GGC TAC TCC ATG GCC    3303
Ala Leu Gly Ile Ser Gln Gly Ile Ala Val Phe Gly Tyr Ser Met Ala
                1025                1030                1035

GTG TCC ATC GGG GGG ATC TTG GCT TCC CGC TGT CTG CAC GTG GAC CTG    3351
Val Ser Ile Gly Gly Ile Leu Ala Ser Arg Cys Leu His Val Asp Leu
                1040                1045                1050

CTG CAC AGC ATC CTG CGG TCA CCC ATG AGC TTC TTT GAG CGG ACC CCC    3399
Leu His Ser Ile Leu Arg Ser Pro Met Ser Phe Phe Glu Arg Thr Pro
                1055                1060                1065

AGT GGG AAC CTG GTG AAC CGC TTC TCC AAG GAG CTG GAC ACA GTG GAC    3447
Ser Gly Asn Leu Val Asn Arg Phe Ser Lys Glu Leu Asp Thr Val Asp
        1070                1075                1080

TCC ATG ATC CCG GAG GTC ATC AAG ATG TTC ATG GGC TCC CTG TTC AAC    3495
Ser Met Ile Pro Glu Val Ile Lys Met Phe Met Gly Ser Leu Phe Asn
1085                1090                1095                1100

GTC ATT GGT GCC TGC ATC GTT ATC CTG CTG GCC ACG CCC ATC GCC GCC    3543
Val Ile Gly Ala Cys Ile Val Ile Leu Leu Ala Thr Pro Ile Ala Ala
                1105                1110                1115

ATC ATC ATC CCG CCC CTT GGC CTC ATC TAC TTC TTC GTC CAG AGG TTC    3591
Ile Ile Ile Pro Pro Leu Gly Leu Ile Tyr Phe Phe Val Gln Arg Phe
                1120                1125                1130

TAC GTG GCT TCC TCC CGG CAG CTG AAG CGC CTC GAG TCG GTC AGC CGC    3639
Tyr Val Ala Ser Ser Arg Gln Leu Lys Arg Leu Glu Ser Val Ser Arg
                1135                1140                1145

TCC CCG GTC TAT TCC CAT TTC AAC GAG ACC TTG CTG GGG GTC AGC GTC    3687
Ser Pro Val Tyr Ser His Phe Asn Glu Thr Leu Leu Gly Val Ser Val
        1150                1155                1160

ATT CGA GCC TTC GAG GAG CAG GAG CGC TTC ATC CAC CAG AGT GAC CTG    3735
Ile Arg Ala Phe Glu Glu Gln Glu Arg Phe Ile His Gln Ser Asp Leu
1165                1170                1175                1180

AAG GTG GAC GAG AAC CAG AAG GCC TAT TAC CCC AGC ATC GTG GCC AAC    3783
Lys Val Asp Glu Asn Gln Lys Ala Tyr Tyr Pro Ser Ile Val Ala Asn
                1185                1190                1195

AGG TGG CTG GCC GTG CGG CTG GAG TGT GTG GGC AAC TGC ATC GTT CTG    3831
Arg Trp Leu Ala Val Arg Leu Glu Cys Val Gly Asn Cys Ile Val Leu
                1200                1205                1210

TTT GCT GCC CTG TTT GCG GTG ATC TCC AGG CAC AGC CTC AGT GCT GGC    3879
Phe Ala Ala Leu Phe Ala Val Ile Ser Arg His Ser Leu Ser Ala Gly
        1215                1220                1225

TTG GTG GGC CTC TCA GTG TCT TAC TCA TTG CAG GTC ACC ACG TAC TTG    3927
Leu Val Gly Leu Ser Val Ser Tyr Ser Leu Gln Val Thr Thr Tyr Leu
        1230                1235                1240

AAC TGG CTG GTT CGG ATG TCA TCT GAA ATG GAA ACC AAC ATC GTG GCC    3975
Asn Trp Leu Val Arg Met Ser Ser Glu Met Glu Thr Asn Ile Val Ala
1245                1250                1255                1260

GTG GAG AGG CTC AAG GAG TAT TCA GAG ACT GAG AAG GAG GCG CCC TGG    4023
Val Glu Arg Leu Lys Glu Tyr Ser Glu Thr Glu Lys Glu Ala Pro Trp
                1265                1270                1275
```

```
CAA ATC CAG GAG ACA CGT CCG CCC AGC AGC TGG CCC CAG GTG GGC CGA    4071
Gln Ile Gln Glu Thr Arg Pro Pro Ser Ser Trp Pro Gln Val Gly Arg
        1280                1285                1290

GTG GAA TTC CGG AAC TAC TGC CTG CGC TAC CGA GAG GAC CTG GAC TTC    4119
Val Glu Phe Arg Asn Tyr Cys Leu Arg Tyr Arg Glu Asp Leu Asp Phe
        1295                1300                1305

GTT CTC AGG CAC ATC AAT GTC ACG ATC AAT GGG GGA GAA AAG GTC GGC    4167
Val Leu Arg His Ile Asn Val Thr Ile Asn Gly Gly Glu Lys Val Gly
        1310                1315                1320

ATC GTG GGG CGG ACG GGA GCT GGG AAG TCG TCC CTG ACC CTG GGC TTA    4215
Ile Val Gly Arg Thr Gly Ala Gly Lys Ser Ser Leu Thr Leu Gly Leu
1325                1330                1335                1340

TTT CGG ATC AAC GAG TCT GCC GAA GGA GAG ATC ATC ATC GAT GGC ATC    4263
Phe Arg Ile Asn Glu Ser Ala Glu Gly Glu Ile Ile Ile Asp Gly Ile
                1345                1350                1355

AAC ATC GCC AAG ATC GGC CTG CAC GAC CTC CGC TTC AAG ATC ACC ATC    4311
Asn Ile Ala Lys Ile Gly Leu His Asp Leu Arg Phe Lys Ile Thr Ile
                1360                1365                1370

ATC CCC CAG GAC CCT GTT TTG TTT TCG GGT TCC CTC CGA ATG AAC CTG    4359
Ile Pro Gln Asp Pro Val Leu Phe Ser Gly Ser Leu Arg Met Asn Leu
        1375                1380                1385

GAC CCA TTC AGC CAG TAC TCG GAT GAA GAA GTC TGG ACG TCC CTG GAG    4407
Asp Pro Phe Ser Gln Tyr Ser Asp Glu Glu Val Trp Thr Ser Leu Glu
        1390                1395                1400

CTG GCC CAC CTG AAG GAC TTC GTG TCA GCC CTT CCT GAC AAG CTA GAC    4455
Leu Ala His Leu Lys Asp Phe Val Ser Ala Leu Pro Asp Lys Leu Asp
1405                1410                1415                1420

CAT GAA TGT GCA GAA GGC GGG GAG AAC CTC AGT GTC GGG CAG CGC CAG    4503
His Glu Cys Ala Glu Gly Gly Glu Asn Leu Ser Val Gly Gln Arg Gln
                1425                1430                1435

CTT GTG TGC CTA GCC CGG GCC CTG CTG AGG AAG ACG AAG ATC CTT GTG    4551
Leu Val Cys Leu Ala Arg Ala Leu Leu Arg Lys Thr Lys Ile Leu Val
                1440                1445                1450

TTG GAT GAG GCC ACG GCA GCC GTG GAC CTG GAA ACG GAC GAC CTC ATC    4599
Leu Asp Glu Ala Thr Ala Ala Val Asp Leu Glu Thr Asp Asp Leu Ile
        1455                1460                1465

CAG TCC ACC ATC CGG ACA CAG TTC GAG GAC TGC ACC GTC CTC ACC ATC    4647
Gln Ser Thr Ile Arg Thr Gln Phe Glu Asp Cys Thr Val Leu Thr Ile
        1470                1475                1480

GCC CAC CGG CTC AAC ACC ATC ATG GAC TAC ACA AGG GTG ATC GTC TTG    4695
Ala His Arg Leu Asn Thr Ile Met Asp Tyr Thr Arg Val Ile Val Leu
1485                1490                1495                1500

GAC AAA GGA GAA ATC CAG GAG TAC GGC GCC CCA TCG GAC CTC CTG CAG    4743
Asp Lys Gly Glu Ile Gln Glu Tyr Gly Ala Pro Ser Asp Leu Leu Gln
                1505                1510                1515

CAG AGA GGT CTT TTC TAC AGC ATG GCC AAA GAC GCC GGC TTG GTG         4788
Gln Arg Gly Leu Phe Tyr Ser Met Ala Lys Asp Ala Gly Leu Val
        1520                1525                1530

TGAGCCCCAG AGCTGGCATA TCTGGTCAGA ACTGCAGGGC CTATATGCCA GCGCCCCAGG  4848

GAGGAGTCAG TACCCCTGGT AAACCAAGCC TCCACACTG AAACCAAAAC ATAAAAACCA   4908

AACCCAGACA ACCAAAACAT ATTCAAAGCA GCAGCCACCG CCATCCGGTC CCCTGCCTGG  4968

AACTGGCTGT GAAGACCCAG GAGAGACAGA GATGCGAACC ACC                    5011
```

( 2 ) INFORMATION FOR SEQ ID NO:2:

( i ) SEQUENCE CHARACTERISTICS:
( A ) LENGTH: 1531 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Ala | Leu | Arg | Gly | Phe | Cys | Ser | Ala | Asp | Gly | Ser | Asp | Pro | Leu | Trp |
|---|---|---|---|---|---|---|---|---|---|---|---|---|---|---|---|
| 1 | | | | 5 | | | | | 10 | | | | | 15 | |

| Asp | Trp | Asn | Val | Thr | Trp | Asn | Thr | Ser | Asn | Pro | Asp | Phe | Thr | Lys | Cys |
|---|---|---|---|---|---|---|---|---|---|---|---|---|---|---|---|
| | | | 20 | | | | | 25 | | | | | 30 | | |

| Phe | Gln | Asn | Thr | Val | Leu | Val | Trp | Val | Pro | Cys | Phe | Tyr | Leu | Trp | Ala |
|---|---|---|---|---|---|---|---|---|---|---|---|---|---|---|---|
| | | 35 | | | | 40 | | | | | | 45 | | | |

| Cys | Phe | Pro | Phe | Tyr | Phe | Leu | Tyr | Leu | Ser | Arg | His | Asp | Arg | Gly | Tyr |
|---|---|---|---|---|---|---|---|---|---|---|---|---|---|---|---|
| | 50 | | | | | 55 | | | | | 60 | | | | |

| Ile | Gln | Met | Thr | Pro | Leu | Asn | Lys | Thr | Lys | Thr | Ala | Leu | Gly | Phe | Leu |
|---|---|---|---|---|---|---|---|---|---|---|---|---|---|---|---|
| 65 | | | | | 70 | | | | | 75 | | | | | 80 |

| Leu | Trp | Ile | Val | Cys | Trp | Ala | Asp | Leu | Phe | Tyr | Ser | Phe | Trp | Glu | Arg |
|---|---|---|---|---|---|---|---|---|---|---|---|---|---|---|---|
| | | | | 85 | | | | | 90 | | | | | 95 | |

| Ser | Arg | Gly | Ile | Phe | Leu | Ala | Pro | Val | Phe | Leu | Val | Ser | Pro | Thr | Leu |
|---|---|---|---|---|---|---|---|---|---|---|---|---|---|---|---|
| | | | 100 | | | | | 105 | | | | | 110 | | |

| Leu | Gly | Ile | Thr | Thr | Leu | Leu | Ala | Thr | Phe | Leu | Ile | Gln | Leu | Glu | Arg |
|---|---|---|---|---|---|---|---|---|---|---|---|---|---|---|---|
| | | 115 | | | | 120 | | | | | 125 | | | | |

| Arg | Lys | Gly | Val | Gln | Ser | Ser | Gly | Ile | Met | Leu | Thr | Phe | Trp | Leu | Val |
|---|---|---|---|---|---|---|---|---|---|---|---|---|---|---|---|
| | 130 | | | | | 135 | | | | | 140 | | | | |

| Ala | Leu | Val | Cys | Ala | Leu | Ala | Ile | Leu | Arg | Ser | Lys | Ile | Met | Thr | Ala |
|---|---|---|---|---|---|---|---|---|---|---|---|---|---|---|---|
| 145 | | | | | 150 | | | | | 155 | | | | | 160 |

| Leu | Lys | Glu | Asp | Ala | Gln | Val | Asp | Leu | Phe | Arg | Asp | Ile | Thr | Phe | Tyr |
|---|---|---|---|---|---|---|---|---|---|---|---|---|---|---|---|
| | | | | 165 | | | | | 170 | | | | | 175 | |

| Val | Tyr | Phe | Ser | Leu | Leu | Leu | Ile | Gln | Leu | Val | Leu | Ser | Cys | Phe | Ser |
|---|---|---|---|---|---|---|---|---|---|---|---|---|---|---|---|
| | | | 180 | | | | | 185 | | | | | 190 | | |

| Asp | Arg | Ser | Pro | Leu | Phe | Ser | Glu | Thr | Ile | His | Asp | Pro | Asn | Pro | Cys |
|---|---|---|---|---|---|---|---|---|---|---|---|---|---|---|---|
| | | 195 | | | | 200 | | | | | 205 | | | | |

| Pro | Glu | Ser | Ser | Ala | Ser | Phe | Leu | Ser | Arg | Ile | Thr | Phe | Trp | Trp | Ile |
|---|---|---|---|---|---|---|---|---|---|---|---|---|---|---|---|
| | 210 | | | | | 215 | | | | | 220 | | | | |

| Thr | Gly | Leu | Ile | Val | Arg | Gly | Tyr | Arg | Gln | Pro | Leu | Glu | Gly | Ser | Asp |
|---|---|---|---|---|---|---|---|---|---|---|---|---|---|---|---|
| 225 | | | | | 230 | | | | | 235 | | | | | 240 |

| Leu | Trp | Ser | Leu | Asn | Lys | Glu | Asp | Thr | Ser | Glu | Gln | Val | Val | Pro | Val |
|---|---|---|---|---|---|---|---|---|---|---|---|---|---|---|---|
| | | | | 245 | | | | | 250 | | | | | 255 | |

| Leu | Val | Lys | Asn | Trp | Lys | Lys | Glu | Cys | Ala | Lys | Thr | Arg | Lys | Gln | Pro |
|---|---|---|---|---|---|---|---|---|---|---|---|---|---|---|---|
| | | | 260 | | | | | 265 | | | | | 270 | | |

| Val | Lys | Val | Val | Tyr | Ser | Ser | Lys | Asp | Pro | Ala | Gln | Pro | Lys | Glu | Ser |
|---|---|---|---|---|---|---|---|---|---|---|---|---|---|---|---|
| | | 275 | | | | 280 | | | | | 285 | | | | |

| Ser | Lys | Val | Asp | Ala | Asn | Glu | Glu | Val | Glu | Ala | Leu | Ile | Val | Lys | Ser |
|---|---|---|---|---|---|---|---|---|---|---|---|---|---|---|---|
| | 290 | | | | | 295 | | | | | 300 | | | | |

| Pro | Gln | Lys | Glu | Trp | Asn | Pro | Ser | Leu | Phe | Lys | Val | Leu | Tyr | Lys | Thr |
|---|---|---|---|---|---|---|---|---|---|---|---|---|---|---|---|
| 305 | | | | | 310 | | | | | 315 | | | | | 320 |

| Phe | Gly | Pro | Tyr | Phe | Leu | Met | Ser | Phe | Phe | Phe | Lys | Ala | Ile | His | Asp |
|---|---|---|---|---|---|---|---|---|---|---|---|---|---|---|---|
| | | | | 325 | | | | | 330 | | | | | 335 | |

| Leu | Met | Met | Phe | Ser | Gly | Pro | Gln | Ile | Leu | Lys | Leu | Leu | Ile | Lys | Phe |
|---|---|---|---|---|---|---|---|---|---|---|---|---|---|---|---|
| | | | 340 | | | | | 345 | | | | | 350 | | |

| Val | Asn | Asp | Thr | Lys | Ala | Pro | Asp | Trp | Gln | Gly | Tyr | Phe | Tyr | Thr | Val |
|---|---|---|---|---|---|---|---|---|---|---|---|---|---|---|---|
| | | 355 | | | | 360 | | | | | 365 | | | | |

| Leu | Leu | Phe | Val | Thr | Ala | Cys | Leu | Gln | Thr | Leu | Val | Leu | His | Gln | Tyr |
|---|---|---|---|---|---|---|---|---|---|---|---|---|---|---|---|
| | 370 | | | | | 375 | | | | | 380 | | | | |

| Phe | His | Ile | Cys | Phe | Val | Ser | Gly | Met | Arg | Ile | Lys | Thr | Ala | Val | Ile |
|---|---|---|---|---|---|---|---|---|---|---|---|---|---|---|---|
| 385 | | | | | 390 | | | | | 395 | | | | | 400 |

| Gly | Ala | Val | Tyr | Arg | Lys | Ala | Leu | Val | Ile | Thr | Asn | Ser | Ala | Arg | Lys |
|---|---|---|---|---|---|---|---|---|---|---|---|---|---|---|---|

|     |     |     |     | 405 |     |     |     | 410 |     |     |     | 415 |     |
|-----|-----|-----|-----|-----|-----|-----|-----|-----|-----|-----|-----|-----|-----|
| Ser | Ser | Thr | Val | Gly | Glu | Ile | Val | Asn | Leu | Met | Ser | Val | Asp | Ala | Gln |
|     |     |     | 420 |     |     |     | 425 |     |     |     | 430 |     |     |
| Arg | Phe | Met | Asp | Leu | Ala | Thr | Tyr | Ile | Asn | Met | Ile | Trp | Ser | Ala | Pro |
|     |     | 435 |     |     |     | 440 |     |     |     | 445 |     |     |     |
| Leu | Gln | Val | Ile | Leu | Ala | Leu | Tyr | Leu | Leu | Trp | Leu | Asn | Leu | Gly | Pro |
| 450 |     |     |     | 455 |     |     |     | 460 |     |     |     |
| Ser | Val | Leu | Ala | Gly | Val | Ala | Val | Met | Val | Leu | Met | Val | Pro | Val | Asn |
| 465 |     |     |     | 470 |     |     |     | 475 |     |     |     | 480 |
| Ala | Val | Met | Ala | Met | Lys | Thr | Lys | Thr | Tyr | Gln | Val | Ala | His | Met | Lys |
|     |     |     | 485 |     |     |     | 490 |     |     |     | 495 |
| Ser | Lys | Asp | Asn | Arg | Ile | Lys | Leu | Met | Asn | Glu | Ile | Leu | Asn | Gly | Ile |
|     |     | 500 |     |     |     | 505 |     |     |     | 510 |
| Lys | Val | Leu | Lys | Leu | Tyr | Ala | Trp | Glu | Leu | Ala | Phe | Lys | Asp | Lys | Val |
|     |     | 515 |     |     |     | 520 |     |     |     | 525 |
| Leu | Ala | Ile | Arg | Gln | Glu | Leu | Lys | Val | Leu | Lys | Lys | Ser | Ala | Tyr |
|     | 530 |     |     |     | 535 |     |     |     | 540 |
| Leu | Ser | Ala | Val | Gly | Thr | Phe | Thr | Trp | Val | Cys | Thr | Pro | Phe | Leu | Val |
| 545 |     |     |     | 550 |     |     |     | 555 |     |     |     | 560 |
| Ala | Leu | Cys | Thr | Phe | Ala | Val | Tyr | Val | Thr | Ile | Asp | Glu | Asn | Asn | Ile |
|     |     |     | 565 |     |     |     | 570 |     |     |     | 575 |
| Leu | Asp | Ala | Gln | Thr | Ala | Phe | Val | Ser | Leu | Ala | Leu | Phe | Asn | Ile | Leu |
|     |     |     | 580 |     |     |     | 585 |     |     |     | 590 |
| Arg | Phe | Pro | Leu | Asn | Ile | Leu | Pro | Met | Val | Ile | Ser | Ser | Ile | Val | Gln |
|     |     | 595 |     |     |     | 600 |     |     |     | 605 |
| Ala | Ser | Val | Ser | Leu | Lys | Arg | Leu | Arg | Ile | Phe | Leu | Ser | His | Glu | Glu |
|     | 610 |     |     |     | 615 |     |     |     | 620 |
| Leu | Glu | Pro | Asp | Ser | Ile | Glu | Arg | Arg | Pro | Val | Lys | Asp | Gly | Gly |
| 625 |     |     |     | 630 |     |     |     | 635 |     |     |     | 640 |
| Thr | Asn | Ser | Ile | Thr | Val | Arg | Asn | Ala | Thr | Phe | Thr | Trp | Ala | Arg | Ser |
|     |     |     | 645 |     |     |     | 650 |     |     |     | 655 |
| Asp | Pro | Pro | Thr | Leu | Asn | Gly | Ile | Thr | Phe | Ser | Ile | Pro | Glu | Gly | Ala |
|     |     |     | 660 |     |     |     | 665 |     |     |     | 670 |
| Leu | Val | Ala | Val | Val | Gly | Gln | Val | Gly | Cys | Gly | Lys | Leu | Ser | Leu | Leu |
|     |     | 675 |     |     |     | 680 |     |     |     | 685 |
| Ser | Ala | Leu | Leu | Ala | Glu | Met | Asp | Lys | Val | Glu | Gly | His | Val | Ala | Ile |
|     | 690 |     |     |     | 695 |     |     |     | 700 |
| Lys | Gly | Ser | Val | Ala | Tyr | Val | Pro | Gln | Gln | Ala | Trp | Ile | Gln | Asn | Asp |
| 705 |     |     |     | 710 |     |     |     | 715 |     |     |     | 720 |
| Ser | Leu | Arg | Glu | Asn | Ile | Leu | Phe | Gly | Cys | Gln | Leu | Glu | Glu | Pro | Tyr |
|     |     |     | 725 |     |     |     | 730 |     |     |     | 735 |
| Tyr | Arg | Ser | Val | Ile | Gln | Ala | Cys | Ala | Leu | Leu | Pro | Asp | Leu | Glu | Ile |
|     |     | 740 |     |     |     | 745 |     |     |     | 750 |
| Leu | Pro | Ser | Gly | Asp | Arg | Thr | Glu | Ile | Gly | Glu | Lys | Gly | Val | Asn | Leu |
|     |     | 755 |     |     |     | 760 |     |     |     | 765 |
| Ser | Gly | Gly | Gln | Lys | Gln | Arg | Val | Ser | Leu | Ala | Arg | Ala | Val | Tyr | Ser |
|     | 770 |     |     |     | 775 |     |     |     | 780 |
| Asn | Ala | Asp | Ile | Tyr | Leu | Phe | Asp | Asp | Pro | Leu | Ser | Ala | Val | Asp | Ala |
| 785 |     |     |     | 790 |     |     |     | 795 |     |     |     | 800 |
| His | Val | Gly | Lys | His | Ile | Phe | Glu | Asn | Val | Ile | Gly | Pro | Lys | Gly | Met |
|     |     |     | 805 |     |     |     | 810 |     |     |     | 815 |
| Leu | Lys | Asn | Lys | Thr | Arg | Ile | Leu | Val | Thr | His | Ser | Met | Ser | Tyr | Leu |
|     |     |     | 820 |     |     |     | 825 |     |     |     | 830 |

-continued

```
Pro  Gln  Val  Asp  Val  Ile  Ile  Val  Met  Ser  Gly  Gly  Lys  Ile  Ser  Glu
          835                       840                      845
Met  Gly  Ser  Tyr  Gln  Glu  Leu  Leu  Ala  Arg  Asp  Gly  Ala  Phe  Ala  Glu
     850                       855                      860
Phe  Leu  Arg  Thr  Tyr  Ala  Ser  Thr  Glu  Gln  Glu  Gln  Asp  Ala  Glu  Glu
865                      870                      875                      880
Asn  Gly  Val  Thr  Gly  Val  Ser  Gly  Pro  Gly  Lys  Glu  Ala  Lys  Gln  Met
                    885                      890                      895
Glu  Asn  Gly  Met  Leu  Val  Thr  Asp  Ser  Ala  Gly  Lys  Gln  Leu  Gln  Arg
               900                      905                      910
Gln  Leu  Ser  Ser  Ser  Ser  Ser  Tyr  Ser  Gly  Asp  Ile  Ser  Arg  His  His
          915                       920                      925
Asn  Ser  Thr  Ala  Glu  Leu  Gln  Lys  Ala  Glu  Ala  Lys  Lys  Glu  Glu  Thr
     930                       935                      940
Trp  Lys  Leu  Met  Glu  Ala  Asp  Lys  Ala  Gln  Thr  Gly  Gln  Val  Lys  Leu
945                      950                      955                      960
Ser  Val  Tyr  Trp  Asp  Tyr  Met  Lys  Ala  Ile  Gly  Leu  Phe  Ile  Ser  Phe
                    965                      970                      975
Leu  Ser  Ile  Phe  Leu  Phe  Met  Cys  Asn  His  Val  Ser  Ala  Leu  Ala  Ser
               980                      985                      990
Asn  Tyr  Trp  Leu  Ser  Leu  Trp  Thr  Asp  Asp  Pro  Ile  Val  Asn  Gly  Thr
          995                      1000                     1005
Gln  Glu  His  Thr  Lys  Val  Arg  Leu  Ser  Val  Tyr  Gly  Ala  Leu  Gly  Ile
     1010                      1015                     1020
Ser  Gln  Gly  Ile  Ala  Val  Phe  Gly  Tyr  Ser  Met  Ala  Val  Ser  Ile  Gly
1025                     1030                     1035                     1040
Gly  Ile  Leu  Ala  Ser  Arg  Cys  Leu  His  Val  Asp  Leu  Leu  His  Ser  Ile
                    1045                     1050                     1055
Leu  Arg  Ser  Pro  Met  Ser  Phe  Phe  Glu  Arg  Thr  Pro  Ser  Gly  Asn  Leu
               1060                     1065                     1070
Val  Asn  Arg  Phe  Ser  Lys  Glu  Leu  Asp  Thr  Val  Asp  Ser  Met  Ile  Pro
          1075                     1080                     1085
Glu  Val  Ile  Lys  Met  Phe  Met  Gly  Ser  Leu  Phe  Asn  Val  Ile  Gly  Ala
     1090                     1095                     1100
Cys  Ile  Val  Ile  Leu  Leu  Ala  Thr  Pro  Ile  Ala  Ala  Ile  Ile  Ile  Pro
1105                     1110                     1115                     1120
Pro  Leu  Gly  Leu  Ile  Tyr  Phe  Phe  Val  Gln  Arg  Phe  Tyr  Val  Ala  Ser
                    1125                     1130                     1135
Ser  Arg  Gln  Leu  Lys  Arg  Leu  Glu  Ser  Val  Ser  Arg  Ser  Pro  Val  Tyr
               1140                     1145                     1150
Ser  His  Phe  Asn  Glu  Thr  Leu  Leu  Gly  Val  Ser  Val  Ile  Arg  Ala  Phe
          1155                     1160                     1165
Glu  Glu  Gln  Glu  Arg  Phe  Ile  His  Gln  Ser  Asp  Leu  Lys  Val  Asp  Glu
     1170                     1175                     1180
Asn  Gln  Lys  Ala  Tyr  Tyr  Pro  Ser  Ile  Val  Ala  Asn  Arg  Trp  Leu  Ala
1185                     1190                     1195                     1200
Val  Arg  Leu  Glu  Cys  Val  Gly  Asn  Cys  Ile  Val  Leu  Phe  Ala  Ala  Leu
                    1205                     1210                     1215
Phe  Ala  Val  Ile  Ser  Arg  His  Ser  Leu  Ser  Ala  Gly  Leu  Val  Gly  Leu
               1220                     1225                     1230
Ser  Val  Ser  Tyr  Ser  Leu  Gln  Val  Thr  Thr  Tyr  Leu  Asn  Trp  Leu  Val
          1235                     1240                     1245
Arg  Met  Ser  Ser  Glu  Met  Glu  Thr  Asn  Ile  Val  Ala  Val  Glu  Arg  Leu
     1250                     1255                     1260
```

| | | | | | | | | | | | | | | |
|---|---|---|---|---|---|---|---|---|---|---|---|---|---|---|
| Lys | Glu | Tyr | Ser | Glu | Thr | Glu | Lys | Glu | Ala | Pro | Trp | Gln | Ile | Gln | Glu |
| 1265 | | | | 1270 | | | | 1275 | | | | | | 1280 |

Thr Arg Pro Pro Ser Ser Trp Pro Gln Val Gly Arg Val Glu Phe Arg
                    1285                1290                1295

Asn Tyr Cys Leu Arg Tyr Arg Glu Asp Leu Asp Phe Val Leu Arg His
                1300                1305                1310

Ile Asn Val Thr Ile Asn Gly Gly Glu Lys Val Gly Ile Val Gly Arg
             1315                1320                1325

Thr Gly Ala Gly Lys Ser Ser Leu Thr Leu Gly Leu Phe Arg Ile Asn
         1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
             1365                1370                1375

Pro Val Leu Phe Ser Gly Ser Leu Arg Met Asn Leu Asp Pro Phe Ser
             1380                1385                1390

Gln Tyr Ser Asp Glu Glu Val Trp Thr Ser Leu Glu Leu Ala His Leu
         1395                1400                1405

Lys Asp Phe Val Ser Ala Leu Pro Asp Lys Leu Asp His Glu Cys Ala
     1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
             1445                1450                1455

Thr Ala Ala Val Asp Leu Glu Thr Asp Asp Leu Ile Gln Ser Thr Ile
         1460                1465                1470

Arg Thr Gln Phe Glu Asp Cys Thr Val Leu Thr Ile Ala His Arg Leu
     1475                1480                1485

Asn Thr Ile Met Asp Tyr Thr Arg Val Ile Val Leu Asp Lys Gly Glu
     1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
             1525                1530

( 2 ) INFORMATION FOR SEQ ID NO:3:

( i ) SEQUENCE CHARACTERISTICS:
        ( A ) LENGTH: 5011 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 196..4788

( x i ) SEQUENCE DESCRIPTION: SEQ ID NO:3:

```
CAGGCGGCGT TGCGGCCCCG GCCCCGGCTC CCTGCGCCGC CGCCGCCGCC GCCGCCGCCG      60

CCGCCGCCGC CGCCGCCAGC GCTAGCGCCA GCAGCCGGGC CCGATCACCC GCCGCCCGGT     120

GCCCGCCGCC GCCCGCGCCA GCAACCGGGC CCGATCACCC GCCGCCCGGT GCCCGCCGCC     180

GCCCGCGCCA CCGGC ATG GCG CTC CGG GGC TTC TGC AGC GCC GAT GGC TCC     231
                Met Ala Leu Arg Gly Phe Cys Ser Ala Asp Gly Ser
                  1               5                  10

GAC CCG CTC TGG GAC TGG AAT GTC ACG TGG AAT ACC AGC AAC CCC GAC     279
```

-continued

| | | | | | | | | | | | | | | | | |
|---|---|---|---|---|---|---|---|---|---|---|---|---|---|---|---|---|
| Asp | Pro | Leu | Trp | Asp | Trp | Asn | Val | Thr | Trp | Asn | Thr | Ser | Asn | Pro | Asp | |
| | | 15 | | | | 20 | | | | | 25 | | | | | |

| TTC | ACC | AAG | TGC | TTT | CAG | AAC | ACG | GTC | CTC | GTG | TGG | GTG | CCT | TGT | TTT | 327 |
|---|---|---|---|---|---|---|---|---|---|---|---|---|---|---|---|---|
| Phe | Thr | Lys | Cys | Phe | Gln | Asn | Thr | Val | Leu | Val | Trp | Val | Pro | Cys | Phe | |
| | 30 | | | | 35 | | | | | 40 | | | | | | |

| TAC | CTC | TGG | GCC | TGT | TTC | CCC | TTC | TAC | TTC | CTC | TAT | CTC | TCC | CGA | CAT | 375 |
|---|---|---|---|---|---|---|---|---|---|---|---|---|---|---|---|---|
| Tyr | Leu | Trp | Ala | Cys | Phe | Pro | Phe | Tyr | Phe | Leu | Tyr | Leu | Ser | Arg | His | |
| 45 | | | | 50 | | | | | 55 | | | | | 60 | | |

| GAC | CGA | GGC | TAC | ATT | CAG | ATG | ACA | CCT | CTC | AAC | AAA | ACC | AAA | ACT | GCC | 423 |
|---|---|---|---|---|---|---|---|---|---|---|---|---|---|---|---|---|
| Asp | Arg | Gly | Tyr | Ile | Gln | Met | Thr | Pro | Leu | Asn | Lys | Thr | Lys | Thr | Ala | |
| | | | | 65 | | | | | 70 | | | | | 75 | | |

| TTG | GGA | TTT | TTG | CTG | TGG | ATC | GTC | TGC | TGG | GCA | GAC | CTC | TTC | TAC | TCT | 471 |
|---|---|---|---|---|---|---|---|---|---|---|---|---|---|---|---|---|
| Leu | Gly | Phe | Leu | Leu | Trp | Ile | Val | Cys | Trp | Ala | Asp | Leu | Phe | Tyr | Ser | |
| | | | 80 | | | | | 85 | | | | | 90 | | | |

| TTC | TGG | GAA | AGA | AGT | CGG | GGC | ATA | TTC | CTG | GCC | CCA | GTG | TTT | CTG | GTC | 519 |
|---|---|---|---|---|---|---|---|---|---|---|---|---|---|---|---|---|
| Phe | Trp | Glu | Arg | Ser | Arg | Gly | Ile | Phe | Leu | Ala | Pro | Val | Phe | Leu | Val | |
| | | 95 | | | | | 100 | | | | | 105 | | | | |

| AGC | CCA | ACT | CTC | TTG | GGC | ATC | ACC | ACG | CTG | CTT | GCT | ACC | TTT | TTA | ATT | 567 |
|---|---|---|---|---|---|---|---|---|---|---|---|---|---|---|---|---|
| Ser | Pro | Thr | Leu | Leu | Gly | Ile | Thr | Thr | Leu | Leu | Ala | Thr | Phe | Leu | Ile | |
| | 110 | | | | | 115 | | | | | 120 | | | | | |

| CAG | CTG | GAG | AGG | AGG | AAG | GGA | GTT | CAG | TCT | TCA | GGG | ATC | ATG | CTC | ACT | 615 |
|---|---|---|---|---|---|---|---|---|---|---|---|---|---|---|---|---|
| Gln | Leu | Glu | Arg | Arg | Lys | Gly | Val | Gln | Ser | Ser | Gly | Ile | Met | Leu | Thr | |
| 125 | | | | 130 | | | | | 135 | | | | | 140 | | |

| TTC | TGG | CTG | GTA | GCC | CTA | GTG | TGT | GCC | CTA | GCC | ATC | CTG | AGA | TCC | AAA | 663 |
|---|---|---|---|---|---|---|---|---|---|---|---|---|---|---|---|---|
| Phe | Trp | Leu | Val | Ala | Leu | Val | Cys | Ala | Leu | Ala | Ile | Leu | Arg | Ser | Lys | |
| | | | | 145 | | | | | 150 | | | | | 155 | | |

| ATT | ATG | ACA | GCC | TTA | AAA | GAG | GAT | GCC | CAG | GTG | GAC | CTG | TTT | CGT | GAC | 711 |
|---|---|---|---|---|---|---|---|---|---|---|---|---|---|---|---|---|
| Ile | Met | Thr | Ala | Leu | Lys | Glu | Asp | Ala | Gln | Val | Asp | Leu | Phe | Arg | Asp | |
| | | | | 160 | | | | | 165 | | | | | 170 | | |

| ATC | ACT | TTC | TAC | GTC | TAC | TTT | TCC | CTC | TTA | CTC | ATT | CAG | CTC | GTC | TTG | 759 |
|---|---|---|---|---|---|---|---|---|---|---|---|---|---|---|---|---|
| Ile | Thr | Phe | Tyr | Val | Tyr | Phe | Ser | Leu | Leu | Leu | Ile | Gln | Leu | Val | Leu | |
| | | | 175 | | | | | 180 | | | | | 185 | | | |

| TCC | TGT | TTC | TCA | GAT | CGC | TCA | CCC | CTG | TTC | TCG | GAA | ACC | ATC | CAC | GAC | 807 |
|---|---|---|---|---|---|---|---|---|---|---|---|---|---|---|---|---|
| Ser | Cys | Phe | Ser | Asp | Arg | Ser | Pro | Leu | Phe | Ser | Glu | Thr | Ile | His | Asp | |
| | 190 | | | | | 195 | | | | | 200 | | | | | |

| CCT | AAT | CCC | TGC | CCA | GAG | TCC | AGC | GCT | TCC | TTC | CTG | TCG | AGG | ATC | ACC | 855 |
|---|---|---|---|---|---|---|---|---|---|---|---|---|---|---|---|---|
| Pro | Asn | Pro | Cys | Pro | Glu | Ser | Ser | Ala | Ser | Phe | Leu | Ser | Arg | Ile | Thr | |
| 205 | | | | | 210 | | | | | 215 | | | | | 220 | |

| TTC | TGG | TGG | ATC | ACA | GGG | TTG | ATT | GTC | CGG | GGC | TAC | CGC | CAG | CCC | CTG | 903 |
|---|---|---|---|---|---|---|---|---|---|---|---|---|---|---|---|---|
| Phe | Trp | Trp | Ile | Thr | Gly | Leu | Ile | Val | Arg | Gly | Tyr | Arg | Gln | Pro | Leu | |
| | | | | 225 | | | | | 230 | | | | | 235 | | |

| GAG | GGC | AGT | GAC | CTC | TGG | TCC | TTA | AAC | AAG | GAG | GAC | ACG | TCG | GAA | CAA | 951 |
|---|---|---|---|---|---|---|---|---|---|---|---|---|---|---|---|---|
| Glu | Gly | Ser | Asp | Leu | Trp | Ser | Leu | Asn | Lys | Glu | Asp | Thr | Ser | Glu | Gln | |
| | | | 240 | | | | | 245 | | | | | 250 | | | |

| GTC | GTG | CCT | GTT | TTG | GTA | AAG | AAC | TGG | AAG | AAG | GAA | TGC | GCC | AAG | ACT | 999 |
|---|---|---|---|---|---|---|---|---|---|---|---|---|---|---|---|---|
| Val | Val | Pro | Val | Leu | Val | Lys | Asn | Trp | Lys | Lys | Glu | Cys | Ala | Lys | Thr | |
| | | 255 | | | | | 260 | | | | | 265 | | | | |

| AGG | AAG | CAG | CCG | GTG | AAG | GTT | GTG | TAC | TCC | TCC | AAG | GAT | CCT | GCC | CAG | 1047 |
|---|---|---|---|---|---|---|---|---|---|---|---|---|---|---|---|---|
| Arg | Lys | Gln | Pro | Val | Lys | Val | Val | Tyr | Ser | Ser | Lys | Asp | Pro | Ala | Gln | |
| 270 | | | | | 275 | | | | | 280 | | | | | | |

| CCG | AAA | GAG | AGT | TCC | AAG | GTG | GAT | GCG | AAT | GAG | GAG | GTG | GAG | GCT | TTG | 1095 |
|---|---|---|---|---|---|---|---|---|---|---|---|---|---|---|---|---|
| Pro | Lys | Glu | Ser | Ser | Lys | Val | Asp | Ala | Asn | Glu | Glu | Val | Glu | Ala | Leu | |
| 285 | | | | | 290 | | | | | 295 | | | | | 300 | |

| ATC | GTC | AAG | TCC | CCA | CAG | AAG | GAG | TGG | AAC | CCC | TCT | CTG | TTT | AAG | GTG | 1143 |
|---|---|---|---|---|---|---|---|---|---|---|---|---|---|---|---|---|
| Ile | Val | Lys | Ser | Pro | Gln | Lys | Glu | Trp | Asn | Pro | Ser | Leu | Phe | Lys | Val | |
| | | | | 305 | | | | | 310 | | | | | 315 | | |

| TTA | TAC | AAG | ACC | TTT | GGG | CCC | TAC | TTC | CTC | ATG | AGC | TTC | TTC | TTC | AAG | 1191 |
|---|---|---|---|---|---|---|---|---|---|---|---|---|---|---|---|---|
| Leu | Tyr | Lys | Thr | Phe | Gly | Pro | Tyr | Phe | Leu | Met | Ser | Phe | Phe | Phe | Lys | |
| | | | 320 | | | | | 325 | | | | | 330 | | | |

| GCC | ATC | CAC | GAC | CTG | ATG | ATG | TTT | TCC | GGG | CCG | CAG | ATC | TTA | AAG | TTG | 1239 |
|---|---|---|---|---|---|---|---|---|---|---|---|---|---|---|---|---|

| | | | | | | | | | | | | | | | |
|---|---|---|---|---|---|---|---|---|---|---|---|---|---|---|---|
| Ala | Ile | His 335 | Asp | Leu | Met | Met | Phe 340 | Ser | Gly | Pro | Gln | Ile Lys Leu 345 | | | |
| CTC | ATC | AAG | TTC | GTG | AAT | GAC | ACG | AAG | GCC | CCA | GAC | TGG | CAG | GGC TAC | 1287 |
| Leu | Ile 350 | Lys | Phe | Val | Asn | Asp 355 | Thr | Lys | Ala | Pro | Asp 360 | Trp | Gln | Gly Tyr | |
| TTC | TAC | ACC | GTG | CTG | CTG | TTT | GTC | ACT | GCC | TGC | CTG | CAG | ACC | CTC GTG | 1335 |
| Phe 365 | Tyr | Thr | Val | Leu 370 | Leu | Phe | Val | Thr | Ala 375 | Cys | Leu | Gln | Thr | Leu Val 380 | |
| CTG | CAC | CAG | TAC | TTC | CAC | ATC | TGC | TTC | GTC | AGT | GGC | ATG | AGG | ATC AAG | 1383 |
| Leu | His | Gln | Tyr | Phe 385 | His | Ile | Cys | Phe | Val 390 | Ser | Gly | Met | Arg | Ile Lys 395 | |
| ACC | GCT | GTC | ATT | GGG | GCT | GTC | TAT | CGG | AAG | GCC | CTG | GTG | ATC | ACC AAT | 1431 |
| Thr | Ala | Val | Ile 400 | Gly | Ala | Val | Tyr | Arg 405 | Lys | Ala | Leu | Val | Ile 410 | Thr Asn | |
| TCA | GCC | AGA | AAA | TCC | TCC | ACG | GTC | GGG | GAG | ATT | GTC | AAC | CTC | ATG TCT | 1479 |
| Ser | Ala | Arg 415 | Lys | Ser | Ser | Thr | Val 420 | Gly | Glu | Ile | Val | Asn 425 | Leu | Met Ser | |
| GTG | GAC | GCT | CAG | AGG | TTC | ATG | GAC | TTG | GCC | ACG | TAC | ATT | AAC | ATG ATC | 1527 |
| Val | Asp 430 | Ala | Gln | Arg | Phe | Met 435 | Asp | Leu | Ala | Thr | Tyr 440 | Ile | Asn | Met Ile | |
| TGG | TCA | GCC | CCC | CTG | CAA | GTC | ATC | CTT | GCT | CTC | TAC | CTC | CTG | TGG CTG | 1575 |
| Trp 445 | Ser | Ala | Pro | Leu | Gln 450 | Val | Ile | Leu | Ala | Leu 455 | Tyr | Leu | Leu | Trp Leu 460 | |
| AAT | CTG | GGC | CCT | TCC | GTC | CTG | GCT | GGA | GTG | GCG | GTG | ATG | GTC | CTC ATG | 1623 |
| Asn | Leu | Gly | Pro | Ser 465 | Val | Leu | Ala | Gly | Val 470 | Ala | Val | Met | Val | Leu Met 475 | |
| GTG | CCC | GTC | AAT | GCT | GTG | ATG | GCG | ATG | AAG | ACC | AAG | ACG | TAT | CAG GTG | 1671 |
| Val | Pro | Val | Asn 480 | Ala | Val | Met | Ala | Met 485 | Lys | Thr | Lys | Thr | Tyr 490 | Gln Val | |
| GCC | CAC | ATG | AAG | AGC | AAA | GAC | AAT | CGG | ATC | AAG | CTG | ATG | AAC | GAA ATT | 1719 |
| Ala | His | Met 495 | Lys | Ser | Lys | Asp | Asn 500 | Arg | Ile | Lys | Leu | Met 505 | Asn | Glu Ile | |
| CTC | AAT | GGG | ATC | AAA | GTG | CTA | AAG | CTT | TAT | GCC | TGG | GAG | CTG | GCA TTC | 1767 |
| Leu | Asn | Gly | Ile 510 | Lys | Val | Leu | Lys 515 | Leu | Tyr | Ala | Trp | Glu 520 | Leu | Ala Phe | |
| AAG | GAC | AAG | GTG | CTG | GCC | ATC | AGG | CAG | GAG | GAG | CTG | AAG | GTG | CTG AAG | 1815 |
| Lys 525 | Asp | Lys | Val | Leu | Ala 530 | Ile | Arg | Gln | Glu | Glu 535 | Leu | Lys | Val | Leu Lys 540 | |
| AAG | TCT | GCC | TAC | CTG | TCA | GCC | GTG | GGC | ACC | TTC | ACC | TGG | GTC | TGC ACG | 1863 |
| Lys | Ser | Ala | Tyr | Leu 545 | Ser | Ala | Val | Gly | Thr 550 | Phe | Thr | Trp | Val | Cys Thr 555 | |
| CCC | TTT | CTG | GTG | GCC | TTG | TGC | ACA | TTT | GCC | GTC | TAC | GTG | ACC | ATT GAC | 1911 |
| Pro | Phe | Leu | Val 560 | Ala | Leu | Cys | Thr | Phe 565 | Ala | Val | Tyr | Val | Thr 570 | Ile Asp | |
| GAG | AAC | AAC | ATC | CTG | GAT | GCC | CAG | ACA | GCC | TTC | GTG | TCT | TTG | GCC TTG | 1959 |
| Glu | Asn | Asn 575 | Ile | Leu | Asp | Ala | Gln 580 | Thr | Ala | Phe | Val | Ser 585 | Leu | Ala Leu | |
| TTC | AAC | ATC | CTC | CGG | TTT | CCC | CTG | AAC | ATT | CTC | CCC | ATG | GTC | ATC AGC | 2007 |
| Phe | Asn | Ile | Leu 590 | Arg | Phe | Pro | Leu | Asn 595 | Ile | Leu | Pro | Met 600 | Val | Ile Ser | |
| AGC | ATC | GTG | CAG | GCG | AGT | GTC | TCC | CTC | AAA | CGC | CTG | AGG | ATC | TTT CTC | 2055 |
| Ser | Ile | Val | Gln | Ala 610 | Ser | Val | Ser | Leu | Lys 615 | Arg | Leu | Arg | Ile | Phe Leu 620 | |
| | | | | | | | | | | | | | | | |
| Ser 605 | | | | | | | | | | | | | | | |
| TCC | CAT | GAG | GAG | CTG | GAA | CCT | GAC | AGC | ATC | GAG | CGA | CGG | CCT | GTC AAA | 2103 |
| Ser | His | Glu | Glu | Leu 625 | Glu | Pro | Asp | Ser | Ile 630 | Glu | Arg | Arg | Pro | Val Lys 635 | |
| GAC | GGC | GGG | GGC | ACG | AAC | AGC | ATC | ACC | GTG | AGG | AAT | GCC | ACA | TTC ACC | 2151 |
| Asp | Gly | Gly | Gly 640 | Thr | Asn | Ser | Ile | Thr 645 | Val | Arg | Asn | Ala | Thr 650 | Phe Thr | |
| TGG | GCC | AGG | AGC | GAC | CCT | CCC | ACA | CTG | AAT | GGC | ATC | ACC | TTC | TCC ATC | 2199 |

```
                Trp  Ala  Arg  Ser  Asp  Pro  Pro  Thr  Leu  Asn  Gly  Ile  Thr  Phe  Ser  Ile
                          655                      660                     665

CCC  GAA  GGT  GCT  TTG  GTG  GCC  GTG  GTG  GGC  CAG  GTG  GGC  TGC  GGA  AAG                2247
Pro  Glu  Gly  Ala  Leu  Val  Ala  Val  Val  Gly  Gln  Val  Gly  Cys  Gly  Lys
     670                      675                      680

TCG  TCC  CTG  CTC  TCA  GCC  CTC  TTG  GCT  GAG  ATG  GAC  AAA  GTG  GAG  GGG                2295
Ser  Ser  Leu  Leu  Ser  Ala  Leu  Leu  Ala  Glu  Met  Asp  Lys  Val  Glu  Gly
685                      690                      695                      700

CAC  GTG  GCT  ATC  AAG  GGC  TCC  GTG  GCC  TAT  GTG  CCA  CAG  CAG  GCC  TGG                2343
His  Val  Ala  Ile  Lys  Gly  Ser  Val  Ala  Tyr  Val  Pro  Gln  Gln  Ala  Trp
                    705                      710                      715

ATT  CAG  AAT  GAT  TCT  CTC  CGA  GAA  AAC  ATC  CTT  TTT  GGA  TGT  CAG  CTG                2391
Ile  Gln  Asn  Asp  Ser  Leu  Arg  Glu  Asn  Ile  Leu  Phe  Gly  Cys  Gln  Leu
               720                      725                      730

GAG  GAA  CCA  TAT  TAC  AGG  TCC  GTG  ATA  CAG  GCC  TGT  GCC  CTC  CTC  CCA                2439
Glu  Glu  Pro  Tyr  Tyr  Arg  Ser  Val  Ile  Gln  Ala  Cys  Ala  Leu  Leu  Pro
          735                      740                      745

GAC  CTG  GAA  ATC  CTG  CCC  AGT  GGG  GAT  CGG  ACA  GAG  ATT  GGC  GAG  AAG                2487
Asp  Leu  Glu  Ile  Leu  Pro  Ser  Gly  Asp  Arg  Thr  Glu  Ile  Gly  Glu  Lys
     750                      755                      760

GGC  GTG  AAC  CTG  TCT  GGG  GGA  CAG  AAG  CAG  CGC  GTG  AGC  CTG  GCC  CGG                2535
Gly  Val  Asn  Leu  Ser  Gly  Gly  Gln  Lys  Gln  Arg  Val  Ser  Leu  Ala  Arg
765                      770                      775                      780

GCC  GTG  TAC  TCC  AAC  GCT  GAC  ATT  TAC  CTC  TTC  GAT  GAT  CCC  CTC  TCA                2583
Ala  Val  Tyr  Ser  Asn  Ala  Asp  Ile  Tyr  Leu  Phe  Asp  Asp  Pro  Leu  Ser
                    785                      790                      795

GCA  GTG  GAT  GCC  CAT  GTG  GGA  AAA  CAC  ATC  TTT  GAA  AAT  GTG  ATT  GGC                2631
Ala  Val  Asp  Ala  His  Val  Gly  Lys  His  Ile  Phe  Glu  Asn  Val  Ile  Gly
               800                      805                      810

CCC  AAG  GGG  ATG  CTG  AAG  AAC  AAG  ACG  CGG  ATC  TTG  GTC  ACG  CAC  AGC                2679
Pro  Lys  Gly  Met  Leu  Lys  Asn  Lys  Thr  Arg  Ile  Leu  Val  Thr  His  Ser
          815                      820                      825

ATG  AGC  TAC  TTG  CCG  CAG  GTG  GAC  GTC  ATC  ATC  GTC  ATG  AGT  GGC  GGC                2727
Met  Ser  Tyr  Leu  Pro  Gln  Val  Asp  Val  Ile  Ile  Val  Met  Ser  Gly  Gly
     830                      835                      840

AAG  ATC  TCT  GAG  ATG  GGC  TCC  TAC  CAG  GAG  CTG  CTG  GCT  CGA  GAC  GGC                2775
Lys  Ile  Ser  Glu  Met  Gly  Ser  Tyr  Gln  Glu  Leu  Leu  Ala  Arg  Asp  Gly
845                      850                      855                      860

GCC  TTC  GCT  GAG  TTC  CTG  CGT  ACC  TAT  GCC  AGC  ACA  GAG  CAG  GAG  CAG                2823
Ala  Phe  Ala  Glu  Phe  Leu  Arg  Thr  Tyr  Ala  Ser  Thr  Glu  Gln  Glu  Gln
                    865                      870                      875

GAT  GCA  GAG  GAG  AAC  GGG  GTC  ACG  GGC  GTC  AGC  GGT  CCA  GGG  AAG  GAA                2871
Asp  Ala  Glu  Glu  Asn  Gly  Val  Thr  Gly  Val  Ser  Gly  Pro  Gly  Lys  Glu
               880                      885                      890

GCA  AAG  CAA  ATG  GAG  AAT  GGC  ATG  CTG  GTG  ACG  GAC  AGT  GCA  GGG  AAG                2919
Ala  Lys  Gln  Met  Glu  Asn  Gly  Met  Leu  Val  Thr  Asp  Ser  Ala  Gly  Lys
          895                      900                      905

CAA  CTG  CAG  AGA  CAG  CTC  AGC  AGC  TCC  TCC  TCC  TAT  AGT  GGG  GAC  ATC                2967
Gln  Leu  Gln  Arg  Gln  Leu  Ser  Ser  Ser  Ser  Ser  Tyr  Ser  Gly  Asp  Ile
     910                      915                      920

AGC  AGG  CAC  CAC  AAC  AGC  ACC  GCA  GAA  CTG  CAG  AAA  GCT  GAG  GCC  AAG                3015
Ser  Arg  His  His  Asn  Ser  Thr  Ala  Glu  Leu  Gln  Lys  Ala  Glu  Ala  Lys
925                      930                      935                      940

AAG  GAG  GAG  ACC  TGG  AAG  CTG  ATG  GAG  GCT  GAC  AAG  GCG  CAG  ACA  GGG                3063
Lys  Glu  Glu  Thr  Trp  Lys  Leu  Met  Glu  Ala  Asp  Lys  Ala  Gln  Thr  Gly
                    945                      950                      955

CAG  GTC  AAG  CTT  TCC  GTG  TAC  TGG  GAC  TAC  ATG  AAG  GCC  ATC  GGA  CTC                3111
Gln  Val  Lys  Leu  Ser  Val  Tyr  Trp  Asp  Tyr  Met  Lys  Ala  Ile  Gly  Leu
               960                      965                      970

TTC  ATC  TCC  TTC  CTC  AGC  ATC  TTC  CTT  TTC  ATG  TGT  AAC  CAT  GTG  TCC                3159
```

|  |  |  |  |  |  |  |  |  |  |  |  |  |  |  |  |  |
|---|---|---|---|---|---|---|---|---|---|---|---|---|---|---|---|---|
| Phe | Ile | Ser 975 | Phe | Leu | Ser | Ile | Phe 980 | Leu | Phe | Met | Cys | Asn | His 985 | Val | Ser | |

| GCG | CTG | GCT | TCC | AAC | TAT | TGG | CTC | AGC | CTC | TGG | ACT | GAT | GAC | CCC | ATC | 3207 |
|---|---|---|---|---|---|---|---|---|---|---|---|---|---|---|---|---|
| Ala | Leu 990 | Ala | Ser | Asn | Tyr | Trp 995 | Leu | Ser | Leu | Trp | Thr 1000 | Asp | Asp | Pro | Ile | |

| GTC | AAC | GGG | ACT | CAG | GAG | CAC | ACG | AAA | GTC | CGG | CTG | AGC | GTC | TAT | GGA | 3255 |
|---|---|---|---|---|---|---|---|---|---|---|---|---|---|---|---|---|
| Val | Asn 1005 | Gly | Thr | Gln | Glu 1010 | His | Thr | Lys | Val 1015 | Arg | Leu | Ser | Val | Tyr 1020 | Gly | |

| GCC | CTG | GGC | ATT | TCA | CAA | GGG | ATC | GCC | GTG | TTT | GGC | TAC | TCC | ATG | GCC | 3303 |
|---|---|---|---|---|---|---|---|---|---|---|---|---|---|---|---|---|
| Ala | Leu | Gly | Ile | Ser 1025 | Gln | Gly | Ile | Ala | Val 1030 | Phe | Gly | Tyr | Ser | Met 1035 | Ala | |

| GTG | TCC | ATC | GGG | GGG | ATC | TTG | GCT | TCC | CGC | TGT | CTG | CAC | GTG | GAC | CTG | 3351 |
|---|---|---|---|---|---|---|---|---|---|---|---|---|---|---|---|---|
| Val | Ser | Ile | Gly 1040 | Gly | Ile | Leu | Ala | Ser 1045 | Arg | Cys | Leu | His | Val 1050 | Asp | Leu | |

| CTG | CAC | AGC | ATC | CTG | CGG | TCA | CCC | ATG | AGC | TTC | TTT | GAG | CGG | ACC | CCC | 3399 |
|---|---|---|---|---|---|---|---|---|---|---|---|---|---|---|---|---|
| Leu | His | Ser 1055 | Ile | Leu | Arg | Ser | Pro 1060 | Met | Ser | Phe | Phe | Glu 1065 | Arg | Thr | Pro | |

| AGT | GGG | AAC | CTG | GTG | AAC | CGC | TTC | TCC | AAG | GAG | CTG | GAC | ACA | GTG | GAC | 3447 |
|---|---|---|---|---|---|---|---|---|---|---|---|---|---|---|---|---|
| Ser | Gly | Asn 1070 | Leu | Val | Asn | Arg | Phe 1075 | Ser | Lys | Glu | Leu | Asp 1080 | Thr | Val | Asp | |

| TCC | ATG | ATC | CCG | GAG | GTC | ATC | AAG | ATG | TTC | ATG | GGC | TCC | CTG | TTC | AAC | 3495 |
|---|---|---|---|---|---|---|---|---|---|---|---|---|---|---|---|---|
| Ser | Met 1085 | Ile | Pro | Glu | Val 1090 | Ile | Lys | Met | Phe | Met 1095 | Gly | Ser | Leu | Phe | Asn 1100 | |

| GTC | ATT | GGT | GCC | TGC | ATC | GTT | ATC | CTG | CTG | GCC | ACG | CCC | ATC | GCC | GCC | 3543 |
|---|---|---|---|---|---|---|---|---|---|---|---|---|---|---|---|---|
| Val | Ile | Gly | Ala | Cys 1105 | Ile | Val | Ile | Leu | Leu 1110 | Ala | Thr | Pro | Ile | Ala 1115 | Ala | |

| ATC | ATC | ATC | CCG | CCC | CTT | GGC | CTC | ATC | TAC | TTC | TTC | GTC | CAG | AGG | TTC | 3591 |
|---|---|---|---|---|---|---|---|---|---|---|---|---|---|---|---|---|
| Ile | Ile | Ile | Pro 1120 | Pro | Leu | Gly | Leu | Ile 1125 | Tyr | Phe | Phe | Val | Gln 1130 | Arg | Phe | |

| TAC | GTG | GCT | TCC | TCC | CGG | CAG | CTG | AAG | CGC | CTC | GAG | TCG | GTC | AGC | CGC | 3639 |
|---|---|---|---|---|---|---|---|---|---|---|---|---|---|---|---|---|
| Tyr | Val | Ala | Ser | Ser 1135 | Arg | Gln | Leu | Lys | Arg 1140 | Leu | Glu | Ser | Val | Ser 1145 | Arg | |

| TCC | CCG | GTC | TAT | TCC | CAT | TTC | AAC | GAG | ACC | TTG | CTG | GGG | GTC | AGC | GTC | 3687 |
|---|---|---|---|---|---|---|---|---|---|---|---|---|---|---|---|---|
| Ser | Pro | Val | Tyr 1150 | Ser | His | Phe | Asn | Glu 1155 | Thr | Leu | Leu | Gly | Val 1160 | Ser | Val | |

| ATT | CGA | GCC | TTC | GAG | GAG | CAG | GAG | CGC | TTC | ATC | CAC | CAG | AGT | GAC | CTG | 3735 |
|---|---|---|---|---|---|---|---|---|---|---|---|---|---|---|---|---|
| Ile | Arg 1165 | Ala | Phe | Glu | Glu 1170 | Gln | Glu | Arg | Phe | Ile 1175 | His | Gln | Ser | Asp | Leu 1180 | |

| AAG | GTG | GAC | GAG | AAC | CAG | AAG | GCC | TAT | TAC | CCC | AGC | ATC | GTG | GCC | AAC | 3783 |
|---|---|---|---|---|---|---|---|---|---|---|---|---|---|---|---|---|
| Lys | Val | Asp | Glu | Asn 1185 | Gln | Lys | Ala | Tyr | Tyr 1190 | Pro | Ser | Ile | Val | Ala 1195 | Asn | |

| AGG | TGG | CTG | GCC | GTG | CGG | CTG | GAG | TGT | GTG | GGC | AAC | TGC | ATC | GTT | CTG | 3831 |
|---|---|---|---|---|---|---|---|---|---|---|---|---|---|---|---|---|
| Arg | Trp | Leu | Ala 1200 | Val | Arg | Leu | Glu | Cys 1205 | Val | Gly | Asn | Cys | Ile 1210 | Val | Leu | |

| TTT | GCT | GCC | CTG | TTT | GCG | GTG | ATC | TCC | AGG | CAC | AGC | CTC | AGT | GCT | GGC | 3879 |
|---|---|---|---|---|---|---|---|---|---|---|---|---|---|---|---|---|
| Phe | Ala | Ala | Leu 1215 | Phe | Ala | Val | Ile | Ser 1220 | Arg | His | Ser | Leu | Ser 1225 | Ala | Gly | |

| TTG | GTG | GGC | CTC | TCA | GTG | TCT | TAC | TCA | TTG | CAG | GTC | ACC | ACG | TAC | TTG | 3927 |
|---|---|---|---|---|---|---|---|---|---|---|---|---|---|---|---|---|
| Leu | Val 1230 | Gly | Leu | Ser | Val | Ser 1235 | Tyr | Ser | Leu | Gln | Val 1240 | Thr | Thr | Tyr | Leu | |

| AAC | TGG | CTG | GTT | CGG | ATG | TCA | TCT | GAA | ATG | GAA | ACC | AAC | ATC | GTG | GCC | 3975 |
|---|---|---|---|---|---|---|---|---|---|---|---|---|---|---|---|---|
| Asn | Trp | Leu | Val 1245 | Arg | Met | Ser | Ser | Glu 1250 | Met | Glu | Thr | Asn | Ile 1255 | Val | Ala 1260 | |

| GTG | GAG | AGG | CTC | AAG | GAG | TAT | TCA | GAG | ACT | GAG | AAG | GAG | GCG | CCC | TGG | 4023 |
|---|---|---|---|---|---|---|---|---|---|---|---|---|---|---|---|---|
| Val | Glu | Arg | Leu | Lys | Glu 1265 | Tyr | Ser | Glu | Thr | Glu 1270 | Lys | Glu | Ala | Pro | Trp 1275 | |

| CAA | ATC | CAG | GAG | ACA | GCT | CCG | CCC | AGC | AGC | TGG | CCC | CAG | GTG | GGC | CGA | 4071 |
|---|---|---|---|---|---|---|---|---|---|---|---|---|---|---|---|---|
| Gln | Ile | Gln | Glu | Thr 1280 | Ala | Pro | Pro | Ser | Ser 1285 | Trp | Pro | Gln | Val | Gly 1290 | Arg | |

| GTG | GAA | TTC | CGG | AAC | TAC | TGC | CTG | CGC | TAC | CGA | GAG | GAC | CTG | GAC | TTC | 4119 |

| | | | | | | | | | | | | | | | | |
|---|---|---|---|---|---|---|---|---|---|---|---|---|---|---|---|---|
| Val | Glu | Phe | Arg | Asn | Tyr | Cys | Leu | Arg | Tyr | Arg | Glu | Asp | Leu | Asp | Phe | |
| | | 1295 | | | | | 1300 | | | | 1305 | | | | | |
| GTT | CTC | AGG | CAC | ATC | AAT | GTC | ACG | ATC | AAT | GGG | GGA | GAA | AAG | GTC | GGC | 4167 |
| Val | Leu | Arg | His | Ile | Asn | Val | Thr | Ile | Asn | Gly | Gly | Glu | Lys | Val | Gly | |
| | 1310 | | | | | 1315 | | | | | 1320 | | | | | |
| ATC | GTG | GGG | CGG | ACG | GGA | GCT | GGG | AAG | TCG | TCC | CTG | ACC | CTG | GGC | TTA | 4215 |
| Ile | Val | Gly | Arg | Thr | Gly | Ala | Gly | Lys | Ser | Ser | Leu | Thr | Leu | Gly | Leu | |
| 1325 | | | | | 1330 | | | | | 1335 | | | | | 1340 | |
| TTT | CGG | ATC | AAC | GAG | TCT | GCC | GAA | GGA | GAG | ATC | ATC | ATC | GAT | GGC | ATC | 4263 |
| Phe | Arg | Ile | Asn | Glu | Ser | Ala | Glu | Gly | Glu | Ile | Ile | Ile | Asp | Gly | Ile | |
| | | | | | 1345 | | | | | 1350 | | | | | 1355 | |
| AAC | ATC | GCC | AAG | ATC | GGC | CTG | CAC | GAC | CTC | CGC | TTC | AAG | ATC | ACC | ATC | 4311 |
| Asn | Ile | Ala | Lys | Ile | Gly | Leu | His | Asp | Leu | Arg | Phe | Lys | Ile | Thr | Ile | |
| | | | 1360 | | | | | 1365 | | | | | 1370 | | | |
| ATC | CCC | CAG | GAC | CCT | GTT | TTG | TTT | TCG | GGT | TCC | CTC | CGA | ATG | AAC | CTG | 4359 |
| Ile | Pro | Gln | Asp | Pro | Val | Leu | Phe | Ser | Gly | Ser | Leu | Arg | Met | Asn | Leu | |
| | | | | 1375 | | | | | 1380 | | | | | 1385 | | |
| GAC | CCA | TTC | AGC | CAG | TAC | TCG | GAT | GAA | GAA | GTC | TGG | ACG | TCC | CTG | GAG | 4407 |
| Asp | Pro | Phe | Ser | Gln | Tyr | Ser | Asp | Glu | Glu | Val | Trp | Thr | Ser | Leu | Glu | |
| | | | 1390 | | | | | 1395 | | | | | 1400 | | | |
| CTG | GCC | CAC | CTG | AAG | GAC | TTC | GTG | TCA | GCC | CTT | CCT | GAC | AAG | CTA | GAC | 4455 |
| Leu | Ala | His | Leu | Lys | Asp | Phe | Val | Ser | Ala | Leu | Pro | Asp | Lys | Leu | Asp | |
| 1405 | | | | | 1410 | | | | | 1415 | | | | | 1420 | |
| CAT | GAA | TGT | GCA | GAA | GGC | GGG | GAG | AAC | CTC | AGT | GTC | GGG | CAG | CGC | CAG | 4503 |
| His | Glu | Cys | Ala | Glu | Gly | Gly | Glu | Asn | Leu | Ser | Val | Gly | Gln | Arg | Gln | |
| | | | | 1425 | | | | | 1430 | | | | | 1435 | | |
| CTT | GTG | TGC | CTA | GCC | CGG | GCC | CTG | CTG | AGG | AAG | ACG | AAG | ATC | CTT | GTG | 4551 |
| Leu | Val | Cys | Leu | Ala | Arg | Ala | Leu | Leu | Arg | Lys | Thr | Lys | Ile | Leu | Val | |
| | | | 1440 | | | | | 1445 | | | | | 1450 | | | |
| TTG | GAT | GAG | GCC | ACG | GCA | GCC | GTG | GAC | CTG | GAA | ACG | GAC | GAC | CTC | ATC | 4599 |
| Leu | Asp | Glu | Ala | Thr | Ala | Ala | Val | Asp | Leu | Glu | Thr | Asp | Asp | Leu | Ile | |
| | | | 1455 | | | | | 1460 | | | | | 1465 | | | |
| CAG | TCC | ACC | ATC | CGG | ACA | CAG | TTC | GAG | GAC | TGC | ACC | GTC | CTC | ACC | ATC | 4647 |
| Gln | Ser | Thr | Ile | Arg | Thr | Gln | Phe | Glu | Asp | Cys | Thr | Val | Leu | Thr | Ile | |
| | | 1470 | | | | | 1475 | | | | | 1480 | | | | |
| GCC | CAC | CGG | CTC | AAC | ACC | ATC | ATG | GAC | TAC | ACA | AGG | GTG | ATC | GTC | TTG | 4695 |
| Ala | His | Arg | Leu | Asn | Thr | Ile | Met | Asp | Tyr | Thr | Arg | Val | Ile | Val | Leu | |
| 1485 | | | | | 1490 | | | | | 1495 | | | | | 1500 | |
| GAC | AAA | GGA | GAA | ATC | CAG | GAG | TAC | GGC | GCC | CCA | TCG | GAC | CTC | CTG | CAG | 4743 |
| Asp | Lys | Gly | Glu | Ile | Gln | Glu | Tyr | Gly | Ala | Pro | Ser | Asp | Leu | Leu | Gln | |
| | | | | 1505 | | | | | 1510 | | | | | 1515 | | |
| CAG | AGA | GGT | CTT | TTC | TAC | AGC | ATG | GCC | AAA | GAC | GCC | GGC | TTG | GTG | | 4788 |
| Gln | Arg | Gly | Leu | Phe | Tyr | Ser | Met | Ala | Lys | Asp | Ala | Gly | Leu | Val | | |
| | | | 1520 | | | | | 1525 | | | | | 1530 | | | |

```
TGAGCCCAG   AGCTGGCATA   TCTGGTCAGA   ACTGCAGGGC   CTATATGCCA   GCGCCCCAGG    4848

GAGGAGTCAG   TACCCCTGGT   AAACCAAGCC   TCCCACACTG   AAACCAAAAC   ATAAAAACCA    4908

AACCCAGACA   ACCAAAACAT   ATTCAAAGCA   GCAGCCACCG   CCATCCGGTC   CCCTGCCTGG    4968

AACTGGCTGT   GAAGACCCAG   GAGAGACAGA   GATGCGAACC   ACC                       5011
```

( 2 ) INFORMATION FOR SEQ ID NO:4:

( i ) SEQUENCE CHARACTERISTICS:
        ( A ) LENGTH: 1531 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met  Ala  Leu  Arg  Gly  Phe  Cys  Ser  Ala  Asp  Gly  Ser  Asp  Pro  Leu  Trp

-continued

```
  1                   5                      10                    15

Asp   Trp   Asn   Val   Thr   Trp   Asn   Thr   Ser   Asn   Pro   Asp   Phe   Thr   Lys   Cys
                   20                      25                      30

Phe   Gln   Asn   Thr   Val   Leu   Val   Trp   Val   Pro   Cys   Phe   Tyr   Leu   Trp   Ala
             35                      40                      45

Cys   Phe   Pro   Phe   Tyr   Phe   Leu   Tyr   Leu   Ser   Arg   His   Asp   Arg   Gly   Tyr
       50                            55                      60

Ile   Gln   Met   Thr   Pro   Leu   Asn   Lys   Thr   Lys   Thr   Ala   Leu   Gly   Phe   Leu
 65                     70                      75                                        80

Leu   Trp   Ile   Val   Cys   Trp   Ala   Asp   Leu   Phe   Tyr   Ser   Phe   Trp   Glu   Arg
                         85                      90                            95

Ser   Arg   Gly   Ile   Phe   Leu   Ala   Pro   Val   Phe   Leu   Val   Ser   Pro   Thr   Leu
                  100                     105                     110

Leu   Gly   Ile   Thr   Thr   Leu   Leu   Ala   Thr   Phe   Leu   Ile   Gln   Leu   Glu   Arg
            115                     120                     125

Arg   Lys   Gly   Val   Gln   Ser   Ser   Gly   Ile   Met   Leu   Thr   Phe   Trp   Leu   Val
      130                     135                     140

Ala   Leu   Val   Cys   Ala   Leu   Ala   Ile   Leu   Arg   Ser   Lys   Ile   Met   Thr   Ala
145                           150                     155                                 160

Leu   Lys   Glu   Asp   Ala   Gln   Val   Asp   Leu   Phe   Arg   Asp   Ile   Thr   Phe   Tyr
                        165                     170                     175

Val   Tyr   Phe   Ser   Leu   Leu   Leu   Ile   Gln   Leu   Val   Leu   Ser   Cys   Phe   Ser
                  180                     185                     190

Asp   Arg   Ser   Pro   Leu   Phe   Ser   Glu   Thr   Ile   His   Asp   Pro   Asn   Pro   Cys
            195                     200                     205

Pro   Glu   Ser   Ser   Ala   Ser   Phe   Leu   Ser   Arg   Ile   Thr   Phe   Trp   Trp   Ile
      210                     215                     220

Thr   Gly   Leu   Ile   Val   Arg   Gly   Tyr   Arg   Gln   Pro   Leu   Glu   Gly   Ser   Asp
225                           230                     235                                 240

Leu   Trp   Ser   Leu   Asn   Lys   Glu   Asp   Thr   Ser   Glu   Gln   Val   Val   Pro   Val
                  245                     250                     255

Leu   Val   Lys   Asn   Trp   Lys   Lys   Glu   Cys   Ala   Lys   Thr   Arg   Lys   Gln   Pro
                  260                     265                     270

Val   Lys   Val   Val   Tyr   Ser   Ser   Lys   Asp   Pro   Ala   Gln   Pro   Lys   Glu   Ser
            275                     280                     285

Ser   Lys   Val   Asp   Ala   Asn   Glu   Glu   Val   Glu   Ala   Leu   Ile   Val   Lys   Ser
      290                     295                     300

Pro   Gln   Lys   Glu   Trp   Asn   Pro   Ser   Leu   Phe   Lys   Val   Leu   Tyr   Lys   Thr
305                           310                     315                                 320

Phe   Gly   Pro   Tyr   Phe   Leu   Met   Ser   Phe   Phe   Phe   Lys   Ala   Ile   His   Asp
                  325                     330                     335

Leu   Met   Met   Phe   Ser   Gly   Pro   Gln   Ile   Leu   Lys   Leu   Leu   Ile   Lys   Phe
                  340                     345                     350

Val   Asn   Asp   Thr   Lys   Ala   Pro   Asp   Trp   Gln   Gly   Tyr   Phe   Tyr   Thr   Val
            355                     360                     365

Leu   Leu   Phe   Val   Thr   Ala   Cys   Leu   Gln   Thr   Leu   Val   Leu   His   Gln   Tyr
      370                     375                     380

Phe   His   Ile   Cys   Phe   Val   Ser   Gly   Met   Arg   Ile   Lys   Thr   Ala   Val   Ile
385                           390                     395                                 400

Gly   Ala   Val   Tyr   Arg   Lys   Ala   Leu   Val   Ile   Thr   Asn   Ser   Ala   Arg   Lys
                  405                     410                     415

Ser   Ser   Thr   Val   Gly   Glu   Ile   Val   Asn   Leu   Met   Ser   Val   Asp   Ala   Gln
                  420                     425                     430
```

-continued

| | | | | | | | | | | | | | | |
|---|---|---|---|---|---|---|---|---|---|---|---|---|---|---|
| Arg | Phe | Met<br>435 | Asp | Leu | Ala | Thr | Tyr<br>440 | Ile | Asn | Met | Ile | Trp<br>445 | Ser | Ala | Pro |
| Leu | Gln<br>450 | Val | Ile | Leu | Ala | Leu<br>455 | Tyr | Leu | Leu | Trp | Leu<br>460 | Asn | Leu | Gly | Pro |
| Ser<br>465 | Val | Leu | Ala | Gly | Val<br>470 | Ala | Val | Met | Val | Leu<br>475 | Met | Val | Pro | Val | Asn<br>480 |
| Ala | Val | Met | Ala | Met<br>485 | Lys | Thr | Lys | Thr | Tyr<br>490 | Gln | Val | Ala | His | Met<br>495 | Lys |
| Ser | Lys | Asp | Asn<br>500 | Arg | Ile | Lys | Leu | Met<br>505 | Asn | Glu | Ile | Leu | Asn<br>510 | Gly | Ile |
| Lys | Val | Leu<br>515 | Lys | Leu | Tyr | Ala | Trp<br>520 | Glu | Leu | Ala | Phe | Lys<br>525 | Asp | Lys | Val |
| Leu | Ala<br>530 | Ile | Arg | Gln | Glu | Glu<br>535 | Leu | Lys | Val | Leu | Lys<br>540 | Lys | Ser | Ala | Tyr |
| Leu<br>545 | Ser | Ala | Val | Gly | Thr<br>550 | Phe | Thr | Trp | Val | Cys<br>555 | Thr | Pro | Phe | Leu | Val<br>560 |
| Ala | Leu | Cys | Thr | Phe<br>565 | Ala | Val | Tyr | Val | Thr<br>570 | Ile | Asp | Glu | Asn | Asn<br>575 | Ile |
| Leu | Asp | Ala | Gln<br>580 | Thr | Ala | Phe | Val | Ser<br>585 | Leu | Ala | Leu | Phe | Asn<br>590 | Ile | Leu |
| Arg | Phe | Pro<br>595 | Leu | Asn | Ile | Leu | Pro<br>600 | Met | Val | Ile | Ser | Ser<br>605 | Ile | Val | Gln |
| Ala | Ser<br>610 | Val | Ser | Leu | Lys | Arg<br>615 | Leu | Arg | Ile | Phe | Leu<br>620 | Ser | His | Glu | Glu |
| Leu<br>625 | Glu | Pro | Asp | Ser | Ile<br>630 | Glu | Arg | Arg | Pro | Val<br>635 | Lys | Asp | Gly | Gly | Gly<br>640 |
| Thr | Asn | Ser | Ile | Thr<br>645 | Val | Arg | Asn | Ala | Thr<br>650 | Phe | Thr | Trp | Ala | Arg<br>655 | Ser |
| Asp | Pro | Pro | Thr<br>660 | Leu | Asn | Gly | Ile | Thr<br>665 | Phe | Ser | Ile | Pro | Glu<br>670 | Gly | Ala |
| Leu | Val | Ala<br>675 | Val | Val | Gly | Gln | Val<br>680 | Gly | Cys | Gly | Lys | Ser<br>685 | Ser | Leu | Leu |
| Ser | Ala<br>690 | Leu | Leu | Ala | Glu | Met<br>695 | Asp | Lys | Val | Glu | Gly<br>700 | His | Val | Ala | Ile |
| Lys<br>705 | Gly | Ser | Val | Ala | Tyr<br>710 | Val | Pro | Gln | Gln | Ala<br>715 | Trp | Ile | Gln | Asn | Asp<br>720 |
| Ser | Leu | Arg | Glu | Asn<br>725 | Ile | Leu | Phe | Gly | Cys<br>730 | Gln | Leu | Glu | Glu | Pro<br>735 | Tyr |
| Tyr | Arg | Ser | Val<br>740 | Ile | Gln | Ala | Cys<br>745 | Ala | Leu | Leu | Pro | Asp<br>750 | Leu | Glu | Ile |
| Leu | Pro | Ser<br>755 | Gly | Asp | Arg | Thr | Glu<br>760 | Ile | Gly | Glu | Lys | Gly<br>765 | Val | Asn | Leu |
| Ser | Gly<br>770 | Gly | Gln | Lys | Gln | Arg<br>775 | Val | Ser | Leu | Ala | Arg<br>780 | Ala | Val | Tyr | Ser |
| Asn<br>785 | Ala | Asp | Ile | Tyr | Leu<br>790 | Phe | Asp | Asp | Pro | Leu<br>795 | Ser | Ala | Val | Asp | Ala<br>800 |
| His | Val | Gly | Lys | His<br>805 | Ile | Phe | Glu | Asn | Val<br>810 | Ile | Gly | Pro | Lys | Gly<br>815 | Met |
| Leu | Lys | Asn | Lys<br>820 | Thr | Arg | Ile | Leu | Val<br>825 | Thr | His | Ser | Met | Ser<br>830 | Tyr | Leu |
| Pro | Gln | Val<br>835 | Asp | Val | Ile | Ile | Val<br>840 | Met | Ser | Gly | Gly | Lys<br>845 | Ile | Ser | Glu |
| Met | Gly<br>850 | Ser | Tyr | Gln | Glu | Leu<br>855 | Leu | Ala | Arg | Asp | Gly<br>860 | Ala | Phe | Ala | Glu |

```
Phe  Leu  Arg  Thr  Tyr  Ala  Ser  Thr  Glu  Gln  Glu  Gln  Asp  Ala  Glu
865                 870                 875                 880

Asn  Gly  Val  Thr  Gly  Val  Ser  Gly  Pro  Gly  Lys  Glu  Ala  Lys  Gln  Met
                    885                 890                 895

Glu  Asn  Gly  Met  Leu  Val  Thr  Asp  Ser  Ala  Gly  Lys  Gln  Leu  Gln  Arg
               900                 905                 910

Gln  Leu  Ser  Ser  Ser  Ser  Ser  Tyr  Ser  Gly  Asp  Ile  Ser  Arg  His  His
               915                 920                 925

Asn  Ser  Thr  Ala  Glu  Leu  Gln  Lys  Ala  Glu  Ala  Lys  Lys  Glu  Glu  Thr
          930                 935                 940

Trp  Lys  Leu  Met  Glu  Ala  Asp  Lys  Ala  Gln  Thr  Gly  Gln  Val  Lys  Leu
945                 950                 955                 960

Ser  Val  Tyr  Trp  Asp  Tyr  Met  Lys  Ala  Ile  Gly  Leu  Phe  Ile  Ser  Phe
               965                 970                 975

Leu  Ser  Ile  Phe  Leu  Phe  Met  Cys  Asn  His  Val  Ser  Ala  Leu  Ala  Ser
               980                 985                 990

Asn  Tyr  Trp  Leu  Ser  Leu  Trp  Thr  Asp  Asp  Pro  Ile  Val  Asn  Gly  Thr
          995                 1000                1005

Gln  Glu  His  Thr  Lys  Val  Arg  Leu  Ser  Val  Tyr  Gly  Ala  Leu  Gly  Ile
     1010                1015                1020

Ser  Gln  Gly  Ile  Ala  Val  Phe  Gly  Tyr  Ser  Met  Ala  Val  Ser  Ile  Gly
1025                1030                1035                1040

Gly  Ile  Leu  Ala  Ser  Arg  Cys  Leu  His  Val  Asp  Leu  Leu  His  Ser  Ile
               1045                1050                1055

Leu  Arg  Ser  Pro  Met  Ser  Phe  Phe  Glu  Arg  Thr  Pro  Ser  Gly  Asn  Leu
               1060                1065                1070

Val  Asn  Arg  Phe  Ser  Lys  Glu  Leu  Asp  Thr  Val  Asp  Ser  Met  Ile  Pro
          1075                1080                1085

Glu  Val  Ile  Lys  Met  Phe  Met  Gly  Ser  Leu  Phe  Asn  Val  Ile  Gly  Ala
     1090                1095                1100

Cys  Ile  Val  Ile  Leu  Leu  Ala  Thr  Pro  Ile  Ala  Ala  Ile  Ile  Ile  Pro
1105                1110                1115                1120

Pro  Leu  Gly  Leu  Ile  Tyr  Phe  Phe  Val  Gln  Arg  Phe  Tyr  Val  Ala  Ser
               1125                1130                1135

Ser  Arg  Gln  Leu  Lys  Arg  Leu  Glu  Ser  Val  Ser  Arg  Ser  Pro  Val  Tyr
               1140                1145                1150

Ser  His  Phe  Asn  Glu  Thr  Leu  Leu  Gly  Val  Ser  Val  Ile  Arg  Ala  Phe
          1155                1160                1165

Glu  Glu  Gln  Glu  Arg  Phe  Ile  His  Gln  Ser  Asp  Leu  Lys  Val  Asp  Glu
     1170                1175                1180

Asn  Gln  Lys  Ala  Tyr  Tyr  Pro  Ser  Ile  Val  Ala  Asn  Arg  Trp  Leu  Ala
1185                1190                1195                1200

Val  Arg  Leu  Glu  Cys  Val  Gly  Asn  Cys  Ile  Val  Leu  Phe  Ala  Ala  Leu
               1205                1210                1215

Phe  Ala  Val  Ile  Ser  Arg  His  Ser  Leu  Ser  Ala  Gly  Leu  Val  Gly  Leu
               1220                1225                1230

Ser  Val  Ser  Tyr  Ser  Leu  Gln  Val  Thr  Thr  Tyr  Leu  Asn  Trp  Leu  Val
               1235                1240                1245

Arg  Met  Ser  Ser  Glu  Met  Glu  Thr  Asn  Ile  Val  Ala  Val  Glu  Arg  Leu
               1250                1255                1260

Lys  Glu  Tyr  Ser  Glu  Thr  Glu  Lys  Glu  Ala  Pro  Trp  Gln  Ile  Gln  Glu
1265                1270                1275                1280

Thr  Ala  Pro  Pro  Ser  Ser  Trp  Pro  Gln  Val  Gly  Arg  Val  Glu  Phe  Arg
```

|  | 1285 |  |  |  |  | 1290 |  |  |  |  | 1295 |  |  |
|---|---|---|---|---|---|---|---|---|---|---|---|---|---|

Asn Tyr Cys Leu Arg Tyr Arg Glu Asp Leu Asp Phe Val Leu Arg His
              1300                    1305                1310

Ile Asn Val Thr Ile Asn Gly Gly Glu Lys Val Gly Ile Val Gly Arg
          1315                1320                    1325

Thr Gly Ala Gly Lys Ser Ser Leu Thr Leu Gly Leu Phe Arg Ile Asn
      1330                    1335                1340

Glu Ser Ala Glu Gly Glu Ile Ile Ile Asp Gly Ile Asn Ile Ala Lys
1345              1350                    1355                1360

Ile Gly Leu His Asp Leu Arg Phe Lys Ile Thr Ile Ile Pro Gln Asp
              1365                    1370                1375

Pro Val Leu Phe Ser Gly Ser Leu Arg Met Asn Leu Asp Pro Phe Ser
              1380                    1385                1390

Gln Tyr Ser Asp Glu Glu Val Trp Thr Ser Leu Glu Leu Ala His Leu
              1395                    1400                1405

Lys Asp Phe Val Ser Ala Leu Pro Asp Lys Leu Asp His Glu Cys Ala
          1410                1415                    1420

Glu Gly Gly Glu Asn Leu Ser Val Gly Gln Arg Gln Leu Val Cys Leu
1425              1430                    1435                1440

Ala Arg Ala Leu Leu Arg Lys Thr Lys Ile Leu Val Leu Asp Glu Ala
              1445                    1450                1455

Thr Ala Ala Val Asp Leu Glu Thr Asp Asp Leu Ile Gln Ser Thr Ile
              1460                    1465                1470

Arg Thr Gln Phe Glu Asp Cys Thr Val Leu Thr Ile Ala His Arg Leu
          1475                1480                    1485

Asn Thr Ile Met Asp Tyr Thr Arg Val Ile Val Leu Asp Lys Gly Glu
      1490                1495                    1500

Ile Gln Glu Tyr Gly Ala Pro Ser Asp Leu Leu Gln Gln Arg Gly Leu
1505              1510                    1515                1520

Phe Tyr Ser Met Ala Lys Asp Ala Gly Leu Val
              1525                    1530

( 2 ) INFORMATION FOR SEQ ID NO:5:

( i ) SEQUENCE CHARACTERISTICS:
        ( A ) LENGTH: 5889 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 6 4589

( x i ) SEQUENCE DESCRIPTION: SEQ ID NO:5:

```
CCCGC ATG GCG CTG CGC AGC TTC TGC AGC GCT GAT GGC TCC GAT CCA         47
      Met Ala Leu Arg Ser Phe Cys Ser Ala Asp Gly Ser Asp Pro
      1               5                   10

CTC TGG GAC TGG AAT GTC ACA TGG CAC ACC AGC AAC CCC GAC TTT ACC       95
Leu Trp Asp Trp Asn Val Thr Trp His Thr Ser Asn Pro Asp Phe Thr
15              20                  25                  30

AAG TGC TTT CAG AAC ACG GTC CTC ACA TGG GTG CCT TGT TTC TAC CTC      143
Lys Cys Phe Gln Asn Thr Val Leu Thr Trp Val Pro Cys Phe Tyr Leu
                35                  40                  45

TGG TCC TGT TTC CCC CTC TAC TTC TTC TAT CTC TCT CGC CAT GAC CGG      191
Trp Ser Cys Phe Pro Leu Tyr Phe Phe Tyr Leu Ser Arg His Asp Arg
            50                  55                  60
```

| | | | | | | | | | | | | | | | | |
|---|---|---|---|---|---|---|---|---|---|---|---|---|---|---|---|---|
| GGC | TAC | ATC | CAG | ATG | ACA | CAC | CTC | AAC | AAA | ACC | AAA | ACT | GCC | TTA | GGA | 239 |
| Gly | Tyr | Ile | Gln | Met | Thr | His | Leu | Asn | Lys | Thr | Lys | Thr | Ala | Leu | Gly | |
| | | 65 | | | | 70 | | | | | 75 | | | | | |
| TTC | TTT | CTG | TGG | ATC | ATC | TGC | TGG | GCA | GAC | CTC | TTC | TAC | TCT | TTC | TGG | 287 |
| Phe | Phe | Leu | Trp | Ile | Ile | Cys | Trp | Ala | Asp | Leu | Phe | Tyr | Ser | Phe | Trp | |
| | 80 | | | | | 85 | | | | | 90 | | | | | |
| GAA | AGA | AGT | CAG | GGA | GTG | CTC | CGA | GCC | CCG | GTG | TTA | CTG | GTC | AGC | CCA | 335 |
| Glu | Arg | Ser | Gln | Gly | Val | Leu | Arg | Ala | Pro | Val | Leu | Leu | Val | Ser | Pro | |
| 95 | | | | 100 | | | | | 105 | | | | | 110 | | |
| ACA | CTG | CTG | GGC | ATC | ACC | ATG | CTG | CTC | GCC | ACC | TTT | TTG | ATA | CAG | CTT | 383 |
| Thr | Leu | Leu | Gly | Ile | Thr | Met | Leu | Leu | Ala | Thr | Phe | Leu | Ile | Gln | Leu | |
| | | | | 115 | | | | 120 | | | | | 125 | | | |
| GAA | CGG | AGG | AAG | GGA | GTC | CAA | TCC | TCG | GGA | ATT | ATG | CTT | ACT | TTC | TGG | 431 |
| Glu | Arg | Arg | Lys | Gly | Val | Gln | Ser | Ser | Gly | Ile | Met | Leu | Thr | Phe | Trp | |
| | | 130 | | | | | 135 | | | | | 140 | | | | |
| CTC | GTA | GCC | CTA | CTC | TGT | GCC | CTT | GCC | ATC | TTG | AGA | TCT | AAG | ATC | ATC | 479 |
| Leu | Val | Ala | Leu | Leu | Cys | Ala | Leu | Ala | Ile | Leu | Arg | Ser | Lys | Ile | Ile | |
| | | 145 | | | | | 150 | | | | | 155 | | | | |
| TCT | GCC | TTA | AAA | AAG | GAT | GCT | CAT | GTG | GAC | GTG | TTT | CGA | GAT | TCC | ACG | 527 |
| Ser | Ala | Leu | Lys | Lys | Asp | Ala | His | Val | Asp | Val | Phe | Arg | Asp | Ser | Thr | |
| | 160 | | | | | 165 | | | | | 170 | | | | | |
| TTC | TAT | CTG | TAC | TTC | ACC | CTT | GTG | CTT | GTT | CAG | CTC | GTG | CTG | TCC | TGC | 575 |
| Phe | Tyr | Leu | Tyr | Phe | Thr | Leu | Val | Leu | Val | Gln | Leu | Val | Leu | Ser | Cys | |
| 175 | | | | | | 180 | | | | | 185 | | | | 190 | |
| TTC | TCA | GAC | TGC | TCA | CCC | CTG | TTC | TCT | GAA | ACT | GTC | CAT | GAC | CGG | AAT | 623 |
| Phe | Ser | Asp | Cys | Ser | Pro | Leu | Phe | Ser | Glu | Thr | Val | His | Asp | Arg | Asn | |
| | | | | 195 | | | | | 200 | | | | | 205 | | |
| CCA | TGC | CCA | GAA | TCC | AGT | GCC | TCT | TTC | CTT | TCC | AGG | ATT | ACT | TTC | TGG | 671 |
| Pro | Cys | Pro | Glu | Ser | Ser | Ala | Ser | Phe | Leu | Ser | Arg | Ile | Thr | Phe | Trp | |
| | | | 210 | | | | | 215 | | | | | 220 | | | |
| TGG | ATT | ACA | GGG | ATG | ATG | GTG | CAC | GGC | TAC | CGC | CAG | CCC | CTG | GAG | AGC | 719 |
| Trp | Ile | Thr | Gly | Met | Met | Val | His | Gly | Tyr | Arg | Gln | Pro | Leu | Glu | Ser | |
| | | 225 | | | | | 230 | | | | | 235 | | | | |
| AGT | GAC | CTC | TGG | TCA | TTG | AAT | AAG | GAG | GAC | ACA | TCA | GAA | GAA | GTG | GTA | 767 |
| Ser | Asp | Leu | Trp | Ser | Leu | Asn | Lys | Glu | Asp | Thr | Ser | Glu | Glu | Val | Val | |
| | 240 | | | | | 245 | | | | | 250 | | | | | |
| CCT | GTG | CTG | GTG | AAT | AAC | TGG | AAG | AAG | GAA | TGT | GAT | AAG | TCA | AGG | AAG | 815 |
| Pro | Val | Leu | Val | Asn | Asn | Trp | Lys | Lys | Glu | Cys | Asp | Lys | Ser | Arg | Lys | |
| 255 | | | | | 260 | | | | | 265 | | | | | 270 | |
| CAG | CCT | GTA | CGG | ATT | GTG | TAT | GCC | CCT | CCC | AAA | GAT | CCC | AGC | AAG | CCT | 863 |
| Gln | Pro | Val | Arg | Ile | Val | Tyr | Ala | Pro | Pro | Lys | Asp | Pro | Ser | Lys | Pro | |
| | | | | 275 | | | | | 280 | | | | | 285 | | |
| AAG | GGA | AGT | TCC | CAG | TTG | GAT | GTG | AAT | GAG | GAG | GTG | GAG | GCA | CTG | ATT | 911 |
| Lys | Gly | Ser | Ser | Gln | Leu | Asp | Val | Asn | Glu | Glu | Val | Glu | Ala | Leu | Ile | |
| | | | 290 | | | | | 295 | | | | | 300 | | | |
| GTC | AAG | TCA | CCC | CAC | AAG | GAT | CGG | GAG | CCC | TCT | CTG | TTC | AAG | GTG | TTA | 959 |
| Val | Lys | Ser | Pro | His | Lys | Asp | Arg | Glu | Pro | Ser | Leu | Phe | Lys | Val | Leu | |
| | | 305 | | | | | 310 | | | | | 315 | | | | |
| TAC | AAG | ACT | TTT | GGT | CCC | TAC | TTC | CTC | ATG | AGC | TTC | CTG | TAC | AAG | GCC | 1007 |
| Tyr | Lys | Thr | Phe | Gly | Pro | Tyr | Phe | Leu | Met | Ser | Phe | Leu | Tyr | Lys | Ala | |
| | 320 | | | | | 325 | | | | | 330 | | | | | |
| CTT | CAT | GAC | CTG | ATG | ATG | TTT | GCC | GGC | CCC | AAG | ATC | TTG | GAA | TTG | ATT | 1055 |
| Leu | His | Asp | Leu | Met | Met | Phe | Ala | Gly | Pro | Lys | Ile | Leu | Glu | Leu | Ile | |
| 335 | | | | | 340 | | | | | 345 | | | | | 350 | |
| ATC | AAC | TTC | GTG | AAT | GAC | AGG | GAG | GCT | CCC | GAC | TGG | CAG | GGC | TAC | TTT | 1103 |
| Ile | Asn | Phe | Val | Asn | Asp | Arg | Glu | Ala | Pro | Asp | Trp | Gln | Gly | Tyr | Phe | |
| | | | | 355 | | | | | 360 | | | | | 365 | | |
| TAC | ACA | GCA | CTG | CTG | TTT | GTC | AGC | GCC | TGT | CTG | CAG | ACA | CTG | GCA | CTC | 1151 |
| Tyr | Thr | Ala | Leu | Leu | Phe | Val | Ser | Ala | Cys | Leu | Gln | Thr | Leu | Ala | Leu | |
| | | | 370 | | | | | 375 | | | | | 380 | | | |

| | | | | | | | | | | | | | | | | |
|---|---|---|---|---|---|---|---|---|---|---|---|---|---|---|---|---|
| CAC | CAG | TAC | TTT | CAT | ATC | TGC | TTC | GTC | AGT | GGC | ATG | CGC | ATC | AAG | ACT | 1199 |
| His | Gln | Tyr | Phe | His | Ile | Cys | Phe | Val | Ser | Gly | Met | Arg | Ile | Lys | Thr | |
| | | 385 | | | | | 390 | | | | | 395 | | | | |
| GCT | GTG | GTG | GGC | GCT | GTC | TAT | CGT | AAG | GCT | CTT | TTG | ATC | ACC | AAT | GCA | 1247 |
| Ala | Val | Val | Gly | Ala | Val | Tyr | Arg | Lys | Ala | Leu | Leu | Ile | Thr | Asn | Ala | |
| | | 400 | | | | | 405 | | | | | 410 | | | | |
| GCT | AGA | AAA | TCT | TCC | ACG | GTC | GGA | GAG | ATT | GTC | AAC | CTC | ATG | TCC | GTG | 1295 |
| Ala | Arg | Lys | Ser | Ser | Thr | Val | Gly | Glu | Ile | Val | Asn | Leu | Met | Ser | Val | |
| | 415 | | | | 420 | | | | | 425 | | | | | 430 | |
| GAT | GCT | CAG | CGC | TTC | ATG | GAC | TTG | GCC | ACG | TAC | ATT | AAC | ATG | ATC | TGG | 1343 |
| Asp | Ala | Gln | Arg | Phe | Met | Asp | Leu | Ala | Thr | Tyr | Ile | Asn | Met | Ile | Trp | |
| | | | | 435 | | | | | 440 | | | | | 445 | | |
| TCA | GCC | CCT | CTG | CAA | GTC | ATC | CTA | GCC | CTC | TAC | TTC | CTG | TGG | CTG | AGC | 1391 |
| Ser | Ala | Pro | Leu | Gln | Val | Ile | Leu | Ala | Leu | Tyr | Phe | Leu | Trp | Leu | Ser | |
| | | | 450 | | | | | 455 | | | | | 460 | | | |
| CTG | GGC | CCT | TCT | GTG | CTG | GCT | GGA | GTG | GCT | GTG | ATG | ATT | CTC | ATG | GTA | 1439 |
| Leu | Gly | Pro | Ser | Val | Leu | Ala | Gly | Val | Ala | Val | Met | Ile | Leu | Met | Val | |
| | | | 465 | | | | | 470 | | | | | 475 | | | |
| CCC | TTA | AAT | GCT | GTG | ATG | GCC | ATG | AAG | ACC | AAG | ACC | TAC | CAG | GTG | GCA | 1487 |
| Pro | Leu | Asn | Ala | Val | Met | Ala | Met | Lys | Thr | Lys | Thr | Tyr | Gln | Val | Ala | |
| | 480 | | | | | 485 | | | | | 490 | | | | | |
| CAC | ATG | AAG | AGC | AAA | GAC | AAC | CGA | ATC | AAG | CTG | ATG | AAC | GAG | ATC | CTC | 1535 |
| His | Met | Lys | Ser | Lys | Asp | Asn | Arg | Ile | Lys | Leu | Met | Asn | Glu | Ile | Leu | |
| 495 | | | | | 500 | | | | | 505 | | | | | 510 | |
| AAT | GGG | ATC | AAA | GTC | CTC | AAG | CTG | TAC | GCC | TGG | GAG | CTG | GCC | TTC | CAG | 1583 |
| Asn | Gly | Ile | Lys | Val | Leu | Lys | Leu | Tyr | Ala | Trp | Glu | Leu | Ala | Phe | Gln | |
| | | | | 515 | | | | | 520 | | | | | 525 | | |
| GAC | AAA | GTC | ATG | AGC | ATC | AGG | CAG | GAG | GAG | CTC | AAG | GTG | CTG | AAG | AAA | 1631 |
| Asp | Lys | Val | Met | Ser | Ile | Arg | Gln | Glu | Glu | Leu | Lys | Val | Leu | Lys | Lys | |
| | | | 530 | | | | | 535 | | | | | 540 | | | |
| TCT | GCC | TAC | CTG | GCA | GCT | GTA | GGC | ACA | TTC | ACG | TGG | GTG | TGC | ACA | CCT | 1679 |
| Ser | Ala | Tyr | Leu | Ala | Ala | Val | Gly | Thr | Phe | Thr | Trp | Val | Cys | Thr | Pro | |
| | | 545 | | | | | 550 | | | | | 555 | | | | |
| TTC | CTG | GTG | GCC | CTG | TCA | ACC | TTT | GCT | GTC | TTT | GTG | ACT | GTG | GAT | GAG | 1727 |
| Phe | Leu | Val | Ala | Leu | Ser | Thr | Phe | Ala | Val | Phe | Val | Thr | Val | Asp | Glu | |
| | 560 | | | | | 565 | | | | | 570 | | | | | |
| AGA | AAT | ATC | CTA | GAT | GCA | AAG | AAA | GCC | TTT | GTG | TCC | CTA | GCC | CTG | TTC | 1775 |
| Arg | Asn | Ile | Leu | Asp | Ala | Lys | Lys | Ala | Phe | Val | Ser | Leu | Ala | Leu | Phe | |
| 575 | | | | | 580 | | | | | 585 | | | | | 590 | |
| AAT | ATC | TTG | CGC | TTC | CCA | CTC | AAC | ATC | CTG | CCC | ATG | GTT | ATC | AGC | AGC | 1823 |
| Asn | Ile | Leu | Arg | Phe | Pro | Leu | Asn | Ile | Leu | Pro | Met | Val | Ile | Ser | Ser | |
| | | | | 595 | | | | | 600 | | | | | 605 | | |
| ATT | GTG | CAG | GCC | AGC | GTG | TCC | CTC | AAG | CGT | CTC | AGG | ATT | TTT | CTG | TCT | 1871 |
| Ile | Val | Gln | Ala | Ser | Val | Ser | Leu | Lys | Arg | Leu | Arg | Ile | Phe | Leu | Ser | |
| | | | 610 | | | | | 615 | | | | | 620 | | | |
| CAT | GAG | GAG | CTG | GAG | CCA | GAC | AGC | ATT | GAG | CGG | AGG | TCG | ATC | AAG | AGT | 1919 |
| His | Glu | Glu | Leu | Glu | Pro | Asp | Ser | Ile | Glu | Arg | Arg | Ser | Ile | Lys | Ser | |
| | | 625 | | | | | 630 | | | | | 635 | | | | |
| GGA | GAA | GGG | AAT | AGC | ATC | ACT | GTG | AAG | AAT | GCA | ACC | TTC | ACT | TGG | GCC | 1967 |
| Gly | Glu | Gly | Asn | Ser | Ile | Thr | Val | Lys | Asn | Ala | Thr | Phe | Thr | Trp | Ala | |
| | | 640 | | | | | 645 | | | | | 650 | | | | |
| AGG | GGT | GAA | CCT | CCC | ACA | CTG | AAT | GGC | ATC | ACC | TTC | TCC | ATT | CCT | GAA | 2015 |
| Arg | Gly | Glu | Pro | Pro | Thr | Leu | Asn | Gly | Ile | Thr | Phe | Ser | Ile | Pro | Glu | |
| 655 | | | | | 660 | | | | | 665 | | | | | 670 | |
| GGA | GCC | CTT | GTG | GCC | GTG | GTG | GGC | CAG | GTA | GGC | TGC | GGG | AAG | TCA | TCT | 2063 |
| Gly | Ala | Leu | Val | Ala | Val | Val | Gly | Gln | Val | Gly | Cys | Gly | Lys | Ser | Ser | |
| | | | | 675 | | | | | 680 | | | | | 685 | | |
| CTG | CTG | TCA | GCC | CTG | CTG | GCT | GAG | ATG | GAC | AAG | GTG | GAG | GGA | CAT | GTG | 2111 |
| Leu | Leu | Ser | Ala | Leu | Leu | Ala | Glu | Met | Asp | Lys | Val | Glu | Gly | His | Val | |
| | | | 690 | | | | | 695 | | | | | 700 | | | |

| | | | | | | | | | | | | | | | | |
|---|---|---|---|---|---|---|---|---|---|---|---|---|---|---|---|---|
| ACT | CTC | AAG | GGC | TCC | GTG | GCC | TAC | GTG | CCC | CAG | CAG | GCC | TGG | ATT | CAG | 2159 |
| Thr | Leu | Lys | Gly | Ser | Val | Ala | Tyr | Val | Pro | Gln | Gln | Ala | Trp | Ile | Gln | |
| | | 705 | | | 710 | | | | | 715 | | | | | | |
| AAT | GAC | TCT | CTC | CGA | GAG | AAC | ATA | CTG | TTT | GGG | CAC | CCC | CTG | CAG | GAA | 2207 |
| Asn | Asp | Ser | Leu | Arg | Glu | Asn | Ile | Leu | Phe | Gly | His | Pro | Leu | Gln | Glu | |
| | 720 | | | | 725 | | | | | 730 | | | | | | |
| AAT | TAC | TAC | AAG | GCA | GTT | ATG | GAA | GCC | TGT | GCC | CTT | CTT | CCA | GAT | TTG | 2255 |
| Asn | Tyr | Tyr | Lys | Ala | Val | Met | Glu | Ala | Cys | Ala | Leu | Leu | Pro | Asp | Leu | |
| 735 | | | | 740 | | | | | 745 | | | | | 750 | | |
| GAA | ATC | CTG | CCC | AGT | GGG | GAC | CGC | ACA | GAG | ATC | GGT | GAG | AAG | GGT | GTG | 2303 |
| Glu | Ile | Leu | Pro | Ser | Gly | Asp | Arg | Thr | Glu | Ile | Gly | Glu | Lys | Gly | Val | |
| | | | | 755 | | | | | 760 | | | | | 765 | | |
| AAC | CTG | TCA | GGG | GGC | CAG | AAG | CAG | CGT | GTG | AGC | CTG | GCC | CGG | GCT | GTG | 2351 |
| Asn | Leu | Ser | Gly | Gly | Gln | Lys | Gln | Arg | Val | Ser | Leu | Ala | Arg | Ala | Val | |
| | | | 770 | | | | | 775 | | | | | 780 | | | |
| TAC | TCT | AAC | TCT | GAC | ATC | TAC | CTC | TTT | GAT | GAC | CCC | CTC | TCG | GCT | GTG | 2399 |
| Tyr | Ser | Asn | Ser | Asp | Ile | Tyr | Leu | Phe | Asp | Asp | Pro | Leu | Ser | Ala | Val | |
| | | 785 | | | | | 790 | | | | | 795 | | | | |
| GAT | GCA | CAT | GTT | GGG | AAG | CAC | ATC | TTT | GAG | AAG | GTG | GTT | GGT | CCC | ATG | 2447 |
| Asp | Ala | His | Val | Gly | Lys | His | Ile | Phe | Glu | Lys | Val | Val | Gly | Pro | Met | |
| | 800 | | | | | 805 | | | | | 810 | | | | | |
| GGC | CTA | CTG | AAG | AAC | AAG | ACA | CGG | ATC | CTG | GTC | ACC | CAT | GGT | ATC | AGC | 2495 |
| Gly | Leu | Leu | Lys | Asn | Lys | Thr | Arg | Ile | Leu | Val | Thr | His | Gly | Ile | Ser | |
| 815 | | | | | 820 | | | | | 825 | | | | | 830 | |
| TAC | CTG | CCC | CAA | GTG | GAT | GTC | ATC | ATT | GTC | ATG | AGT | GGC | GGC | AAG | ATC | 2543 |
| Tyr | Leu | Pro | Gln | Val | Asp | Val | Ile | Ile | Val | Met | Ser | Gly | Gly | Lys | Ile | |
| | | | | 835 | | | | | 840 | | | | | 845 | | |
| TCA | GAG | ATG | GGT | TCT | TAT | CAG | GAG | CTG | CTA | GAC | CGG | GAT | GGG | GCC | TTC | 2591 |
| Ser | Glu | Met | Gly | Ser | Tyr | Gln | Glu | Leu | Leu | Asp | Arg | Asp | Gly | Ala | Phe | |
| | | | 850 | | | | | 855 | | | | | 860 | | | |
| GCT | GAG | TTC | CTG | CGC | ACC | TAT | GCC | AAC | GCT | GAG | CAG | GAC | CTG | GCC | TCG | 2639 |
| Ala | Glu | Phe | Leu | Arg | Thr | Tyr | Ala | Asn | Ala | Glu | Gln | Asp | Leu | Ala | Ser | |
| | | 865 | | | | | 870 | | | | | 875 | | | | |
| GAG | GAT | GAC | AGT | GTC | AGT | GGT | TCA | GGG | AAG | GAG | TCA | AAG | CCG | GTG | GAA | 2687 |
| Glu | Asp | Asp | Ser | Val | Ser | Gly | Ser | Gly | Lys | Glu | Ser | Lys | Pro | Val | Glu | |
| | 880 | | | | | 885 | | | | | 890 | | | | | |
| AAT | GGG | ATG | CTG | GTG | ACA | GAC | ACC | GTA | GGA | AAG | CAC | CTG | CAG | AGG | CAT | 2735 |
| Asn | Gly | Met | Leu | Val | Thr | Asp | Thr | Val | Gly | Lys | His | Leu | Gln | Arg | His | |
| 895 | | | | 900 | | | | | 905 | | | | | | 910 | |
| CTC | AGC | AAC | TCG | TCT | TCC | CAC | AGT | GGG | GAT | ACC | AGC | CAG | CAA | CAC | AGC | 2783 |
| Leu | Ser | Asn | Ser | Ser | Ser | His | Ser | Gly | Asp | Thr | Ser | Gln | Gln | His | Ser | |
| | | | | 915 | | | | | 920 | | | | | 925 | | |
| AGC | ATA | GCC | GAA | CTG | CAG | AAG | GCT | GGA | GCT | AAG | GAG | GAG | ACG | TGG | AAG | 2831 |
| Ser | Ile | Ala | Glu | Leu | Gln | Lys | Ala | Gly | Ala | Lys | Glu | Glu | Thr | Trp | Lys | |
| | | | 930 | | | | | 935 | | | | | 940 | | | |
| CTA | ATG | GAA | GCA | GAC | AAG | GCC | CAG | ACA | GGG | CAG | GTG | CAG | CTG | TCA | GTG | 2879 |
| Leu | Met | Glu | Ala | Asp | Lys | Ala | Gln | Thr | Gly | Gln | Val | Gln | Leu | Ser | Val | |
| | | 945 | | | | | 950 | | | | | 955 | | | | |
| TAC | TGG | AAC | TAC | ATG | AAG | GCC | ATT | GGC | CTC | TTC | ATC | ACC | TTC | TTG | AGT | 2927 |
| Tyr | Trp | Asn | Tyr | Met | Lys | Ala | Ile | Gly | Leu | Phe | Ile | Thr | Phe | Leu | Ser | |
| | 960 | | | | | 965 | | | | | 970 | | | | | |
| ATC | TTC | CTT | TTC | CTG | TGC | AAC | CAT | GTA | TCT | GCA | CTG | GCC | TCT | AAC | TAT | 2975 |
| Ile | Phe | Leu | Phe | Leu | Cys | Asn | His | Val | Ser | Ala | Leu | Ala | Ser | Asn | Tyr | |
| 975 | | | | | 980 | | | | | 985 | | | | | 990 | |
| TGG | CTG | AGC | CTC | TGG | ACA | GAT | GAC | CCC | CCT | GTT | GTC | AAT | GGG | ACT | CAG | 3023 |
| Trp | Leu | Ser | Leu | Trp | Thr | Asp | Asp | Pro | Pro | Val | Val | Asn | Gly | Thr | Gln | |
| | | | | 995 | | | | | 1000 | | | | | 1005 | | |
| GCG | AAC | AGG | AAT | TTT | CGG | CTG | AGT | GTC | TAT | GGG | GCC | TTG | GGC | ATC | TTG | 3071 |
| Ala | Asn | Arg | Asn | Phe | Arg | Leu | Ser | Val | Tyr | Gly | Ala | Leu | Gly | Ile | Leu | |
| | | | 1010 | | | | | 1015 | | | | | 1020 | | | |

```
CAA GGT GCA GCA ATA TTT GGC TAC TCC ATG GCT GTG TCC ATC GGG GGC    3119
Gln Gly Ala Ala Ile Phe Gly Tyr Ser Met Ala Val Ser Ile Gly Gly
        1025                1030                1035

ATC TTT GCC TCC CGT CGC TTG CAC CTG GAC CTG CTA TAC AAT GTT CTT    3167
Ile Phe Ala Ser Arg Arg Leu His Leu Asp Leu Leu Tyr Asn Val Leu
    1040                1045                1050

CGA TCA CCC ATG AGT TTC TTC GAG CGT ACA CCC AGT GGG AAC CTA GTG    3215
Arg Ser Pro Met Ser Phe Phe Glu Arg Thr Pro Ser Gly Asn Leu Val
1055                1060                1065                1070

AAC CGA TTC TCC AAG GAG CTG GAC ACA GTG GAC TCC ATG ATC CCG CAG    3263
Asn Arg Phe Ser Lys Glu Leu Asp Thr Val Asp Ser Met Ile Pro Gln
            1075                1080                1085

GTC ATC AAG ATG TTC ATG GGT TCA CTC TTC AGT GTC ATT GGA GCT GTC    3311
Val Ile Lys Met Phe Met Gly Ser Leu Phe Ser Val Ile Gly Ala Val
                1090                1095                1100

ATC ATC ATC CTA CTG GCC ACG CCC ATT GCC GCA GTC ATC ATC CCA CCC    3359
Ile Ile Ile Leu Leu Ala Thr Pro Ile Ala Ala Val Ile Ile Pro Pro
            1105                1110                1115

TTG GGT CTG GTT TAC TTC TTT GTG CAG AGG TTC TAT GTG GCT TCC TCA    3407
Leu Gly Leu Val Tyr Phe Phe Val Gln Arg Phe Tyr Val Ala Ser Ser
    1120                1125                1130

AGA CAA CTG AAG CGC CTG GAG TCT GTC AGC CGT TCC CCT GTG TAC TCA    3455
Arg Gln Leu Lys Arg Leu Glu Ser Val Ser Arg Ser Pro Val Tyr Ser
1135                1140                1145                1150

CAC TTC AAT GAG ACC TTG CTG GGA GTC AGT GTC ATC CGT GCT TTT GAG    3503
His Phe Asn Glu Thr Leu Leu Gly Val Ser Val Ile Arg Ala Phe Glu
            1155                1160                1165

GAG CAG GAG CGC TTC ATT CAC CAG AGT GAC CTG AAA GTA GAT GAG AAC    3551
Glu Gln Glu Arg Phe Ile His Gln Ser Asp Leu Lys Val Asp Glu Asn
                1170                1175                1180

CAG AAG GCC TAC TAC CCC AGC ATT GTG GCC AAC AGA TGG CTT GCT GTG    3599
Gln Lys Ala Tyr Tyr Pro Ser Ile Val Ala Asn Arg Trp Leu Ala Val
            1185                1190                1195

CGC CTT GAG TGT GTG GGC AAC TGC ATT GTG CTG TTT GCT GCC CTC TTT    3647
Arg Leu Glu Cys Val Gly Asn Cys Ile Val Leu Phe Ala Ala Leu Phe
    1200                1205                1210

GCA GTC ATC TCC CGG CAC AGC CTC AGT GCT GGC TTG GTG GGC CTC TCT    3695
Ala Val Ile Ser Arg His Ser Leu Ser Ala Gly Leu Val Gly Leu Ser
1215                1220                1225                1230

GTG TCT TAC TCA CTG CAG ATA ACT GCA TAC TTG AAC TGG CTG GTT CGA    3743
Val Ser Tyr Ser Leu Gln Ile Thr Ala Tyr Leu Asn Trp Leu Val Arg
            1235                1240                1245

ATG TCC TCG GAG ATG GAG ACC AAC ATT GTG GCA GTG GAG AGA CTG AAG    3791
Met Ser Ser Glu Met Glu Thr Asn Ile Val Ala Val Glu Arg Leu Lys
                1250                1255                1260

GAG TAT TCT GAA ACA GAG AAG GAG GCT CCT TGG CAA ATC CAG GAA ACA    3839
Glu Tyr Ser Glu Thr Glu Lys Glu Ala Pro Trp Gln Ile Gln Glu Thr
            1265                1270                1275

GCT CCA CCC AGC ACC TGG CCC CAT TCA GGC CGT GTA GAG TTC CGG GAT    3887
Ala Pro Pro Ser Thr Trp Pro His Ser Gly Arg Val Glu Phe Arg Asp
    1280                1285                1290

TAC TGC CTG AGG TAT CGA GAA GAC TTG GAC TTG GTT CTC AAG CAC ATA    3935
Tyr Cys Leu Arg Tyr Arg Glu Asp Leu Asp Leu Val Leu Lys His Ile
1295                1300                1305                1310

AAT GTC ACC ATT GAG GGT GGA GAA AAG GTG GGT ATT GTA GGT CGT ACG    3983
Asn Val Thr Ile Glu Gly Gly Glu Lys Val Gly Ile Val Gly Arg Thr
            1315                1320                1325

GGA GCT GGG AAA TCA TCT CTC ACC CTG GGT TTG TTC CGG ATC AAT GAG    4031
Gly Ala Gly Lys Ser Ser Leu Thr Leu Gly Leu Phe Arg Ile Asn Glu
        1330                1335                1340
```

```
TCT GCA GAA GGG GAG ATC ATC ATT GAT GGG GTC AAC ATC GCC AAG ATC                    4079
Ser Ala Glu Gly Glu Ile Ile Ile Asp Gly Val Asn Ile Ala Lys Ile
        1345                1350                1355

GGC CTG CAC AAC CTG CGC TTC AAG ATC ACC ATC ATT CCA CAG GAT CCT                    4127
Gly Leu His Asn Leu Arg Phe Lys Ile Thr Ile Ile Pro Gln Asp Pro
1360                1365                1370

GTT TTG TTC TCG GGT TCC CTC CGC ATG AAC TTG GAC CCT TTC AGT CAG                    4175
Val Leu Phe Ser Gly Ser Leu Arg Met Asn Leu Asp Pro Phe Ser Gln
1375                1380                1385                1390

TAT TCT GAT GAA GAA GTC TGG ATG GCC CTG GAG CTT GCT CAC CTA AAG                    4223
Tyr Ser Asp Glu Glu Val Trp Met Ala Leu Glu Leu Ala His Leu Lys
            1395                1400                1405

GGC TTT GTG TCA GCC TTG CCT GAC AAG CTG AAC CAT GAG TGT GCA GAA                    4271
Gly Phe Val Ser Ala Leu Pro Asp Lys Leu Asn His Glu Cys Ala Glu
        1410                1415                1420

GGT GGA GAG AAC CTG AGT GTG GGG CAG CGA CAG CTT GTG TGC CTG GCC                    4319
Gly Gly Glu Asn Leu Ser Val Gly Gln Arg Gln Leu Val Cys Leu Ala
    1425                1430                1435

CGG GCT CTG CTG AGG AAG ACA AAG ATT CTA GTG TTG GAC GAG GCT ACC                    4367
Arg Ala Leu Leu Arg Lys Thr Lys Ile Leu Val Leu Asp Glu Ala Thr
1440                1445                1450

GCA GCT GTG GAC CTA GAG ACA GAT AAC CTT ATC CAG TCC ACC ATC CGG                    4415
Ala Ala Val Asp Leu Glu Thr Asp Asn Leu Ile Gln Ser Thr Ile Arg
1455                1460                1465                1470

ACG CAG TTT GAA GAC TGT ACT GTG CTC ACG ATT GCT CAT CGG CTT AAC                    4463
Thr Gln Phe Glu Asp Cys Thr Val Leu Thr Ile Ala His Arg Leu Asn
            1475                1480                1485

ACC ATA ATG GAC TAC ACA CGG GTT ATT GTC CTG GAC AAA GGA GAA GTT                    4511
Thr Ile Met Asp Tyr Thr Arg Val Ile Val Leu Asp Lys Gly Glu Val
        1490                1495                1500

CGG GAG TGT GGT GCA CCC TCT GAG CTC CTG CAG CAA AGA GGC ATC TTC                    4559
Arg Glu Cys Gly Ala Pro Ser Glu Leu Leu Gln Gln Arg Gly Ile Phe
    1505                1510                1515

TAC AGC ATG GCC AAG GAT GCT GGC TTG GTG TGAGCTGGTC TCTGGCTTAT                      4609
Tyr Ser Met Ala Lys Asp Ala Gly Leu Val
1520                1525

CCAATGAGGA CTGCAGGGCC AGGATCCCAG TGTCCAGGCA TGAGCCAGCA ACCCTGGAAA                  4669
CCTACGCTTC CCAGACAAAA CCCAAAAATT AAAAACAAAA CCAAACTAAA AGGAAGCAAA                  4729
ATACTTAGGT GTCTGTCACC ATTTGGCTTC ATCCTGGATC TGACCTTGAA GAAGCTGGAA                  4789
GACAGATGCA CCCCACTTCA GATACACGTC TGGCCTCTGG CACCCTGAAA GTTCACCCAT                  4849
GCTCCTGCCG TATCCCACGG CAAGTCCATG GGCAGCTAAA CATACTAGTG ACCAAACACA                  4909
AGCCACACTG CCTCATGTCT CTTCAGCCAC GTCTACGGAT GCCAAGCCTT GTAGCCTCTC                  4969
CTGGCTTTGC CAGCTCTCTG TCACCTATAG TCGTGTTGGT TACAGAAGAG TGCATCTTGC                  5029
CTTCAGGTCT TGCAGTTGAA ACATGGGAAC CAAAATGAAC AAAAAGGAGA GAAAGAAAAC                  5089
CCCTAAAACG TTCCTGTCCC TGTTATGTCA GTGATGTCCC CTTCCTGCCA TCTGGTCTTC                  5149
ATGCACGCTG ACACTGTCCC TTCTTCAGCA CAGCTTTCAC AGGACCTGCT TAAGACACGG                  5209
CCTTGTGAAG GGACCTAGGC AGACAGGCTT GGAACCAGGC CAGGCAACAC TCCCTTCACA                  5269
AGGACTTATA CCTTGCCCCT GCTTTCTGTT TCTTCCTGTT CAAAGCTGGG GAGGGCTCAC                  5329
TCCTCACATA AGGTCTATGA ATAGTTATAA GCAGCAAAAG TCAAGAGCAG AAGGGATGGT                  5389
GCCTGCGGGC AAGAATCTGG TATCAAAGAC AGCCAGAGTT TCTTATAGGG CCAGAAGAGA                  5449
ACCATTCACA AATATCAGTG ATTTCTCCCC ACTACTTTTG AGCATCGTTT CGTGGAGAAG                  5509
GATAGTCCCA AGAATTTGAT GTCTGGGAGA AGGTACTAGA TTCAGGGAGC AGCCATGCCC                  5569
```

```
AGCTCTGCAC TTGATCCTCA GTCTGAATAC TTCAAAGTGG TCCTCTAGGT TGTGTGAGTT      5629

ACAGACCAAA GAGAGACCCC CATGGTTAGC AAGAACTTGA TGCCAGCCAC AGTTCATACT      5689

TGCTTTGAAT TTTGGCTCTA ATGTCAGTCC CAGAGAAGCA TCCTTTTTCT TTAGGTGGCA      5749

ATATATGTAT TTATTTTTTG TAAGTTAATA CCATTCTTTC ACTTTAAAGG GCCCAGATTT      5809

CTCCTGAGAG TCTTTTTGTA ATGACACTGG AAACATGACT ATTTGAAAAT AATTTGCAGT      5869

AAAGAAAAAT ATTCATCCG                                                  5889
```

( 2 ) INFORMATION FOR SEQ ID NO:6:

( i ) SEQUENCE CHARACTERISTICS:
        ( A ) LENGTH: 1528 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
        Met Ala Leu Arg Ser Phe Cys Ser Ala Asp Gly Ser Asp Pro
         1               5                  10

Leu Trp Asp Trp Asn Val Thr Trp His Thr Ser Asn Pro Asp Phe Thr
 15                  20                  25                  30

Lys Cys Phe Gln Asn Thr Val Leu Thr Trp Val Pro Cys Phe Tyr Leu
                     35                  40                  45

Trp Ser Cys Phe Pro Leu Tyr Phe Phe Tyr Leu Ser Arg His Asp Arg
                 50                  55                  60

Gly Tyr Ile Gln Met Thr His Leu Asn Lys Thr Lys Thr Ala Leu Gly
             65                  70                  75

Phe Phe Leu Trp Ile Ile Cys Trp Ala Asp Leu Phe Tyr Ser Phe Trp
 80                              85                  90

Glu Arg Ser Gln Gly Val Leu Arg Ala Pro Val Leu Leu Val Ser Pro
 95                 100                 105                 110

Thr Leu Leu Gly Ile Thr Met Leu Leu Ala Thr Phe Leu Ile Gln Leu
                115                 120                 125

Glu Arg Arg Lys Gly Val Gln Ser Ser Gly Ile Met Leu Thr Phe Trp
            130                 135                 140

Leu Val Ala Leu Leu Cys Ala Leu Ala Ile Leu Arg Ser Lys Ile Ile
            145                 150                 155

Ser Ala Leu Lys Lys Asp Ala His Val Asp Val Phe Arg Asp Ser Thr
    160                 165                 170

Phe Tyr Leu Tyr Phe Thr Leu Val Leu Val Gln Leu Val Leu Ser Cys
175                 180                 185                 190

Phe Ser Asp Cys Ser Pro Leu Phe Ser Glu Thr Val His Asp Arg Asn
                195                 200                 205

Pro Cys Pro Glu Ser Ser Ala Ser Phe Leu Ser Arg Ile Thr Phe Trp
            210                 215                 220

Trp Ile Thr Gly Met Met Val His Gly Tyr Arg Gln Pro Leu Glu Ser
            225                 230                 235

Ser Asp Leu Trp Ser Leu Asn Lys Glu Asp Thr Ser Glu Glu Val Val
    240                 245                 250

Pro Val Leu Val Asn Asn Trp Lys Lys Glu Cys Asp Lys Ser Arg Lys
255                 260                 265                 270

Gln Pro Val Arg Ile Val Tyr Ala Pro Pro Lys Asp Pro Ser Lys Pro
                275                 280                 285

Lys Gly Ser Ser Gln Leu Asp Val Asn Glu Val Glu Ala Leu Ile
            290                 295                 300
```

-continued

| | | | | | | | | | | | | | | |
|---|---|---|---|---|---|---|---|---|---|---|---|---|---|---|
| Val | Lys | Ser 305 | Pro | His | Lys | Asp | Arg 310 | Glu | Pro | Ser | Leu | Phe 315 | Lys | Val | Leu |
| Tyr | Lys 320 | Thr | Phe | Gly | Pro | Tyr 325 | Phe | Leu | Met | Ser | Phe 330 | Leu | Tyr | Lys | Ala |
| Leu 335 | His | Asp | Leu | Met | Met 340 | Phe | Ala | Gly | Pro | Lys 345 | Ile | Leu | Glu | Leu | Ile 350 |
| Ile | Asn | Phe | Val | Asn 355 | Asp | Arg | Glu | Ala | Pro 360 | Asp | Trp | Gln | Gly | Tyr 365 | Phe |
| Tyr | Thr | Ala | Leu 370 | Leu | Phe | Val | Ser | Ala 375 | Cys | Leu | Gln | Thr | Leu 380 | Ala | Leu |
| His | Gln | Tyr 385 | Phe | His | Ile | Cys | Phe 390 | Val | Ser | Gly | Met | Arg 395 | Ile | Lys | Thr |
| Ala | Val 400 | Val | Gly | Ala | Val | Tyr 405 | Arg | Lys | Ala | Leu | Leu 410 | Ile | Thr | Asn | Ala |
| Ala 415 | Arg | Lys | Ser | Ser | Thr 420 | Val | Gly | Glu | Ile | Val 425 | Asn | Leu | Met | Ser | Val 430 |
| Asp | Ala | Gln | Arg | Phe 435 | Met | Asp | Leu | Ala | Thr 440 | Tyr | Ile | Asn | Met | Ile 445 | Trp |
| Ser | Ala | Pro | Leu 450 | Gln | Val | Ile | Leu | Ala 455 | Leu | Tyr | Phe | Leu | Trp 460 | Leu | Ser |
| Leu | Gly | Pro 465 | Ser | Val | Leu | Ala | Gly 470 | Val | Ala | Val | Met | Ile 475 | Leu | Met | Val |
| Pro | Leu 480 | Asn | Ala | Val | Met | Ala 485 | Met | Lys | Thr | Lys | Thr 490 | Tyr | Gln | Val | Ala |
| His 495 | Met | Lys | Ser | Lys | Asp 500 | Asn | Arg | Ile | Lys | Leu 505 | Met | Asn | Glu | Ile | Leu 510 |
| Asn | Gly | Ile | Lys | Val 515 | Leu | Lys | Leu | Tyr | Ala 520 | Trp | Glu | Leu | Ala | Phe 525 | Gln |
| Asp | Lys | Val | Met 530 | Ser | Ile | Arg | Gln | Glu 535 | Glu | Leu | Lys | Val | Leu 540 | Lys | Lys |
| Ser | Ala | Tyr 545 | Leu | Ala | Ala | Val | Gly 550 | Thr | Phe | Thr | Trp | Val 555 | Cys | Thr | Pro |
| Phe | Leu 560 | Val | Ala | Leu | Ser | Thr 565 | Phe | Ala | Val | Phe | Val 570 | Thr | Val | Asp | Glu |
| Arg 575 | Asn | Ile | Leu | Asp | Ala 580 | Lys | Lys | Ala | Phe | Val 585 | Ser | Leu | Ala | Leu | Phe 590 |
| Asn | Ile | Leu | Arg | Phe 595 | Pro | Leu | Asn | Ile | Leu 600 | Pro | Met | Val | Ile | Ser 605 | Ser |
| Ile | Val | Gln | Ala 610 | Ser | Val | Ser | Leu | Lys 615 | Arg | Leu | Arg | Ile | Phe 620 | Leu | Ser |
| His | Glu | Glu 625 | Leu | Glu | Pro | Asp | Ser 630 | Ile | Glu | Arg | Arg | Ser 635 | Ile | Lys | Ser |
| Gly | Glu 640 | Gly | Asn | Ser | Ile | Thr 645 | Val | Lys | Asn | Ala | Thr 650 | Phe | Thr | Trp | Ala |
| Arg 655 | Gly | Glu | Pro | Pro | Thr 660 | Leu | Asn | Gly | Ile | Thr 665 | Phe | Ser | Ile | Pro | Glu 670 |
| Gly | Ala | Leu | Val | Ala 675 | Val | Val | Gly | Gln | Val 680 | Gly | Cys | Gly | Lys | Ser 685 | Ser |
| Leu | Leu | Ser | Ala 690 | Leu | Leu | Ala | Glu | Met 695 | Asp | Lys | Val | Glu | Gly 700 | His | Val |
| Thr | Leu | Lys 705 | Gly | Ser | Val | Ala | Tyr 710 | Val | Pro | Gln | Gln | Ala 715 | Trp | Ile | Gln |
| Asn | Asp | Ser | Leu | Arg | Glu | Asn | Ile | Leu | Phe | Gly | His | Pro | Leu | Gln | Glu |

-continued

```
                        720                        725                             730
Asn  Tyr  Tyr  Lys  Ala  Val  Met  Glu  Ala  Cys  Ala  Leu  Leu  Pro  Asp  Leu
735                      740                       745                            750

Glu  Ile  Leu  Pro  Ser  Gly  Asp  Arg  Thr  Glu  Ile  Gly  Glu  Lys  Gly  Val
                         755                       760                            765

Asn  Leu  Ser  Gly  Gly  Gln  Lys  Gln  Arg  Val  Ser  Leu  Ala  Arg  Ala  Val
                    770                       775                      780

Tyr  Ser  Asn  Ser  Asp  Ile  Tyr  Leu  Phe  Asp  Asp  Pro  Leu  Ser  Ala  Val
               785                       790                     795

Asp  Ala  His  Val  Gly  Lys  His  Ile  Phe  Glu  Lys  Val  Gly  Pro  Met
          800                       805                      810

Gly  Leu  Leu  Lys  Asn  Lys  Thr  Arg  Ile  Leu  Val  Thr  His  Gly  Ile  Ser
815                      820                       825                            830

Tyr  Leu  Pro  Gln  Val  Asp  Val  Ile  Ile  Val  Met  Ser  Gly  Gly  Lys  Ile
                    835                       840                      845

Ser  Glu  Met  Gly  Ser  Tyr  Gln  Glu  Leu  Leu  Asp  Arg  Asp  Gly  Ala  Phe
               850                       855                     860

Ala  Glu  Phe  Leu  Arg  Thr  Tyr  Ala  Asn  Ala  Glu  Gln  Asp  Leu  Ala  Ser
          865                       870                      875

Glu  Asp  Asp  Ser  Val  Ser  Gly  Ser  Gly  Lys  Glu  Ser  Lys  Pro  Val  Glu
     880                       885                      890

Asn  Gly  Met  Leu  Val  Thr  Asp  Thr  Val  Gly  Lys  His  Leu  Gln  Arg  His
895                      900                       905                            910

Leu  Ser  Asn  Ser  Ser  Ser  His  Ser  Gly  Asp  Thr  Ser  Gln  Gln  His  Ser
                         915                       920                       925

Ser  Ile  Ala  Glu  Leu  Gln  Lys  Ala  Gly  Ala  Lys  Glu  Glu  Thr  Trp  Lys
               930                       935                      940

Leu  Met  Glu  Ala  Asp  Lys  Ala  Gln  Thr  Gly  Gln  Val  Gln  Leu  Ser  Val
          945                       950                      955

Tyr  Trp  Asn  Tyr  Met  Lys  Ala  Ile  Gly  Leu  Phe  Ile  Thr  Phe  Leu  Ser
960                      965                       970

Ile  Phe  Leu  Phe  Leu  Cys  Asn  His  Val  Ser  Ala  Leu  Ala  Ser  Asn  Tyr
975                      980                       985                            990

Trp  Leu  Ser  Leu  Trp  Thr  Asp  Asp  Pro  Pro  Val  Val  Asn  Gly  Thr  Gln
                    995                       1000                      1005

Ala  Asn  Arg  Asn  Phe  Arg  Leu  Ser  Val  Tyr  Gly  Ala  Leu  Gly  Ile  Leu
               1010                      1015                     1020

Gln  Gly  Ala  Ala  Ile  Phe  Gly  Tyr  Ser  Met  Ala  Val  Ser  Ile  Gly  Gly
          1025                      1030                     1035

Ile  Phe  Ala  Ser  Arg  Arg  Leu  His  Leu  Asp  Leu  Leu  Tyr  Asn  Val  Leu
     1040                      1045                      1050

Arg  Ser  Pro  Met  Ser  Phe  Phe  Glu  Arg  Thr  Pro  Ser  Gly  Asn  Leu  Val
1055                     1060                      1065                      1070

Asn  Arg  Phe  Ser  Lys  Glu  Leu  Asp  Thr  Val  Asp  Ser  Met  Ile  Pro  Gln
               1075                      1080                     1085

Val  Ile  Lys  Met  Phe  Met  Gly  Ser  Leu  Phe  Ser  Val  Ile  Gly  Ala  Val
          1090                      1095                     1100

Ile  Ile  Ile  Leu  Leu  Ala  Thr  Pro  Ile  Ala  Ala  Val  Ile  Ile  Pro  Pro
          1105                      1110                     1115

Leu  Gly  Leu  Val  Tyr  Phe  Phe  Val  Gln  Arg  Phe  Tyr  Val  Ala  Ser  Ser
     1120                      1125                      1130

Arg  Gln  Leu  Lys  Arg  Leu  Glu  Ser  Val  Ser  Arg  Ser  Pro  Val  Tyr  Ser
1135                     1140                      1145                      1150
```

His Phe Asn Glu Thr Leu Leu Gly Val Ser Val Ile Arg Ala Phe Glu
            1155                1160                1165

Glu Gln Glu Arg Phe Ile His Gln Ser Asp Leu Lys Val Asp Glu Asn
            1170                1175                1180

Gln Lys Ala Tyr Tyr Pro Ser Ile Val Ala Asn Arg Trp Leu Ala Val
            1185                1190                1195

Arg Leu Glu Cys Val Gly Asn Cys Ile Val Leu Phe Ala Ala Leu Phe
    1200                1205                1210

Ala Val Ile Ser Arg His Ser Leu Ser Ala Gly Leu Val Gly Leu Ser
1215                1220                1225                1230

Val Ser Tyr Ser Leu Gln Ile Thr Ala Tyr Leu Asn Trp Leu Val Arg
            1235                1240                1245

Met Ser Ser Glu Met Glu Thr Asn Ile Val Ala Val Glu Arg Leu Lys
            1250                1255                1260

Glu Tyr Ser Glu Thr Glu Lys Glu Ala Pro Trp Gln Ile Gln Glu Thr
            1265                1270                1275

Ala Pro Pro Ser Thr Trp Pro His Ser Gly Arg Val Glu Phe Arg Asp
    1280                1285                1290

Tyr Cys Leu Arg Tyr Arg Glu Asp Leu Asp Leu Val Leu Lys His Ile
1295                1300                1305                1310

Asn Val Thr Ile Glu Gly Gly Glu Lys Val Gly Ile Val Gly Arg Thr
            1315                1320                1325

Gly Ala Gly Lys Ser Ser Leu Thr Leu Gly Leu Phe Arg Ile Asn Glu
            1330                1335                1340

Ser Ala Glu Gly Glu Ile Ile Ile Asp Gly Val Asn Ile Ala Lys Ile
    1345                1350                1355

Gly Leu His Asn Leu Arg Phe Lys Ile Thr Ile Ile Pro Gln Asp Pro
    1360                1365                1370

Val Leu Phe Ser Gly Ser Leu Arg Met Asn Leu Asp Pro Phe Ser Gln
1375                1380                1385                1390

Tyr Ser Asp Glu Glu Val Trp Met Ala Leu Glu Leu Ala His Leu Lys
            1395                1400                1405

Gly Phe Val Ser Ala Leu Pro Asp Lys Leu Asn His Glu Cys Ala Glu
            1410                1415                1420

Gly Gly Glu Asn Leu Ser Val Gly Gln Arg Gln Leu Val Cys Leu Ala
            1425                1430                1435

Arg Ala Leu Leu Arg Lys Thr Lys Ile Leu Val Leu Asp Glu Ala Thr
    1440                1445                1450

Ala Ala Val Asp Leu Glu Thr Asp Asn Leu Ile Gln Ser Thr Ile Arg
1455                1460                1465                1470

Thr Gln Phe Glu Asp Cys Thr Val Leu Thr Ile Ala His Arg Leu Asn
            1475                1480                1485

Thr Ile Met Asp Tyr Thr Arg Val Ile Val Leu Asp Lys Gly Glu Val
            1490                1495                1500

Arg Glu Cys Gly Ala Pro Ser Glu Leu Leu Gln Gln Arg Gly Ile Phe
    1505                1510                1515

Tyr Ser Met Ala Lys Asp Ala Gly Leu Val
1520                1525

( 2 ) INFORMATION FOR SEQ ID NO:7:

( i ) SEQUENCE CHARACTERISTICS:
      ( A ) LENGTH: 1548 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:7:

```
Met  Val  Asp  Asn  Gly  His  Val  Thr  Ile  Ala  Met  Ala  Asp  Leu  Gly  Thr
1              5                   10                       15

Val  Val  Glu  Ile  Ala  Gln  Val  Arg  Cys  Gln  Gln  Glu  Ala  Gln  Arg  Lys
               20                  25                       30

Phe  Ala  Glu  Gln  Leu  Asp  Glu  Leu  Trp  Gly  Gly  Glu  Pro  Ala  Tyr  Thr
          35                       40                  45

Pro  Thr  Val  Glu  Asp  Gln  Ala  Ser  Trp  Phe  Gln  Gln  Leu  Tyr  Tyr  Gly
     50                       55                  60

Trp  Ile  Gly  Asp  Tyr  Ile  Tyr  Lys  Ala  Ala  Ala  Gly  Asn  Ile  Thr  Glu
65                        70                  75                            80

Ala  Asp  Leu  Pro  Pro  Pro  Thr  Arg  Ser  Thr  Arg  Thr  Tyr  His  Ile  Gly
                    85                       90                       95

Arg  Lys  Leu  Ser  Arg  Gln  Ala  His  Ala  Asp  Ile  Asp  Ala  Ser  Arg  Arg
               100                      105                      110

Trp  Gln  Gly  Tyr  Ile  Gly  Cys  Glu  Val  Val  Tyr  Lys  Ser  Cys  Ala  Glu
          115                      120                      125

Ala  Lys  Gly  Val  Leu  Arg  Trp  Val  Gly  His  Leu  Gln  Ser  Asp  Tyr
     130                      135                      140

Pro  Arg  Ser  Leu  Val  Ala  Gly  Val  Glu  Trp  Arg  Met  Pro  Pro  Arg  His
145                      150                      155                      160

Arg  Arg  Leu  Ala  Val  Leu  Gly  Ser  Ala  Ala  Ala  Leu  His  Asn  Gly  Val
                    165                      170                      175

Val  His  Gly  Glu  Arg  Leu  Phe  Trp  Pro  His  Glu  Asp  Asn  Tyr  Leu  Cys
               180                      185                      190

Ser  Cys  Glu  Pro  Val  Glu  Gln  Leu  Tyr  Val  Lys  Ser  Lys  Tyr  Asn  Leu
          195                      200                      205

Ile  Pro  Pro  Arg  Pro  Pro  Pro  Ser  Pro  Asp  Leu  Leu  Arg  Thr  Leu  Phe
     210                      215                      220

Lys  Val  His  Trp  Tyr  His  Val  Trp  Ala  Gln  Ile  Leu  Pro  Lys  Leu  Leu
225                      230                      235                      240

Ser  Asp  Val  Thr  Ala  Leu  Met  Leu  Pro  Val  Leu  Leu  Glu  Tyr  Phe  Val
                    245                      250                      255

Lys  Tyr  Leu  Asn  Ala  Asp  Asn  Ala  Thr  Trp  Gly  Trp  Gly  Leu  Gly  Leu
               260                      265                      270

Ala  Leu  Thr  Ile  Phe  Leu  Thr  Asn  Val  Ile  Gln  Ser  Cys  Ser  Ala  His
          275                      280                      285

Lys  Tyr  Asp  His  Ile  Ser  Ile  Arg  Thr  Ala  Ala  Leu  Phe  Glu  Thr  Ser
     290                      295                      300

Ser  Met  Ala  Leu  Leu  Phe  Glu  Lys  Cys  Phe  Thr  Val  Ser  Arg  Arg  Ser
305                      310                      315                      320

Leu  Gln  Arg  Pro  Asp  Met  Ser  Val  Gly  Arg  Ile  Met  Asn  Met  Val  Gly
               325                      330                      335

Asn  Asp  Val  Asp  Asn  Ile  Gly  Ser  Leu  Asn  Trp  Tyr  Val  Met  Tyr  Phe
               340                      345                      350

Trp  Ser  Ala  Pro  Leu  Gln  Leu  Val  Leu  Cys  Leu  Leu  Leu  Ile  Arg
          355                      360                      365

Leu  Val  Gly  Trp  Leu  Arg  Val  Pro  Gly  Met  Ala  Val  Leu  Phe  Val  Thr
     370                      375                      380

Leu  Pro  Leu  Gln  Ala  Val  Ile  Ser  Lys  His  Val  Gln  Asp  Val  Ser  Glu
385                      390                      395                      400
```

```
Arg  Met  Ala  Ser  Val  Val  Asp  Leu  Arg  Ile  Lys  Arg  Thr  Asn  Glu  Leu
               405                 410                      415

Leu  Ser  Gly  Val  Arg  Ile  Val  Lys  Phe  Met  Gly  Trp  Glu  Pro  Val  Phe
               420                 425                      430

Leu  Ala  Arg  Ile  Gln  Asp  Ala  Arg  Ser  Arg  Glu  Leu  Arg  Cys  Leu  Arg
               435                 440                      445

Asp  Val  His  Val  Ala  Asn  Val  Phe  Phe  Met  Phe  Val  Asn  Asp  Ala  Thr
     450                      455                      460

Pro  Thr  Leu  Val  Ile  Ala  Val  Val  Phe  Ile  Leu  Tyr  His  Val  Ser  Gly
465                      470                      475                      480

Lys  Val  Leu  Lys  Pro  Glu  Val  Val  Phe  Pro  Thr  Ile  Ala  Leu  Leu  Asn
                    485                 490                           495

Thr  Met  Arg  Val  Ser  Phe  Phe  Met  Ile  Pro  Ile  Ile  Ile  Ser  Ser  Ile
               500                 505                      510

Leu  Gln  Cys  Phe  Val  Ser  Ala  Lys  Arg  Val  Thr  Ala  Phe  Ile  Glu  Cys
               515                 520                      525

Pro  Asp  Thr  His  Ser  Gln  Val  Gln  Asp  Ile  Ala  Ser  Ile  Asp  Val  Pro
     530                      535                      540

Asp  Ala  Ala  Ala  Ile  Phe  Lys  Gly  Ala  Ser  Ile  His  Thr  Tyr  Leu  Pro
545                      550                      555                      560

Val  Lys  Leu  Pro  Arg  Cys  Lys  Ser  Arg  Leu  Thr  Ala  Met  Gln  Arg  Ser
                    565                 570                           575

Thr  Leu  Trp  Phe  Arg  Arg  Arg  Gly  Val  Pro  Glu  Thr  Glu  Trp  Tyr  Glu
               580                 585                      590

Val  Asp  Ser  Pro  Asp  Ala  Ser  Ala  Ser  Ser  Leu  Ala  Val  His  Ser  Thr
               595                 600                      605

Thr  Val  His  Met  Gly  Ser  Thr  Gln  Thr  Val  Ile  Thr  Asp  Ser  Asp  Gly
     610                      615                      620

Ala  Ala  Gly  Glu  Asp  Glu  Lys  Gly  Glu  Val  Glu  Glu  Gly  Asp  Arg  Glu
625                      630                      635                      640

Tyr  Tyr  Gln  Leu  Val  Ser  Lys  Glu  Leu  Leu  Arg  Asn  Val  Ser  Leu  Thr
                    645                 650                           655

Ile  Pro  Lys  Gly  Lys  Leu  Thr  Met  Val  Ile  Gly  Ser  Thr  Gly  Ser  Gly
               660                 665                      670

Lys  Ser  Thr  Leu  Leu  Gly  Ala  Leu  Met  Gly  Glu  Tyr  Ser  Val  Glu  Ser
          675                 680                      685

Gly  Glu  Leu  Trp  Ala  Glu  Arg  Ser  Ile  Ala  Tyr  Val  Pro  Gln  Gln  Ala
     690                      695                      700

Trp  Ile  Met  Asn  Ala  Thr  Leu  Arg  Gly  Asn  Ile  Leu  Phe  Phe  Asp  Glu
705                      710                      715                      720

Glu  Arg  Ala  Glu  Asp  Leu  Gln  Asp  Val  Ile  Arg  Cys  Cys  Gln  Leu  Glu
                    725                 730                           735

Ala  Asp  Leu  Ala  Gln  Phe  Cys  Gly  Gly  Leu  Asp  Thr  Glu  Ile  Gly  Glu
               740                 745                      750

Met  Gly  Val  Asn  Leu  Ser  Gly  Gly  Gln  Lys  Ala  Arg  Val  Ser  Leu  Ala
          755                 760                      765

Arg  Ala  Val  Tyr  Ala  Asn  Arg  Asp  Val  Tyr  Leu  Leu  Asp  Asp  Pro  Leu
     770                      775                      780

Ser  Ala  Leu  Asp  Ala  His  Val  Gly  Gln  Arg  Ile  Val  Gln  Asp  Val  Ile
785                      790                      795                      800

Leu  Gly  Arg  Leu  Arg  Gly  Lys  Thr  Arg  Val  Leu  Ala  Thr  His  Gln  Ile
                    805                 810                           815

His  Leu  Leu  Pro  Leu  Ala  Asp  Tyr  Ile  Val  Val  Leu  Gln  His  Gly  Ser
```

-continued

|     |     |     |     |     | 820 |     |     |     |     | 825 |     |     |     |     | 830 |     |
| --- | --- | --- | --- | --- | --- | --- | --- | --- | --- | --- | --- | --- | --- | --- | --- | --- |
| Ile | Val | Phe | Ala | Gly | Asp | Phe | Ala | Ala | Phe | Ser | Ala | Thr | Ala | Leu | Glu |
|     |     | 835 |     |     |     |     | 840 |     |     |     |     | 845 |     |     |     |
| Glu | Thr | Leu | Arg | Gly | Glu | Leu | Lys | Gly | Ser | Lys | Asp | Val | Glu | Ser | Cys |
|     | 850 |     |     |     |     | 855 |     |     |     |     | 860 |     |     |     |     |
| Ser | Ser | Asp | Val | Asp | Thr | Glu | Ser | Ala | Thr | Ala | Glu | Thr | Ala | Pro | Tyr |
| 865 |     |     |     |     | 870 |     |     |     |     | 875 |     |     |     |     | 880 |
| Val | Ala | Lys | Ala | Lys | Gly | Leu | Asn | Ala | Glu | Gln | Glu | Thr | Ser | Leu | Ala |
|     |     |     |     | 885 |     |     |     |     | 890 |     |     |     |     | 895 |     |
| Gly | Gly | Glu | Asp | Pro | Leu | Arg | Ser | Asp | Val | Glu | Ala | Gly | Arg | Leu | Met |
|     |     |     | 900 |     |     |     |     | 905 |     |     |     |     | 910 |     |     |
| Thr | Thr | Glu | Glu | Lys | Ala | Thr | Gly | Lys | Val | Pro | Trp | Ser | Thr | Tyr | Val |
|     |     | 915 |     |     |     |     | 920 |     |     |     |     | 925 |     |     |     |
| Ala | Tyr | Leu | Lys | Ser | Cys | Gly | Gly | Leu | Glu | Ala | Trp | Gly | Cys | Leu | Leu |
|     | 930 |     |     |     |     | 935 |     |     |     |     | 940 |     |     |     |     |
| Ala | Thr | Phe | Ala | Leu | Thr | Glu | Cys | Val | Thr | Ala | Ala | Ser | Ser | Val | Trp |
| 945 |     |     |     |     | 950 |     |     |     |     | 955 |     |     |     |     | 960 |
| Leu | Ser | Ile | Trp | Ser | Thr | Gly | Ser | Leu | Met | Trp | Ser | Ala | Asp | Thr | Tyr |
|     |     |     |     | 965 |     |     |     |     | 970 |     |     |     |     | 975 |     |
| Leu | Tyr | Val | Tyr | Leu | Phe | Ile | Val | Phe | Leu | Glu | Ile | Phe | Gly | Ser | Pro |
|     |     |     | 980 |     |     |     |     | 985 |     |     |     |     | 990 |     |     |
| Leu | Arg | Phe | Phe | Leu | Cys | Tyr | Tyr | Leu | Ile | Arg | Ile | Gly | Ser | Arg | Asn |
|     |     | 995 |     |     |     |     | 1000 |     |     |     |     | 1005 |     |     |     |
| Met | His | Arg | Asp | Leu | Leu | Glu | Ser | Ile | Gly | Val | Ala | Arg | Met | Ser | Phe |
|     |     | 1010 |     |     |     |     | 1015 |     |     |     |     | 1020 |     |     |     |
| Phe | Asp | Thr | Thr | Pro | Val | Gly | Arg | Val | Leu | Asn | Arg | Phe | Thr | Lys | Asp |
| 1025 |     |     |     |     | 1030 |     |     |     |     | 1035 |     |     |     |     | 1040 |
| Met | Ser | Ile | Leu | Asp | Asn | Thr | Leu | Asn | Asp | Gly | Tyr | Leu | Tyr | Leu | Leu |
|     |     |     |     | 1045 |     |     |     |     | 1050 |     |     |     |     | 1055 |     |
| Glu | Tyr | Phe | Phe | Ser | Met | Cys | Ser | Thr | Val | Ile | Ile | Met | Val | Val | Val |
|     |     |     |     | 1060 |     |     |     |     | 1065 |     |     |     |     | 1070 |     |
| Gln | Pro | Phe | Val | Leu | Val | Ala | Ile | Val | Pro | Cys | Val | Tyr | Ser | Tyr | Tyr |
|     |     |     | 1075 |     |     |     |     | 1080 |     |     |     |     | 1085 |     |     |
| Lys | Leu | Met | Gln | Val | Tyr | Asn | Ala | Ser | Asn | Arg | Glu | Thr | Arg | Arg | Ile |
|     | 1090 |     |     |     |     | 1095 |     |     |     |     | 1100 |     |     |     |     |
| Lys | Ser | Ile | Ala | His | Ser | Pro | Val | Phe | Thr | Leu | Leu | Glu | Glu | Ser | Leu |
| 1105 |     |     |     |     | 1110 |     |     |     |     | 1115 |     |     |     |     | 1120 |
| Gln | Gly | Gln | Arg | Thr | Ile | Ala | Thr | Tyr | Gly | Lys | Leu | His | Leu | Val | Leu |
|     |     |     |     | 1125 |     |     |     |     | 1130 |     |     |     |     | 1135 |     |
| Gln | Glu | Ala | Leu | Gly | Arg | Leu | Asp | Val | Val | Tyr | Ser | Ala | Leu | Tyr | Met |
|     |     |     |     | 1140 |     |     |     |     | 1145 |     |     |     |     | 1150 |     |
| Gln | Asn | Val | Ser | Asn | Arg | Trp | Leu | Gly | Val | Arg | Leu | Glu | Phe | Leu | Ser |
|     |     |     |     | 1155 |     |     |     |     | 1160 |     |     |     |     | 1165 |     |
| Cys | Val | Val | Thr | Phe | Met | Val | Ala | Phe | Ile | Gly | Val | Ile | Gly | Lys | Met |
|     |     |     | 1170 |     |     |     |     | 1175 |     |     |     |     | 1180 |     |     |
| Glu | Gly | Ala | Ser | Ser | Gln | Asn | Ile | Gly | Leu | Ile | Ser | Leu | Ser | Leu | Thr |
| 1185 |     |     |     |     | 1190 |     |     |     |     | 1195 |     |     |     |     | 1200 |
| Met | Ser | Met | Thr | Leu | Thr | Glu | Thr | Leu | Asn | Trp | Leu | Val | Arg | Gln | Val |
|     |     |     |     | 1205 |     |     |     |     | 1210 |     |     |     |     | 1215 |     |
| Ala | Met | Val | Glu | Ala | Asn | Met | Asn | Ser | Val | Glu | Arg | Val | Leu | His | Tyr |
|     |     |     | 1220 |     |     |     |     | 1225 |     |     |     |     | 1230 |     |     |
| Thr | Gln | Glu | Val | Glu | His | Glu | His | Val | Pro | Glu | Met | Gly | Glu | Leu | Val |
|     |     | 1235 |     |     |     |     | 1240 |     |     |     |     | 1245 |     |     |     |

```
Ala Gln Leu Val Arg Ser Glu Ser Gly Arg Gly Ala Asn Val Thr Glu
    1250                1255                1260

Thr Val Val Ile Glu Ser Ala Gly Ala Ala Ser Ser Ala Leu His Pro
1265                1270                1275                1280

Val Gln Ala Gly Ser Leu Val Leu Glu Gly Val Gln Met Arg Tyr Arg
                1285                1290                1295

Glu Gly Leu Pro Leu Val Leu Arg Gly Val Ser Phe Gln Ile Ala Pro
            1300                1305                1310

Arg Glu Lys Val Gly Ile Val Gly Arg Thr Gly Ser Gly Lys Ser Thr
            1315                1320                1325

Leu Leu Leu Thr Phe Met Arg Met Val Glu Val Cys Gly Cys Val Ile
            1330                1335                1340

His Val Asn Gly Arg Glu Met Ser Ala Tyr Gly Leu Arg Glu Leu Arg
1345                1350                1355                1360

Arg His Phe Ser Met Ile Pro Gln Asp Pro Val Leu Phe Asp Gly Thr
                1365                1370                1375

Val Arg Gln Asn Val Asp Pro Phe Leu Glu Ala Ser Ser Ala Glu Val
            1380                1385                1390

Trp Ala Ala Leu Glu Leu Val Gly Leu Arg Glu Arg Val Ala Ser Glu
            1395                1400                1405

Ser Glu Gly Ile Asp Ser Arg Val Leu Glu Gly Gly Ser Asn Tyr Ser
        1410                1415                1420

Val Gly Gln Arg Gln Leu Met Cys Met Ala Arg Ala Leu Leu Lys Arg
1425                1430                1435                1440

Gly Ser Gly Phe Ile Leu Met Asp Glu Ala Thr Ala Asn Ile Asp Pro
                1445                1450                1455

Ala Leu Asp Arg Gln Ile Gln Ala Thr Val Met Ser Ala Phe Ser Ala
            1460                1465                1470

Tyr Thr Val Ile Thr Ile Ala His Arg Leu His Thr Val Ala Gln Tyr
            1475                1480                1485

Asp Lys Ile Ile Val Met Asp His Gly Val Val Ala Glu Met Gly Ser
    1490                1495                1500

Pro Arg Glu Leu Val Met Asn His Gln Ser Met Phe His Ser Met Val
1505                1510                1515                1520

Glu Ser Leu Gly Ser Arg Gly Ser Lys Asp Phe Tyr Glu Leu Leu Met
                1525                1530                1535

Gly Arg Arg Ile Val Gln Pro Ala Val Leu Ser Asp
            1540                1545
```

( 2 ) INFORMATION FOR SEQ ID NO:8:

( i ) SEQUENCE CHARACTERISTICS:
      ( A ) LENGTH: 309 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
Leu Lys Asp Ile Asn Phe Lys Ile Glu Arg Gly Gln Leu Leu Ala Val
1               5                   10                  15

Ala Gly Ser Thr Gly Ala Gly Lys Thr Ser Leu Leu Met Met Ile Met
            20                  25                  30

Gly Glu Leu Glu Pro Ser Glu Gly Lys Ile Lys His Ser Gly Arg Ile
        35                  40                  45
```

```
Ser  Glu  Cys  Ser  Gln  Phe  Ser  Trp  Ile  Met  Pro  Gly  Thr  Ile  Lys  Glu
     50                      55                      60

Asn  Ile  Ile  Phe  Gly  Val  Ser  Tyr  Asp  Glu  Tyr  Arg  Tyr  Arg  Ser  Val
65                       70                      75                           80

Ile  Lys  Ala  Cys  Gln  Leu  Glu  Glu  Asp  Ile  Ser  Lys  Phe  Ala  Glu  Lys
                    85                      90                      95

Asp  Asn  Ile  Val  Leu  Gly  Glu  Gly  Ile  Thr  Leu  Ser  Gly  Gly  Gln
                    100                     105                     110

Arg  Ala  Arg  Ile  Ser  Leu  Ala  Arg  Ala  Val  Tyr  Lys  Asp  Ala  Asp  Leu
               115                     120                     125

Tyr  Leu  Leu  Asp  Ser  Pro  Phe  Gly  Tyr  Leu  Asp  Val  Leu  Thr  Glu  Lys
     130                     135                     140

Glu  Ile  Phe  Glu  Ser  Cys  Leu  Glu  Asn  Ile  Ser  Phe  Ser  Ile  Ser  Pro
145                          150                     155                     160

Gly  Gln  Arg  Val  Gly  Leu  Leu  Gly  Arg  Thr  Gly  Ser  Gly  Lys  Ser  Thr
                    165                     170                     175

Leu  Leu  Ser  Ala  Phe  Leu  Arg  Leu  Leu  Asn  Thr  Glu  Gly  Glu  Ile  Gln
                    180                     185                     190

Ile  Asp  Gly  Val  Ser  Trp  Asp  Ser  Ile  Thr  Leu  Gln  Gln  Trp  Arg  Lys
               195                     200                     205

Ala  Phe  Gly  Val  Ile  Pro  Gln  Lys  Val  Phe  Ile  Phe  Ser  Gly  Thr  Phe
     210                     215                     220

Arg  Lys  Asn  Leu  Asp  Pro  Tyr  Glu  Gln  Trp  Ser  Asp  Gln  Glu  Ile  Trp
225                          230                     235                     240

Lys  Val  Ala  Asp  Glu  Val  Gly  Leu  Arg  Ser  Val  Ile  Glu  Gln  Phe  Pro
                    245                     250                     255

Gly  Lys  Leu  Asp  Phe  Val  Leu  Val  Asp  Gly  Gly  Cys  Val  Leu  Ser  His
                    260                     265                     270

Gly  His  Lys  Gln  Leu  Met  Cys  Leu  Ala  Arg  Ser  Val  Leu  Ser  Lys  Ala
          275                     280                     285

Lys  Ile  Leu  Leu  Leu  Asp  Glu  Pro  Ser  Ala  His  Leu  Asp  Pro  Val  Thr
     290                     295                     300

Tyr  Gln  Ile  Ile  Arg
305
```

( 2 ) INFORMATION FOR SEQ ID NO:9:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

```
Leu  Lys  Gly  Leu  Asn  Leu  Lys  Val  Gln  Ser  Gly  Gln  Thr  Val  Ala  Leu
1                   5                       10                      15

Val  Gly  Asn  Ser  Gly  Cys  Gly  Lys  Ser  Thr  Thr  Val  Gln  Leu  Met  Gln
               20                      25                      30

Arg  Leu  Tyr  Asp  Pro  Thr  Glu  Gly  Met  Val  Ser  Val  Asp  Gly  Gln  Asp
          35                      40                      45

Ile  Arg  Thr  Ile  Asn  Val  Arg  Phe  Leu  Arg  Glu  Ile  Ile  Gly  Val  Val
     50                      55                      60

Ser  Gln  Glu  Pro  Val  Leu  Phe  Ala  Thr  Thr  Ile  Ala  Glu  Asn  Ile  Arg
65                      70                      75                           80
```

```
Tyr Gly Arg Glu Asn Val Thr Met Asp Glu Ile Glu Lys Ala Val Lys
            85              90              95

Glu Ala Asn Ala Tyr Asp Phe Ile Met Lys Leu Pro His Lys Phe Asp
            100             105             110

Thr Leu Val Gly Glu Arg Gly Ala Gln Leu Ser Gly Gly Gln Lys Gln
        115             120             125

Arg Ile Ala Ile Ala Arg Ala Leu Val Arg Asn Pro Lys Ile Leu Leu
    130             135             140

Leu Asp Glu Ala Thr Ser Ala Leu Asp Thr Glu Ser Glu Ala Val Val
145             150             155             160

Gln Val Ala Leu Leu Gln Gly Leu Ser Leu Glu Val Lys Lys Gly Gln
            165             170             175

Thr Leu Ala Leu Val Gly Ser Ser Gly Cys Gly Lys Ser Thr Val Val
        180             185             190

Gln Leu Leu Glu Arg Phe Tyr Asp Pro Leu Ala Gly Lys Val Leu Leu
        195             200             205

Asp Gly Lys Glu Ile Lys Arg Leu Asn Val Gln Trp Leu Arg Ala His
    210             215             220

Leu Gly Ile Val Ser Gln Glu Pro Ile Leu Phe Asp Cys Ser Ile Ala
225             230             235             240

Glu Asn Ile Ala Tyr Gly Asp Asn Ser Arg Val Val Ser Gln Glu Glu
            245             250             255

Ile Val Arg Ala Ala Lys Glu Ala Asn Ile His Ala Phe Ile Glu Ser
            260             265             270

Leu Pro Asn Lys Tyr Ser Thr Lys Val Gly Asp Lys Gly Thr Gln Leu
        275             280             285

Ser Gly Gly Gln Lys Gln Arg Ile Ala Ile Ala Arg Ala Leu Val Arg
    290             295             300

Gln Pro His Ile Leu Leu Leu Asp Glu Ala Thr Ser Ala Leu Asp Thr
305             310             315             320

Glu Ser Glu Lys Val Val Gln
            325
```

1

ISOLATED NUCLEIC ACID MOLECULES ENCODING MULTIDRUG RESISTANCE PROTEINS

CROSS REFERENCE TO RELATED APPLICATIONS

This application is a continuation-in-part of application Ser. No. 08/407,207 filed Mar. 20, 1995, pending, which is a continuation-in-part of application Ser. No. 08/141,893 filed Oct. 26, 1993, now U.S. Pat. No. 5,489,519, issued Feb. 6, 1996, which is a continuation-in-part of application Ser. No. 08/029,340 filed Mar.8, 1993, now abandoned, which is a continuation-in-part of application Ser. No. 07/966,923 filed Oct. 27, 1992, now abandoned, the entire contents of each of which are incorporated herein by reference.

BACKGROUND OF THE INVENTION

It is well known that many types of cancer regress initially in response to currently available drugs. However, if the disease should recur, as it does with variable frequency, it is often refractory to further treatment with either the agent originally used for treatment or agents to which the patient has not been previously exposed. Currently there is little that can be done for patients whose tumors display this form of multidrug resistance.

One mechanism by which cancer cells can simultaneously develop resistance to an array of structurally diverse drugs has been elucidated over the last 15 years with the characterization of P-glycoprotein.

P-glycoprotein is a member of a superfamily of membrane proteins that serve to transport a variety of molecules, ranging from ions to proteins, across cell membranes. This superfamily is known as the ATP-binding cassette (ABC) superfamily of membrane transport proteins. For a review see C. F. Higgins, *Ann. Rev. Cell Biol.* 8, 67 (1992). For example, in addition to P-glycoprotein which transports chemotherapeutic drugs, this family includes the cystic fibrosis transmembrane conductance regulator, which controls chloride ion fluxes, as well as insect proteins that mediate resistance to antimalarial drugs. P-glycoprotein is believed to confer resistance to multiple anticancer drugs by acting as an energy dependent efflux pump that limits the intracellular accumulation of a wide range of cytotoxic agents and other xenobiotics. Compounds that are excluded from mammalian cells by P-glycoprotein are frequently natural product-type drugs but other large heterocyclic molecules are also "substrates" for this efflux pump.

The discovery of P-glycoprotein and its occurrence in a variety of tumor types has stimulated the search for compounds that are capable of blocking its function and consequently, of reversing resistance. These investigations have resulted in identification of a large number of so-called chemosensitizers or reversing agents. Some of these compounds act by inhibiting the pumping action of P-glycoprotein while the mechanism of action of others is still undetermined. A select group of these agents are currently under intensive clinical investigation and they show considerable promise as adjuncts to conventional chemotherapy. Chemosensitizers which can reverse P-glycoprotein-mediated multidrug resistance include verapamil and cyclosporin A.

Unfortunately, overexpression of P-glycoprotein does not explain the high frequency of multidrug resistance in some of the more prevalent forms of cancer, such as lung cancer. In the Western world, lung cancer accounts for approximately 30% of total cancer deaths. There are four major histological categories of lung tumors: epidermoid or squamous cell adenocarcinomas, large cell carcinomas, adenocarcinomas and small cell carcinomas. The first three categories, known collectively as non-small cell lung cancers, differ from the last in their initial response to chemotherapy and radiotherapy. Non-small cell lung cancers are relatively resistant to both forms of treatment from the outset. In contrast, small cell lung cancer, which accounts for 20% of all lung tumors, exhibits a high initial response rate (80-90% in limited disease) to chemotherapy. However, almost all patients relapse with a multidrug resistant form of the disease and two year survival rates are less than 10%. Although the drug resistance profile displayed in relapsed small cell lung cancer patients is similar to that conferred by P-glycoprotein, P-glycoprotein appears not to be involved. In addition, limited studies in cell culture and in patients indicate that multidrug resistance in small cell lung cancer does not respond to chemosensitizers, such as verapamil and cyclosporin A, that show promise with other types of drug resistant tumors.

Survival rates in lung cancer have not improved significantly in forty years and, because of its common occurrence, there is clearly a great need for improved therapy for this disease.

SUMMARY OF THE INVENTION

The present invention is based, at least in part, on the discovery of a nucleic acid which encodes a protein which can confer multidrug resistance on a drug sensitive mammalian cell when expressed in the cell and which is overexpressed in certain multidrug resistant cancer cell lines. The nucleic acid of the invention was isolated from a multidrug resistant cancer cell line which does not overexpress P-glycoprotein and whose resistance is not substantially reversed by chemosensitizers which inhibit P-glycoprotein. The nucleic acid and encoded protein of the present invention represent molecules which can be targeted therapeutically in multidrug resistant tumors expressing the nucleic acid and protein.

The present invention provides an isolated nucleic acid having a nucleotide sequence which encodes a protein associated with multidrug resistance which is overexpressed in multidrug resistant cells independently of overexpression of P-glycoprotein. The protein has been named multidrug resistance-associated protein (referred to as MRP). The protein of the invention differs in amino acid sequence from P-glycoprotein. The isolated nucleic acid, when expressed in a cell which is not multidrug resistant, can confer on the cell multidrug resistance.

In a preferred embodiment, an isolated nucleic acid is provided having a sequence which codes for a protein associated with multidrug resistance having an amino acid sequence which has substantial sequence homology with the amino acid sequence shown in SEQ ID NO:2. Most preferably the isolated nucleic acid has a sequence having substantial sequence homology with the nucleotide sequence shown in SEQ ID NO:1. In one embodiment, the invention provides an isolated human MRP nucleic acid molecule, as shown in SEQ ID NO: 1 and encoding a human MRP protein as shown in SEQ ID NO: 2. In another embodiment, the invention provides a natural variant of the human MRP nucleic acid molecule of SEQ ID NO: 1, shown in SEQ ID NO: 3 and encoding a human MRP protein shown in SEQ ID NO: 4, which differs by three nucleotide base pairs from the sequence of SEQ ID NO: 1. In yet another embodiment, the invention provides an isolated mouse MRP nucleic acid molecule, as shown in SEQ ID NO: 5 and encoding a mouse MRP protein as shown in SEQ ID NO: 6. The invention further provides an isolated nucleic acid which is antisense to a nucleic acid having substantial sequence homology with the nucleotide sequence shown in SEQ ID NO:1.

The invention further provides a recombinant expression vector adapted for transformation of a host cell comprising the nucleic acid of the invention operatively linked to a regulatory sequence. The invention also provides a recombinant expression vector adapted for transformation of a host cell comprising a DNA molecule operatively linked to a regulatory sequence to allow expression of an RNA molecule which is antisense to a nucleotide sequence of SEQ ID NO: 1.

The invention also provides a method of preparing a protein capable of conferring multidrug resistance utilizing the nucleic acid of the invention. The method comprises culturing a transformant host cell including a recombinant expression vector comprising a nucleic acid of the invention and an regulatory sequence operatively linked to nucleic acid in a suitable medium until a multidrug resistance protein is formed and thereafter isolating the protein.

The invention further provides an isolated protein having the biological activity of MRP, which can confer multidrug resistance on a drug sensitive cell when the protein is expressed in the cell, said resistance not being substantially reversed by chemosensitizers of P-glycoprotein. The isolated protein of the invention is associated with multidrug resistance in tumor cells and is overexpressed in multidrug resistant cells which may or may not overexpress P-glycoprotein. In a preferred embodiment the protein has an amino acid sequence which has substantial homology with the amino acid sequence shown in SEQ ID NO: 2.

The invention further provides an antibody specific for an epitope of a protein of the invention. Preferably the antibody is a monoclonal antibody. The antibody can be coupled to a detectable substance or a substance having toxic or therapeutic activity. The invention also provides a bispecific antibody capable of binding to a tumor cell which expresses a protein of the invention and to a detectable substance, or a substance having toxic or therapeutic activity. Preferably, the toxic substance is a cytotoxic cell and the bispecific antibody is capable of crosslinking the tumor cell and the cytotoxic cell thereby facilitating lysis of the tumor cell. The invention further provides a tetrameric antibody complex of a first monoclonal antibody which is capable of binding to a tumor cell expressing a protein of the invention and a second monoclonal antibody which is capable of binding to a detectable substance or a substance having toxic or therapeutic activity wherein the first and second antibody are from a first animal species, conjugated to form a cyclic tetramer with two monoclonal antibodies of a second animal species directed against the Fc fragment of the antibodies of the first animal species.

The antibodies, bispecific antibodies or tetrameric antibody complexes can be incorporated in compositions suitable for administration in a pharmaceutically acceptable carrier.

Molecules which bind to a protein of the invention, including the antibodies, bispecific antibodies and tetrameric antibody complexes of the invention, can be used in a method for identifying multidrug resistant tumor cells by labelling the molecule with a detectable substance, contacting the molecule with tumor cells and detecting the detectable substance bound to the tumor cells. A molecule which binds to a protein of the invention can further be used in a method for inhibiting multidrug resistance of a cell by blocking activity of an MRP protein A molecule which binds to a protein of the invention can further be used to kill a multidrug resistant cell which expresses the protein by contacting the molecule, coupled to a toxic or therapeutic substance, with the multidrug resistant cell.

Nucleic acids of the invention can be used in a method for protecting a drug sensitive cell from cytotoxicity due to exposure to a drug by transfecting the cell with a nucleic acid in a form suitable for expression of the protein encoded by the nucleic acid in the cell, thereby conferring drug resistance on the cell.

The recombinant molecules of the invention can be used to produce transformant host cells expressing the protein of the invention. The recombinant molecules of the invention can be also used to produce transgenic nonhuman animals and nonhuman knockout animals. The transfected cells, transgenic animals and knockout animals can be used to test substances for their effect on multidrug resistance. A method for identifying a substance which is a chemosensitizer of a therapeutic agent and a method for identifying a cytotoxic substance for multidrug resistant cells, using transformant host cells or animals of the invention, are provided.

The invention also relates to a cell line which is multidrug resistant, does not overexpress P-glycoprotein and is substantially resistant to hydrophobic drugs. The cell line may be derived from small cell lung cancer cells, preferably the cell line NCI-H69. Most preferably the multidrug resistant cell line is H69AR (ATCC CRL 11351). A revertant drug sensitive cell line may be obtained from the multidrug resistant cell line by culturing the multidrug resistant cell line in the absence of a drug for a period of time sufficient to produce a revertant drug sensitive cell line. Preferably the revertant drug sensitive cell line is H69PR (ATCC CRL 11350).

BRIEF DESCRIPTIONS OF THE DRAWINGS

FIG. 1C is a Northern blot of sensitive and resistant HeLa cell poly (A⁺)RNA hybridized with a 1.8 kb EcoRI cDNA fragment of the multidrug resistance protein of the invention.

FIGS. 3A-1 to 3A-5 show the complete amino acid sequence of the multidrug resistance protein of the invention (Hum/MRP, SEQ ID NO: 2) aligned with the complete amino acid sequence of ltPgpA (Lei/PgpA, SEQ ID NO: 3).

FIG. 3B and 3B-1 show a diagram showing the alignment of the extended nucleotide binding regions of the multidrug resistance protein of the invention (Hum/MRP, residues 661–1469 of SEQ ID NO: 2), human CFTR (Hum/CFTR, SEQ ID NO: 2) and leishmania ltPgpA (Lei/PgpA, residues 650–1463 of SEQ ID NO: 7) and human P-glycoprotein (Hum/Mdr1, SEQ ID NO: 9).

FIG. 4 is a Northern blot of total RNA from normal tissues hybridized with a 0.9 kb EcoRI cDNA fragment of the multidrug resistance protein of the invention.

FIG. 5 is an ISCN-derived idiogram of the human karyotype showing silver grain distribution following in situ hybridization of a 1.8 kb EcoRI cDNA fragment of the multidrug resistance protein of the invention to metaphase chromosomes.

Figure 11A:
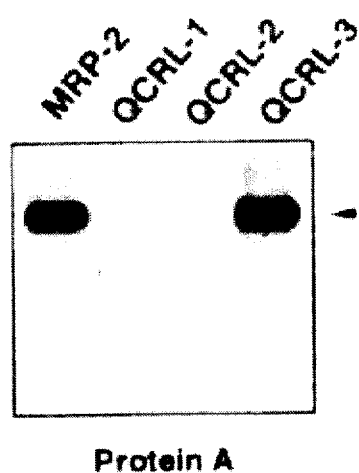
Figure 11B:
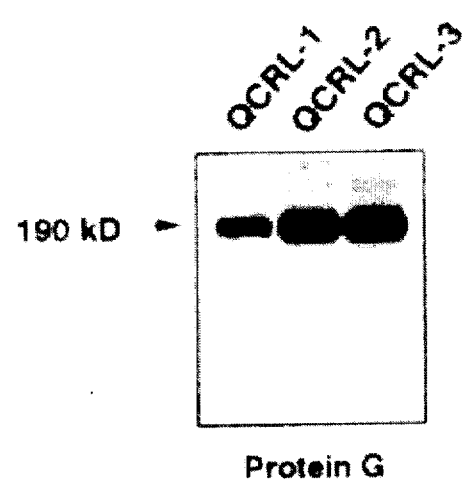

FIGS. 11A-B are photographs of immunoprecipitation autoradiographs of labelled proteins from H69AR cells immunoprecipitated with anti-MRP mAbs (QCRL-1, -2 or -3) or anti-MRP peptide antisera (MRP-2). Immune complexes were precipitated with protein A-Sepharose (panel A) or protein G-Sepharose (panel B).

FIGS. 12A-C are photographs of Western blots of proteins from membrane-enriched fractions of MRP-overexpressing cells (H69AR and T5), P-glycoprotein-overexpressing cells (8226/Dox40) or control cells (H69, H69PR and C1) screened with an anti-MRP mAb (QCRL-1) (panels A and B) or an anti-Pgp mAb (C219) (panel C).

Figure 13:
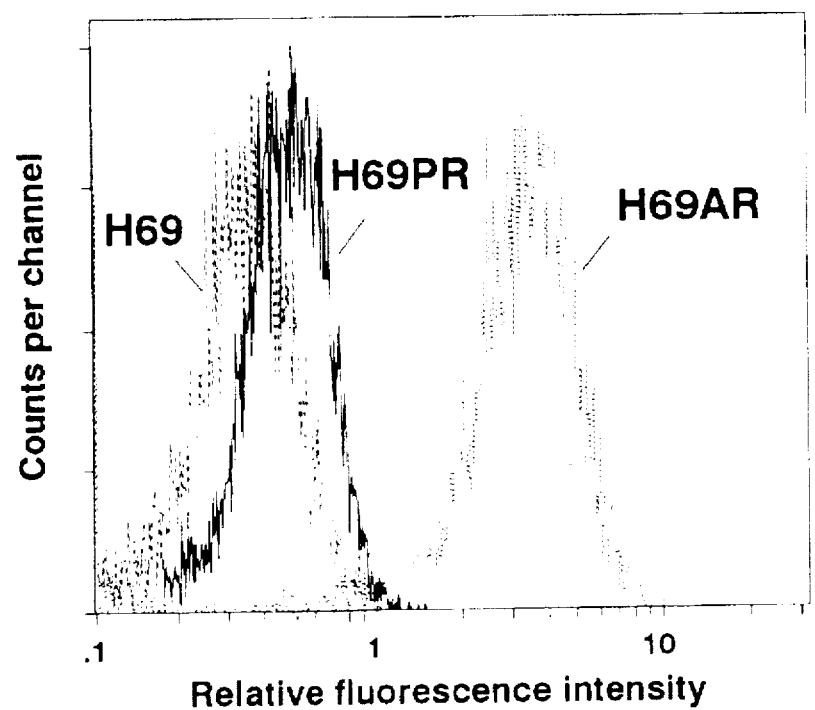
Figure 13B:
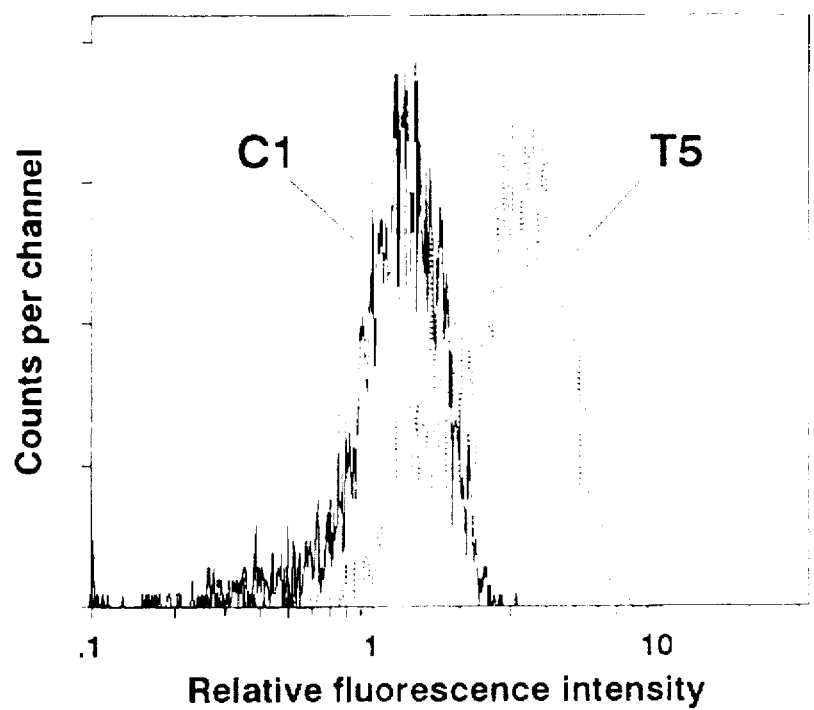

FIGS. 13A-B are flow cytometric profiles of fixed H69, H69AR or H69PR cells (panel A) or fixed T5 or C1 cells (panel B) reacted with anti-MRP mAb QCRL-3.

DETAILED DESCRIPTION OF THE INVENTION

Multidrug resistant mammalian cell lines have been derived from a number of tumor types and have provided in vitro models for the study of acquired resistance. Although selected by a single natural product-type drug, these cell lines are cross-resistant to a wide range of chemically unrelated xenobiotics with multiple subcellular targets. Typically, these cells are resistant to anthracyclines [e.g. doxorubicin (DOX), epipodophyllotoxins (e.g. VP-16) and the Vinca alkaloids (e.g. vinblastine)] but not to antimetabolites such as 5-fluorouracil, or to platinum-containing drugs. Multidrug resistant cells also frequently exhibit a collateral sensitivity to certain hydrophobic drugs including local anesthetics and steroid hormones.

The most commonly reported alteration in multidrug resistant tumor cells has been the increased expression of the 170 kDa plasma membrane glycoprotein, P-glycoprotein (P-gp), which is encoded by the MDR1 gene. Studies carried out in several laboratories with clinical samples and cell lines representing many tumor types have lead to the conclusion that P-gp, while clinically relevant in some malignancies, is unlikely to be important in others. Overexpression of P-gp is an infrequent occurrence in both small cell lung cancer (SCLC) and non small cell lung cancer (NSCLC).

One of the most widely used cell lines in experimental studies of SCLC is NCI-H69 (H69) (Gazdar et al., *Cancer Res.* 40, 3502–3507 (1980)) (ATCC HTB 119). This cell line was treated repeatedly with an anthracycline, such as daunorubicin or epirubicin and preferably DOX, and step-wise selected to a final concentration of 0.8 µM, to produce a multidrug resistant cell line, designated as H69AR. A description of the procedures which can be used to produce a multidrug resistant cell line such as H69AR is found in Cole, *Cancer Chemother Pharmacol.* 17, 259–263 (1986) and in Mirski et al., *Cancer Research* 47, 2594–2598 (1987).

The H69AR cell line (ATCC CRL 11351) is about 50-fold resistant to DOX as compared to the parental H69 cell line. H69AR is also cross-resistant to a wide variety of natural product-type drugs. On the other hand, drugs such as carboplatin, 5-fluorouracil and bleomycin are equally toxic to both sensitive H69 and resistant H69AR cells. Although the cross-resistance pattern of H69AR cells is typical of resistance associated with increased levels of P-gp, these cells are different in that they display little or no collateral sensitivity to hydrophobic drugs such as steroids or local anaesthetics. Another distinguishing feature of H69AR of potential clinical relevance that distinguishes it from P-gp overexpressing cell lines is the limited ability of verapamil, cyclosporin A and other chemosensitizing agents that interact with P-gp, to reverse DOX resistance in these cells. The absence of P-gp overexpression supports the suggestion that H69AR provides a clinically relevant model of drug resistance in lung cancer.

A revertant drug sensitive cell line H69PR (Cole et al., *Br J. Cancer* 65, 498–502, 1992) (ATCC CRL 11350) was isolated by culturing the H69AR cell line in the absence of drugs such as DOX for a sufficient time to produce a revertant cell line. Preferably the cell line H69PR is cultured in the absence of drugs for at least 3 months and up to about 48 months, most preferably 42 months.

The cell lines of the invention may be used to assay for a substance that affects a multidrug resistant tumor cell. Cells from a cell line of the invention may be incubated with a test substance which is suspected of affecting multidrug resistance. The effect of the substance can be determined by analyzing the drug resistance pattern of the cells and comparing the results to a control. As discussed above, the multidrug resistant cell line of the invention is resistant to anthracyclines, epipodophyllotoxins, Vinca alkaloids and other natural-product type drugs. Thus, it is possible to screen for an agonist or antagonist substance of multidrug resistance or an antagonist that inhibits the effects of an agonist.

In an embodiment of the invention, a substance that is suspected of being cytotoxic to a multidrug resistant tumor cell can be identified. Therefore, it is possible using the above described method to identify substances which may be useful in the treatment of multidrug resistant tumors.

As described in the Examples, the H69AR cell line has been used to identify a cDNA encoding a novel protein associated with multidrug resistance designated MRP. The DNA sequence and deduced amino acid sequence of MRP are shown in SEQ ID NO:1 and SEQ ID NO. 2, respectively. MRP mRNA is overexpressed in certain multidrug resistant tumor cell lines, including H69AR. Furthermore, expression of MRP protein in a drug sensitive mammalian cell line confers multidrug resistance on the cell line A protein described herein as "having biological activity of MRP" can confer on a mammalian cell multidrug resistance to anthracyclines, epipodophyllotoxins and Vinca alkaloids when the protein is expressed in the mammalian cell, and this resistance is not substantially reversed by chemosensitizers which reverse P-glycoprotein-mediated multidrug resistance, such as verapamil or cyclosporin A, in an MRP-dependent manner.

The terms "drug resistant" or "drug resistance" as used herein to describe a property of a cell refer to the ability of the cell to withstand without cytotoxicity increased concentrations of a drug as compared to an appropriate control cell. An appropriate control cell for a cell which has been made drug resistant by continued exposure to a drug is the parental cell from which the drug resistant cell was derived. An appropriate control cell for a cell which has been made drug resistant by expression in the cell of a protein which confers drug resistance on the cell is the same cell without the protein expressed. Appropriate control cells for naturally occurring tumor cells in vivo made drug resistant by continued exposure to a drug are the same tumor cells at the time of initial exposure to the drug.

The invention provides isolated nucleic acids encoding proteins having biological activity of MRP. In a preferred embodiment, the nucleic acid is a cDNA comprising a nucleotide sequence shown in SEQ ID NO: 1. The invention further provides antisense nucleic acids of nucleic acids encoding proteins having biological activity of MRP. The invention further provides recombinant expression vectors comprising the nucleic acids and antisense nucleic acids of the invention and transformant host cells containing recombinant nucleic acids of the invention The invention provides isolated proteins having biological activity of MRP and a method for preparing such proteins. In a preferred embodiment, the isolated protein having biological activity of MRP comprises an amino acid sequence shown in SEQ ID NO: 2. The protein comprising the amino acid sequence of SEQ ID NO: 2 is a member of the ABC superfamily of membrane transport proteins. The invention further provides antibodies specific for the isolated proteins of the invention and compositions suitable for administration comprising such antibodies. The invention further provides transgenic and knockout nonhuman animals produced using the nucleic acids of the invention.

The invention provides a method for identifying multidrug resistant cell using the nucleic acids and antibodies of the invention. The invention further provides methods for inhibiting multidrug resistance of a multidrug resistant cell and for killing a multidrug resistant cell using the nucleic acids and antibodies of the invention. The invention further provides methods for identifying substances which are chemosensitizers of therapeutic agents or cytotoxic to drug resistant cells using the transformant host cells and animals of the invention. Furthermore, the invention provides diagnostic kits for identifying drug resistant tumor cells.

These and other aspects of this invention are described in detail in the following subsections.

I. Isolated Nucleic Acids

The invention provides isolated nucleic acids encoding proteins having biological activity of MRP. The term "isolated" refers to a nucleic acid substantially free of cellular material or culture medium when produced by recombinant DNA techniques, or chemical precursors or other chemicals when chemically synthesized. An "isolated" nucleic acid is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded. In a preferred embodiment, the nucleic acid is a cDNA comprising a nucleotide sequence shown in SEQ ID NO: 1. In another embodiment, the nucleic acid is a cDNA comprising the coding region of the nucleotide sequence shown in SEQ ID NO: 1. In another embodiment, the nucleic acid encodes a protein comprising an amino acid sequence shown in SEQ ID NO: 2.

It will be appreciated that the invention includes nucleic acids having substantial sequence homology with the nucleotide sequence shown in SEQ ID NO: 1 or encoding proteins having substantial homology to the amino acid sequence shown in SEQ ID NO: 2. Homology refers to sequence similarity between sequences and can be determined by comparing a position in each sequence which may be aligned for purposes of comparison. When a position in the compared sequence is occupied by the same nucleotide base or amino acid, then the molecules are homologous at that position. A degree of homology between sequences is a function of the number of matching or homologous positions shared by the sequences. Examples of sequences having substantial homology to that of SEQ ID NOs: 1 and 2 are naturally-occurring variants thereof from the same species (i.e., humans, from which the nucleic acid of SEQ ID NO: 1 is derived) and homologues from other species (e.g., non-human mammalian forms of MRP). Regarding the former, in one embodiment the invention provides a natural human MRP variant having the nucleotide and encoded amino-acid sequences shown in SEQ ID NOs: 3 and 4, respectively. This variant differs from in nucleotide sequence from that of SEQ ID NO: 1 at three nucleotide positions: 2249 (a change from T to C), 4039 (a change from C to G) and 4040 (a change from G to C). These nucleotide changes in this human variant lead to two changes in the amino acid sequence of the encoded MRP protein, one at position 685 (a change from a Leu to a Ser) and the other at position 1282 (a change from an Arg to an Ala). Regarding species homologues of the human MRP sequence of SEQ ID NO: 1, in another embodiment the invention provides a murine nucleic acid molecule encoding a murine MRP. The nucleotide sequence and encoded amino acid sequence of a murine MRP cDNA is shown in SEQ ID NOs: 5 and 6, respectively. The human and murine MRP proteins exhibit 88% amino acid identity. The strongest conservation between the two protein is within a stretch of amino acid residues located at positions 1126 to 1239 of the human MRP protein and positions 1123 to 1236 of the mouse MRP protein.

The term "sequences having substantial sequence homology" means those nucleotide and amino acid sequences which have slight or inconsequential sequence variations from the sequences disclosed in SEQ ID NO:1 and SEQ ID NO: 2. i.e. the homologous nucleic acids function in substantially the same manner to produce substantially the same polypeptides as the actual sequences. The variations may be attributable to local mutations or structural modifications. It is expected that substitutions or alterations can be made in various regions of the nucleotide or amino acid sequence without affecting protein function. particularly if they lie outside the regions predicted to be of functional significance.

Analysis of the protein encoded by SEQ ID NO: 1. comprising the amino acid sequence of SEQ ID NO: 2. reveals 12 hydrophobic stretches predicted to be membrane-spanning regions and of functional importance. These amino acid residues correspond to positions 99–115. 137–153. 175–191, 365–381, 444–460, 466–482, 555–571, 591–607, 969–985, 1028–1044, 1102–1118 and 1205–1221 of SEQ ID NO: 2. Nucleotide substitutions that result in amino acid sequence changes within these regions. especially those that reduce the hydrophobic nature of these regions. are not likely to be translated into a functional protein.

Analysis of the protein encoded by SEQ ID NO: 1. comprising the amino acid sequence of SEQ ID NO: 2. reveals two regions having the structural characteristics of nucleotide binding folds (NBFs) typical of ATP-binding cassette domains (ABC domains). See Hyde. S. C. et al.. *Nature* 346, 362–365 (1990). Elements comprising part of the structure of these NBFs are conserved in other members of the ABC superfamily of membrane transport proteins and the domains have been shown to bind nucleotides and to be functionally important. For example see Higgins. C. F., *Ann. Rev. Cell Biol.* 8, 67–113 (1992). In the protein comprising the amino acid sequence shown in SEQ ID NO: 2, the two NBFs are located between about amino acid residues 661–810 and 1310–1469 of SEQ ID NO:2. Nucleotide and corresponding amino acid substitutions which decrease the degree of homology of these regions compared to other members of the ABC superfamily of membrane transport proteins are likely not to be tolerated in a functional protein. Alternatively, nucleotide and corresponding amino acid substitutions which maintain the structure of an NBF are likely to be tolerated. For example, it has been demonstrated that nucleotides encoding an NBF of one member of the ABC superfamily of membrane transport proteins can be substituted for the homologous domain of another member while maintaining function of the protein. See Buschman. F. and Gros. P. *Mol. Cell Biol.* 11, 595–603 (1991). Accordingly, the invention provides for a nucleic acid encoding a protein comprising an amino acid sequence represented by V-W-X-Y-Z, wherein V are amino acid residues corresponding to amino acid residues from about 1 to 660 of SEQ ID NO: 2, W are amino acid residues of an NBF substantially homologous with amino acid residues from about 661 to 810 of SEQ ID NO: 2, X are amino acid residues corresponding to amino acid residues from about 811 to 1309 of SEQ ID NO: 2, Y are amino acid residues of an NBF substantially homologous with amino acid residues from about 1310 to 1469 of SEQ ID NO: 2 and Z are amino acid residues corresponding to amino acid residues from about 1470 to 1531 of SEQ ID NO: 2. The term "from about" is intended to mean that the junction between two regions of the protein (e.g. between V and W) may vary by a few amino acids from those specifically indicated.

It is anticipated that. outside of the regions specified above. a nucleic acid encoding a protein comprising an amino acid sequence which is about 50% similar with the amino acid sequence shown SEQ ID NO:2 will provide functional proteins. Alternatively. proteins comprising an amino acid sequence which is 60%, 70%, 80% or 90% homologous with the amino acid sequence shown SEQ ID NO:2 may provide proteins having MRP activity. The invention encompasses a nucleic acid encoding a protein having biological activity of MRP which is at least 50% homologous with the amino acid sequence of SEQ ID NO: 2. Specific examples of such additional nucleic acid molecules encoded by the invention include the human MRP variant shown in SEQ ID NOs: 3 (which differs in nucleotide sequence from that of SEQ ID NO: 1 by only three nucleotide base pairs) and the mouse MRP cDNA shown in SEQ ID: 5 (which encodes a mouse MRP protein. shown in SEQ ID NO: 6, which is 88% identical in amino acid sequence to the human MRP protein of SEQ ID NO: 2).

It will further be appreciated that variant forms of the nucleic acids of the invention which arise by alternative splicing of an mRNA corresponding to a cDNA of the invention are encompassed by the invention. Hybridization of a cDNA of the invention. containing all or part of SEQ ID NO: 1. to cellular RNA identifies an mRNA of approximately 6.5 kb with an extended open reading frame of 1531 amino acids. Several cDNA clones have been isolated that contain internal deletions which maintain the original reading frame, suggesting that they may be produced by alternative splicing. The existence of mRNA species containing these deletions was confirmed by reverse PCR of RNA from both multidrug resistant and sensitive cells. In most cases. the variant mRNAs represent minor components of 10% or less. However. some comprise more than 20% of total MRP mRNA. Alternative splice forms have been identified which remove nucleotides 657 to 783 of SEQ ID NO: 1 (amino acids 155–196 inclusive of SEQ ID NO: 2), 1845 to 1992 (amino acids 551–599 inclusive), 2287 to 2463 (amino acids 698–756 inclusive), 2287 to 2628 (amino acids 698–811 inclusive) and 4230 to about 4818 (amino acids 1346 to 1531 inclusive). Two of the more common variants lack segments of the $NH_2$ proximal NBF. Both begin at the same site (amino acid 698) and they affect regions of the cassette that are very near and COOH proximal to the common exon 9 splicing variant of the cystic fibrosis transmembrane conductance regulator (CFTR) mRNA. See Chu, C-S. et al., *EMBO Journal* 10, 1355–1363 (1991). The shorter of the two (amino acids 698–756) eliminates a phenylalanine at a position corresponding to F508 of CFTR. The longer one (amino acids 698–811) removes the active transport family signature that includes the conserved LSGGQ sequence and the Walker B motif. Another of the more common variants (amino acids 1346–1531) lacks a region specifying a segment of the protein close to the COOH terminus, similar to the location affected by alternative splicing of exon 23 of CFTR mRNA. See Yoshimura, K., et al. *J. Biol. Chem.* 268, 686–690 (1993). In addition, two other deletions have been identified, one of which eliminates two of the transmembrane domains in the NH2 proximal half of the molecule (amino acids 551–599), and another which removes a potential secretory signal cleavage site located between amino acids 189/190 (amino acids 155–196).

Another aspect of the invention provides a nucleic acid which hybridizes under high or low stringency conditions to a nucleic acid which encodes a protein having all or a portion of an amino acid sequence shown SEQ ID NO:2. Appropriate stringency conditions which promote DNA hybridization, for example, 6.0×sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C. to high stringency conditions, at about 65° C.

Isolated nucleic acids encoding a protein having the biological activity of MRP, as described herein, and having a sequence which differs from a nucleotide sequence shown in SEQ ID NO:1 due to degeneracy in the genetic code are also within the scope of the invention. Such nucleic acids encode functionally equivalent proteins (e.g., a protein having MRP activity) but differ in sequence from the sequence of SEQ ID NO: 1 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of an MRP protein (especially those within the third base of a codon) may result in "silent" mutations in the DNA which do not affect the amino acid encoded. However, it is expected that DNA sequence polymorphisms that do lead to changes in the amino acid sequences of an MRP protein will exist within a population. It will be appreciated by one skilled in the art that these variations in one or more nucleotides (up to about 3–4% of the nucleotides) of the nucleic acids encoding proteins having the biological activity of MRP may exist among individuals within a population due to natural allelic variation. Any and all such nucleotide variations and resulting amino acid polymorphisms are within the scope of the invention. Furthermore, there may be one or more isoforms or related, cross-reacting family members of MRP described herein. Such isoforms or family members are defined as proteins related in biological activity and amino acid sequence to MRP, but encoded by genes at different loci.

An isolated nucleic acid of the present invention encoding a protein having the biological activity of MRP can be isolated from a multidrug resistant cell line which displays resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. One example of such a cell line is H69AR. Other suitable cell lines can be produced by stepwise selection of a non-resistant cell line in the presence of increasing concentrations of a drug for which resistance is to be acquired over a period of several months to years. For example, a cell line is cultured in the presence of an anthracycline, preferably doxorubicin, for about 14 months. Multidrug resistance is then assessed by exposing the selected cell line to other drugs, e.g. an epipodophyllotoxin such as VP-16 and a Vinca alkaloid such as vincristine, and determining the cytotoxicity of the drug for the cell line. The ability of chemosensitizers which reverse P-glycoprotein-mediated multidrug resistance, such as verapamil and cyclosporin A, to reverse the multidrug resistance is then assessed by exposing the selected cell line to these agents in the presence of the resistant drugs. A detailed description of the procedures which can be used to produce appropriate multidrug resistant cell line such as H69AR is found in Cole, *Cancer Chemother Pharmacol.* 17, 259–263 (1986), Mirski et al., *Cancer Research* 47, 2594–2598 (1987) and Cole, et al. *British J. Cancer* 59:42–46 (1989).

An appropriate multidrug resistant cell line (e.g. a multidrug resistant cell line which displays resistance to anthracyclines, epipodophyllotoxins and Vinca alkaloids that is not substantially reversed by verapamil or cyclosporin A) is used to isolate a nucleic acid of the invention by preparing a cDNA library from this cell line by standard techniques and screening this library with cDNA produced from total mRNA isolated from the multidrug resistant cell line and its drug sensitive parental cell line. For example, a cDNA library constructed from total mRNA from H69AR cells is prepared. The library is plated and two sets of replica filters are prepared by standard methods. One set of filters is then screened with cDNA prepared from H69AR mRNA and the other set of filters is screened with a comparable amount of cDNA prepared from H69 mRNA. The cDNA used for screening the library is labelled, typically with a radioactive label. Following visualization of the hybridization results by standard procedures, cDNA clones displaying increased hybridization with H69AR cDNA when compared to H69 cDNA can be selected from the library. These cDNAs are derived from mRNAs overexpressed in H69AR cells when compared with H69 cells. For descriptions of differential cDNA library screening see King, C. R., et al. *J Biol. Chem.* 254, 6781 (1979); Van der Bliek, A. M., et al., *Mol. Cell Biol.* 6, 1671 (1986).

Determination of whether a cDNA so isolated has the biological activity of MRP can be accomplished by expressing the cDNA in a nonresistant mammalian cell, by standard techniques, and assessing whether expression in the cell of the protein encoded by the cDNA confers on the cell multidrug resistance to anthracyclines, epipodophyllotoxins and Vinca alkaloids that is not substantially reversed by verapamil or cyclosporin A. A cDNA having the biological activity of MRP so isolated can be sequenced by standard techniques, such as dideoxynucleotide chain termination or Maxam-Gilbert chemical sequencing, to determine the nucleic acid sequence and the predicted amino acid sequence of the encoded protein.

An isolated nucleic acid of the invention which is DNA can also be isolated by preparing a labelled nucleic acid probe encompassing all or part of the nucleotide sequence shown in SEQ ID NO: 1 and using this labelled nucleic acid probe to screen an appropriate DNA library (e.g. a cDNA or genomic DNA library). For instance, a cDNA library made from a multi-drug resistant cell line as described above can be used to isolate a cDNA encoding a protein having MRP activity by screening the library with the labelled probe using standard techniques. Preferably, an H69AR cDNA library is used. Alternatively, a genomic DNA library can be similarly screened to isolate a genomic clone encompassing a gene encoding a protein having MRP activity. As demonstrated in Example 4, a human MRP gene has been mapped to chromosome 16. Therefore, a chromosome 16 library rather than a total genomic DNA library can also be used to isolate a human MRP gene. Nucleic acids isolated by screening of a cDNA or genomic DNA library can be sequenced by standard techniques.

An isolated nucleic acid of the invention which is DNA can also be isolated by selectively amplifying a nucleic acid encoding a protein having MRP activity using the polymerase chain reaction (PCR) method and genomic DNA or mRNA. To prepare cDNA from mRNA, total cellular mRNA can be isolated, for instance from a multidrug resistant cell line, by a variety of techniques, e.g., by using the guanidiniumthiocyanate extraction procedure of Chirgwin et al., *Biochemistry*, 18, 5294–5299 (1979). cDNA is then synthesized from the mRNA using reverse transcriptase. Moloney MLV reverse transcriptase available from Gibco/BRL, Bethesda, Md., or AMV reverse transcriptase available from Seikagaku America, Inc., St. Petersburg, Fla., are preferably employed. It is possible to design synthetic oligonucleotide primers from the nucleotide sequence shown in SEQ ID NO:1 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis.

A isolated nucleic acid of the invention which is RNA can be isolated by cloning a cDNA of the invention into an appropriate vector which allows for transcription of the cDNA to produce an RNA molecule which encodes a protein having MRP activity. For example, a cDNA can be cloned downstream of a bacteriophage promoter, e.g. a T7 promoter, in a vector and the cDNA can be transcribed in vitro with T7 polymerase. A resultant RNA can be isolated by standard techniques.

A nucleic acid of the invention, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Analysis of the nucleotide sequence of SEQ ID NO: 1 using currently available computer software designed for the purpose, such as PC/Gene—IntelliGenetics Inc., Calif., permits the identification of the initiation codon and untranslated sequences of an MRP cDNA. The cDNA coding strand, depicted as SEQ ID NO: 1, contains a 4593 nucleotide open reading frame encoding 1531 amino acids, as well as 195 5' untranslated nucleotides and 223 3' untranslated nucleotides. The intron-exon structure and the transcription regulatory sequences of the gene encoding the MRP cDNA can be identified by using a nucleic acid of the invention to probe a genomic DNA clone library. Regulatory elements, such as promoter and enhancers necessary for expression of the gene encoding the MRP in various tissues, can be identified using conventional techniques. The function of the elements can be confirmed by using them to express a reporter gene such as the bacterial gene lacZ which is operatively linked to the fragments. Such a construct can be introduced into cultured cells using standard procedures or into non-human transgenic animal models. In addition to identifying regulatory elements in DNA, such constructs can also be used to identify nuclear proteins interacting with said elements, using techniques known in the art.

A number of unique restriction sites for restriction enzymes are present in the nucleic acid comprising the nucleotide sequence shown in SEQ ID NO:1 These restriction sites provide access to nucleotide fragments which code for polypeptides unique to the protein encoded by SEQ ID NO:1 (i.e. a protein of the invention).

The isolated nucleic acids of the invention or oligonucleotide fragments of the isolated nucleic acids, allow those skilled in the art to construct nucleotide probes for use in the detection of nucleotide sequences in biological materials, such as tumor cell samples. A nucleotide probe can be labelled with a radioactive element which provides for an adequate signal as a means for detection and has sufficient half-life to be useful for detection, such as $^{32}P$, $^{3}H$, $^{14}C$ or the like. Other materials which can be used to label the probe include antigens that are recognized by a specific labelled antibody, fluorescent compounds, enzymes, antibodies specific for a labelled antigen, and chemiluminescent compounds. An appropriate label can be selected having regard to the rate of hybridization and binding of the probe to the nucleotide to be detected and the amount of nucleotide available for hybridization.

II. Antisense Nucleic Acids

The invention also relates to an antisense nucleic acid, or oligonucleotide fragment thereof, of a nucleic acid of the invention. An antisense nucleic acid can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence found in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO: 1. A nucleic acid is designed which has a sequence complementary to a sequence of the coding or untranslated region of the shown nucleic acid. Alternatively, an antisense nucleic acid can be designed based upon sequences of an MRP gene, identified by screening a genomic library as described above. For example, the sequence of an important regulatory element can be determined as described above and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

III. Recombinant Expression Vectors

The nucleic acids of the present invention which encode proteins having MRP activity can be incorporated in a known manner into a recombinant expression vector which ensures good expression of the encoded protein or part thereof. The recombinant expression vectors are "suitable for transformation of a host cell", which means that the recombinant expression vectors contain a nucleic acid or an oligonucleotide fragment thereof of the invention and a regulatory sequence, selected on the basis of the host cells to be used for expression, which is operatively linked to the nucleic acid or oligonucleotide fragment. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, *Gene Expression Technology: Methods in Enzymology* 185, Academic Press, San Diego, Calif. (1990) can be used. It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids as described herein.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, Calif. (1990).

Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector (e.g. a nucleic acid encoding an MRP protein) so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

Examples of vectors for expression in yeast *S. cerivisae* include pYepSec1 (Baldari, et al., (1987) *Embo J* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Expression of an MRP protein in mammalian cells is accomplished using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral material. For example, commonly used promoters are derived from polyoma, Adenovirus 2, cytomegalovirus and most frequently, Simian Virus 40. Preferably, the pRc/CMV expression vector (Invitrogen) is used. In the pRc/CMV vector, nucleic acid introduced into the vector to be expressed is under the control of the enhancer/promoter sequence from the immediate early gene of human cytomegalovirus. Additionally, a gene conferring neomycin resistance is encoded by the vector. In one embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein. For example, a nucleic acid encoding a protein with MRP activity can be preferentially expressed in cardiac muscle cells using promoter and enhancer sequences from a gene which is expressed preferentially in cardiac muscle cells, such as a cardiac myosin gene or a cardiac actin gene.

The recombinant expression vector of the invention can be a plasmid. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The invention further provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to the nucleotide sequence of SEQ ID NO: 1. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA, as described above.

IV. Transformant Host Cells

The recombinant expression vectors of the invention can be used to make a transformant host cell including the recombinant expression vector. The term "transformant host cell" is intended to include prokaryotic and eukaryotic cell which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride coprecipitation, DEAE-dextran-mediated transfection, lipofectin, electroporation or microinjection. Suitable methods for transforming and transfecting host cells can be found in Sambrook et al. (*Molecular Cloning: A Laboratory Manual*, 2nd Edition, Cold Spring Harbor Laboratory press (1989)), and other laboratory textbooks.

The number of host cells transformed with a recombinant expression vector of the invention by techniques such as those described above will depend upon the type of recombinant expression vector used and the type of transformation technique used. Plasmid vectors introduced into mammalian cells are integrated into host cell DNA at only a low frequency. In order to identify these integrants, a gene that contains a selectable marker (i.e., resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, preferably, are introduced on a the same plasmid. Host cells transformed with a one or more recombinant expression vectors containing a nucleic acid of the invention and a gene for a selectable marker can be identified by selecting for cells using the selectable marker. For example, if the selectable marker encoded a gene conferring neomycin resistance (such as pRc/CMV), transformant cells can be selected with G418. Cells that have incorporated the selectable marker gene will survive, while the other cells die.

As demonstrated in Examples 5 and 6, the nucleic acids o f t he invention can confer multidrug resistance to drugs including anthracyclines, epipodophyllotoxins and Vinca alkaloids on a drug sensitive cell when transfected into the cell. Thus, these drugs can be used as selecting agents when preparing a transformant host cell rather than using an independent selectable marker (such as neomycin resistance). Therefore, the nucleic acids of the invention are useful not only for conferring multidrug resistance on a cell but also as selectable markers for cells into which the nucleic acid has been introduced. See for example Pastan et al. U.S. Pat. No. 5,166,059; Croop et al. U.S. Pat. No. 5,198,344. Cells are selected by exposure to one or more drugs for which resistance is conferred by the nucleic acid. An MRP-encoding nucleic acid in a recombinant expression vector can be introduced into a cell together with a second nucleic acid comprising a gene of interest, either in the same vector or in separate vectors, and transformant cells can be selected based upon their acquired drug resistance. Drug resistant cells which are selected will contain the MRP-encoding nucleic acid often cointegrated with the gene of interest. Furthermore, by increasing stepwise the concentration of drug used in selecting the cells, it is possible to obtain transformant cells with a higher number of copies of the introduced nucleic acid, including both the MRP-encoding nucleic acid and a gene of interest. Therefore, the nucleic acids of the invention are also useful as amplifiable markers.

The nucleic acids of the invention encode proteins "having biological activity of MRP". The biological activity of MRP is defined as the ability of the protein, when expressed in a drug sensitive mammalian cell, to confer on the cell multidrug resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. An isolated nucleic acid of the invention can be tested for MRP activity by incorporating the nucleic acid into a recombinant expression vector of the invention, transforming a drug sensitive mammalian cell with the recombinant expression vector to make a transformant host cell of the invention as described above and testing the multidrug resistance of the transformant host cell. The multidrug resistance of the transformant host cell is tested by determining the cytotoxicity of the drugs to be tested (i.e. anthracyclines, epipodophyllotoxins and Vinca alkaloids) for the transformed cell as compared to the untransformed cell, and the ability of other drugs (i.e. verapamil and cyclosporin A) to reverse multidrug resistance. For example, in a preferred embodiment, the transformant host cell is a HeLa cell, and the multidrug resistance of transfected HeLa cells is compared to that of untransfected HeLa cells or preferably to HeLa cells transfected with the parental expression vector lacking the nucleic acid encoding a protein having MRP activity.

V. Isolated Proteins

The invention provides isolated proteins having biological activity of MRP. The term "isolated" refers to a protein substantially free of cellular material or culture medium when produced by recombinant DNA techniques, or chemical precursors or other chemicals when chemically synthesized. In a preferred embodiment the protein having biological activity of MRP comprises an amino acid sequence shown in SEQ ID NO: 2. Alternatively, the protein can be encoded by a nucleic acid comprising the nucleotide sequence of SEQ ID NO: 1. Proteins having biological activity of MRP which have substantial sequence homology to the amino acid sequence of SEQ ID NO: 2, as defined above, are also encompassed by the invention. Furthermore, proteins having biological activity of MRP that are encoded by nucleic acids which hybridize under high or low stringency conditions, as defined above, to a nucleic acid comprising a nucleotide sequence shown in SEQ ID NO: 1 are encompassed by the invention. Additionally, immunogenic portions of MRP proteins are within the scope of the invention. As demonstrated in Example 7, two immunogenic portions of a protein comprising an amino acid sequence shown in SEQ ID NO: 2 correspond to amino acid residues 932–943 shown in SEQ ID NO: 2 (residues AELQKAEAKKEE) and amino acid residues 1427–1441 (residues GENLSVGQRQLVCLA). Two other immunogenic portions correspond to amino acid residues 243–252 shown in SEQ ID NO: 2 (residues SLNKEDTSEQ) and amino acid residues 765–779 (residues GVNLSGGQKQRVSLA). Preferred immunogenic portions correspond to regions of the protein not conserved in other ABC superfamily members, i.e. outside of the two NBF domains (amino acid residues 661–810 and 1310–1469), and include regions between the 12 membrane spanning regions. An immunogenic portion will be of at least about eight amino acids in length. See Almquist et al. *Cancer Research* 55:102–110 (1995).

The MRP protein, or isoforms or parts thereof, of the invention can be isolated by expression in a suitable host cell using techniques known in the art. Suitable host cells include prokaryotic or eukaryotic organisms or cell lines, for example, yeast, *E. coli* and insect cells. The recombinant expression vectors of the invention, described above, can be used to express a protein having MRP activity in a host cell in order to isolate the protein. The invention provides a method of preparing an isolated protein of the invention comprising introducing into a host cell a recombinant nucleic acid encoding the protein, allowing the protein to be expressed in the host cell and isolating the protein. Preferably, the recombinant nucleic acid is a recombinant expression vector. Proteins can be isolated from a host cell expressing the protein according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22, 233–577 (1971)).

Alternatively, the protein or parts thereof can be prepared by chemical synthesis using techniques well known in the chemistry of proteins such as solid phase synthesis (Merrifield, 1964, J. Am. Chem. Assoc. 85:2149–2154) or synthesis in homogeneous solution (Houbenweyl, 1987, Methods of Organic Chemistry, ed. E. Wansch, Vol. 15 I and II, Thieme, Stuttgart).

VI. Antibodies

The proteins of the invention, or portions thereof, can be used to prepare antibodies specific for the proteins. Antibodies can be prepared which bind a distinct epitope in an unconserved region of the protein. An unconserved region of the protein is one which does not have substantial sequence homology to other proteins, for example other members of the ABC superfamily of membrane transport proteins. For example, unconserved regions encompassing sequences between the twelve membrane spanning regions, excluding the NBF domains, can be used. Alternatively, a region from one of the two NBF domains can be used to prepare an antibody to a conserved region of an MRP protein. An antibody to a conserved region may be capable of reacting with other members of the ABC family of membrane transport proteins. Conventional methods can be used to prepare the antibodies. For example, by using a peptide of an MRP protein, polyclonal antisera and monoclonal antibodies can be made using standard methods. As demonstrated in Example 7, a mammal, (e.g., a mouse, hamster, or rabbit) can be immunized with an immunogenic form of the peptide which elicits an antibody response in the mammal. Alternatively, polyclonal antisera and monoclonal antibodies can made by immunizing an animal with a cell which expresses MRP or by immunizing with a membrane fraction of an MRP expressing cell. As demonstrated in Example 8, a mammal (e.g., a mouse, hamster, or rabbit) can be immunized with enriched membrane fractions of the H69AR cell line to elicit a polyclonal antibody response against antigens expressed by the membrane fractions, including MRP. Monoclonal antibodies can then be made by conventional techniques and a monoclonal antibody specific for an MRP protein can be selected, as described further in Example 8.

Two hybridomas, designated QCRL-1 and QCRL-3, producing monoclonal antibodies QCRL-1 and QCRL-3 described in further detail in Example 8, have been deposited with the American Type Culture Collection on Nov. 30, 1994, under the provisions of the Budapest Treaty and have been assigned accession numbers HB 11765 and HB 11766, respectively.

To generate suitable anti-MRP antibodies, the immunogen should contain an effective, immunogenic amount of an MRP peptide or protein, e.g., as a membrane-bound protein, isolated protein, recombinantly produced protein, synthetic peptide, or other suitable form of the immunogen. The immunogen can optionally be used as a conjugate linked to a carrier. The effective amount of immunogen per unit dose depends, among other things, on the species of animal inoculated, the body weight of the animal and the chosen immunization regimen, as is well known in the art. An immunization preparation can also include an adjuvant as part of the diluent. Adjuvants such as complete Freund's adjuvant (CFA), incomplete Freund's adjuvant (IFA) and alum are materials well known in the art, and are available commercially from several sources. Techniques for conferring immunogenicity on a peptide include conjugation to a carrier. The progress of immunization can be monitored by detection of antibody titers in plasma or serum. Standard ELISA or other immunoassay can be used with the immunogen as antigen to assess the level of antibody titers. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* 256, 495–497 (1975)) as well as other techniques such as the human B-cell hybridoma technique (Kozbor et al., *Immunol. Today* 4, 72 (1983)), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* 246, 1275 (1989)). Hybridoma cells can be screened immunochemically for production of antibodies specifically reactive with an MRP protein or peptide and monoclonal antibodies isolated by standard techniques (see Example 8).

The term antibody as used herein is intended to include fragments thereof which are also specifically reactive with a protein, or peptide thereof, having the biological activity of MRP. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing an immunoglobulin variable region which recognizes an MRP protein of the invention. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a protein, or peptide thereof, having the biological activity of a MRP as described herein can be further humanized by producing human variable region chimeras, in which parts of the variable regions, especially the conserved framework regions of the antigen-binding domain, are of human origin and only the hypervariable regions are of non-human origin. Such altered immunoglobulin molecules, referred to herein as "humanized" antibodies, may be made by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al., *Meth. Enzymol*, 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

Another method of generating specific antibodies, or antibody fragments, reactive against protein, or peptide thereof, having the biological activity of a MRP is to screen expression libraries encoding immunoglobulin genes, or portions thereof, expressed in bacteria with peptides produced from the nucleic acid molecules of the present invention. For example, complete Fab fragments, $V_H$ regions, $V_L$ regions, and $F_V$ regions can be expressed in bacteria using phage expression libraries. See for example Ward et al., *Nature* 341, 544–546; (1989); Huse et al., *Science* 246, 1275–1281 (1989); and McCafferty et al. *Nature* 348, 552–554 (1990). To identify an anti-MRP antibody, or antibody fragment, such libraries can be screened with an MRP protein of the invention, or peptide thereof. Alternatively, the SCID-hu mouse available from Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of an MRP protein of the invention, portions thereof or closely related isoforms in a sample in order to diagnose multidrug resistance, and to determine the role of MRP proteins in particular cellular events or pathological states, particularly its role in multidrug resistance. Using methods described hereinbefore, polyclonal, monoclonal antibodies, or chimeric monoclonal antibodies can be raised to nonconserved regions of MRP and used to distinguish MRP from closely related isoforms and other proteins that share a common conserved epitope.

The polyclonal or monoclonal antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

The present invention allows the skilled artisan to prepare bispecific antibodies and tetrameric antibody complexes. Bispecific antibodies can be prepared by forming hybrid hybridomas. The hybrid hybridomas can be prepared using the procedures known in the art such as those disclosed in Staerz & Bevan, (PNAS (USA) 83:1453, 1986 and Immunology Today, 7:241, 1986). In general, a hybrid hybridoma is formed by fusing a first cell line which produces a first monoclonal antibody which is capable of binding to a tumor cell expressing a protein of the invention and a second cell line which produces a second monoclonal antibody which is capable of binding to a detectable substance, or a substance having toxic or therapeutic activity. The bispecific antibodies can also be constructed by chemical means using procedures such as those described by Staerz et al., (Nature, 314:628, 1985) and Perez et al., (Nature 316:354, 1985).

Bispecific monoclonal antibodies containing a variable region of an antibody, preferably a human antibody, specific for an MRP protein of the invention or portion thereof, a variable region of an antibody which is capable of binding to a detectable substance, or a substance having toxic or therapeutic activity and the constant regions of human immunoglobulins such as human IgG1, IgG2, IgG3 and IgG4 can also be constructed as described above. Bispecific chimeric monoclonal antibodies can also be constructed as described above.

A tetrameric antibody complex can be prepared by preparing a first monoclonal antibody which is capable of binding to a tumor cell expressing a protein of the invention and a second monoclonal antibody which is capable of binding to a detectable substance or a substance having toxic or therapeutic activity. The first and second antibody are from a first animal species. The first and second antibody are reacted with an about equimolar amount of antibodies of a second animal species or Fab fragments thereof, which are directed against the Fc-fragments of the antibodies of the first animal species. The tetrameric complex formed is then isolated. (See U.S. Patent No. 4,868,109 to Lansdorp for a description of methods for preparing tetrameric antibody complexes).

Examples of detectable substances are enzymes, such as horseradish peroxidase, alkaline phosphatase, glucose oxidase and galactosidase. Examples of substances having toxic activity are cytotoxic cells such as macrophages, neutrophils, eosinophils, NK cells, LAK cells, and large granular lymphocytes or substances which are toxic to tumor cells such as radionuclides, and toxins such as diptheria toxin and ricin or attenuated derivatives thereof. It will be appreciated that the antibody can be directed against the Fc receptor on cytotoxic cells. Examples of substances having therapeutic activity are chemotherapeutic agents such as carboplatin and methotrexate. Preferably, the chemotherapeutic agent is not a drug to which a protein having MRP activity confers resistance.

The antibodies, bispecific antibodies and tetrameric antibody complexes of the invention directed against a protein having MRP activity, optionally coupled with a substance having toxic or therapeutic activity, can be used to treat multidrug resistant tumors. Accordingly, the invention provides a composition comprising antibodies, bispecific antibodies or tetrameric antibody complexes in a pharmaceutically acceptable carrier. Preferably, the antibodies, bispecific antibodies or tetrameric antibody complexes are coupled to or capable of binding to a substance having toxic or therapeutic activity and to a tumor cell expressing a protein of the invention.

The compositions of the invention are administered to subjects in a biologically compatible form suitable for pharmaceutical administration in vivo. By "biologically compatible form suitable for administration in vivo" is meant a form of the antibody to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of an antibody reactive with an MRP protein of the invention may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

An antibody composition can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer an antibody reactive with an MRP protein by other than parenteral administration, it may be necessary to coat the antibody with, or co-administer the antibody with, a material to prevent its inactivation. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., antibody reactive against an MRP protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

VII. Transgenic and Knockout Animals

Nucleic acids which encode proteins having biological activity of MRP can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a human MRP cDNA, comprising the nucleotide sequence shown in SEQ ID NO: 1, or an appropriate sequence thereof, can be used to clone a murine MRP gene in accordance with established techniques and the genomic nucleic acid used to generate transgenic animals that contain cells which express MRP protein. Methods for generating transgenic animals, particularly animals such as mice, have become conventional in the art and are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. [Hogan, B. et al., (1986) A Laboratory Manual, Cold Spring Harbor, N.Y., Cold Spring Harbor Laboratory].

Alternatively, an embryonal stem cell line can be transfected with an expression vector containing nucleic acid encoding a protein having MRP activity and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harbouring the transfected DNA in their germ cells can be used to breed uniformly transgenic mice.

Typically, particular cells would be targeted for MRP transgene incorporation by use of tissue specific enhancers operatively linked to the MRP-encoding gene. For example, promoters and/or enhancers which direct expression of a gene to which they are operatively linked preferentially in cardiac muscle cells can be used to create a transgenic animal which expresses an MRP protein preferentially in cardiac muscle tissue. Examples of suitable promoters and enhancers include those which regulate the expression of the genes for cardiac myosin and cardiac actin. Transgenic animals that include a copy of an MRP transgene introduced into the germ line of the animal at an embryonic stage can also be used to examine the effect of increased MRP expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., 1989, Molecular Cloning, A Laboratory Manual, Cold Spring Harbor Laboratory Press. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include lacZ (B-galactosidase), neo (neomycin phosphotransferase), CAT (chloramphenicol acetyltransferase) dhfr (dihydrofolate reductase), aphIV (hygromycin phosphotransferase), lux (luciferase), uidA (B-glucuronidase). Preferably, the reporter gene is lacZ which codes for B-galactosidase. B-galactosidase can be assayed using the lactose analogue X-gal(5-bromo-4-chloro-3-indolyl-b-D-galactopyranoside) which is broken down by B-galactosidase to a product that is blue in color. (See for example Old R. W. & Primrose S. B., Principles of Gene Manipulation. An Introduction to Genetic Engineering, 4th ed. Oxford University Press at pages 63–66 for a discussion of procedures for screening for recombinants).

Although experimental animals used in the preferred embodiment disclosed are mice, the invention should not be limited thereto. It can be desirable to use other species such as rats, hamsters and rabbits.

The transgenic animals of the invention can be used to investigate the molecular basis of multidrug resistance. The transgenic animals of the invention can also be used to test substances for the ability to prevent, slow or reverse the development of multidrug resistance. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or reverse multidrug resistance.

Additionally, the non-human homologues of genes encoding proteins having MRP activity can be used to construct an MRP "knock out" animal which has a defective or altered MRP gene. For example, a human MRP cDNA, comprising the nucleotide sequence shown in SEQ ID NO: 1, or an appropriate sequence thereof, can be used to clone a murine MRP gene in accordance with established techniques. A portion of the isolated genomic MRP DNA (e.g., an exon) can be deleted or replaced with another gene, such as a gene encoding a selectable marker which can be used to monitor integration. The altered MRP DNA can then be transfected into an embryonal stem cell line. The altered MRP DNA will homologously recombine with the endogenous MRP gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered MRP gene in every cell. Accordingly, a knockout animal can be made which cannot express a functional MRP protein. Such a knockout animal can be used, for example, to test the effectiveness of a chemotherapeutic agent in the absence of an MRP multidrug resistance protein.

VIII. Uses of the Invention

The isolated nucleic acids of the invention are useful as molecular probes for use diagnostically to determine multidrug resistance of a tumor. As demonstrated in Example 1, multidrug resistance of certain tumor cell lines is associated with increased expression of cellular mRNA corresponding to the nucleotide sequence of SEQ ID NO: 1. Accordingly, the nucleic acids of the invention can be labelled with a detectable marker, such as a radioactive, fluorescent or biotinylated marker, and used in conventional dot blot, Northern hybridization or in situ hybridization procedures to probe mRNA molecules of total cellular or poly(A)+ RNAs from a biological sample, for instance cells of a tumor biopsy.

The nucleic acid probes can be used to detect genes, preferably in human cells, that encode proteins related to or analogous to the MRP of the invention. Preferably, nucleic acid comprising the nucleotide sequence of the invention, or a segment thereof, can be used as a probe to identify DNA fragments comprising genes or parts of genes that are co-amplified with the gene of the invention and which reside within the same amplification unit, or amplicon, at the chromosomal location 16p13.1. More specifically a nucleic acid of the invention can be used as a probe to screen human genomic DNA libraries constructed in cosmid or yeast artificial chromosome vectors, using procedures standard in the art, to define a contiguous segment of DNA that comprises the amplification unit detected in a multidrug resistant cell line such as H69AR. In this manner additional genes can be identified which also confer or contribute to the multidrug resistance phenotype of H69AR and other human cell lines yet to be examined but which are known to include the HeLa cell line J2c and HT1080 DR4 cell line.

The antisense nucleic acids of the invention are useful for inhibiting expression of nucleic acids (e.g. mRNAs) encoding proteins having MRP activity, thereby decreasing expression of proteins having MRP activity Since increased expression of proteins having MRP activity is associated with and can confer multidrug resistance on a cell, decreasing expression of such proteins can inhibit or reverse multidrug resistance of a cell into which the antisense nucleic acid has been introduced. Antisense nucleic acids can be introduced into a multidrug resistant cell in culture to inhibit MRP expression. One or more antisense nucleic acids, such as oligonucleotides, can be added to cells in culture media, typically at 200 µg/ml. A cultured multidrug resistant cell in which MRP expression is inhibited is useful for testing the efficacy of potential therapeutic agents. For example, MRP expression could be inhibited in a tumor cell line which expresses both MRP and P-glycoprotein to determine the contribution of MRP to an observed resistance or sensitivity of the cell to a particular therapeutic agent.

The antisense nucleic acids of the invention, or oligonucleotides thereof, can also be used in gene therapy to correct or prevent multidrug resistance in a subject. For example, antisense sequences can be used to render multidrug resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotides thereof, can be directly introduced into tissues, including lung tissue in vivo, using delivery vehicles such as liposomes, retroviral vectors, adenoviral vectors and DNA virus vectors. A delivery vehicle can be chosen which can be targeted to a cell of interest in the subject (e.g. a multidrug resistant tumor cell). Antisense nucleic acids can also be introduced into isolated cells, such as those of the hematopoietic system, ex vivo using viral vectors or physical techniques such as microinjection and electroporation or chemical methods such as coprecipitation and incorporation of DNA into liposomes and such cells can be returned to the donor. Recombinant molecules can also be delivered in the form of an aerosol or by lavage. In the treatment of lung malignancies, antisense sequences can be directly delivered to lung tissue by an aerosol or by lavage.

Accordingly, the invention provides a method for inhibiting multidrug resistance of a multidrug resistant cell by introducing into the multidrug resistant cell a nucleic acid which is antisense to a nucleic acid which encodes the protein shown in SEQ ID NO: 2.

The nucleic acids of the invention can further be used to design ribozymes which are capable of cleaving a single-stranded nucleic acid encoding a protein having MRP activity, such as an mRNA. A catalytic RNA (ribozyme) having ribonuclease activity can be designed which has specificity for an MRP-encoding mRNA based upon the sequence of a nucleic acid of the invention. For example, a derivative of a Tetrahymena L-19 IVS RNA can be constructed in which the base sequence of the active site is complementary to the base sequence to be cleaved in an MRP-encoding mRNA. See for example Cech et al. U.S. Pat. No. 4,987,071; Cech et al. U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. *Science* 261, 1411–1418 (1993).

The isolated nucleic acids and antisense nucleic acids of the invention can be used to construct recombinant expression vectors as described previously. These recombinant expression vectors are then useful for making transformant host cells containing the recombinant expression vectors, for expressing proteins encoded by the nucleic acids of the invention, and for isolating proteins of the invention as described previously. The isolated nucleic acids and antisense nucleic acids of the invention can also be used to construct transgenic and knockout animals as described previously.

As demonstrated in Examples 5 and 6, a recombinant expression vector containing a nucleic acid of the invention can be used to transfect a drug sensitive cell line to produce a protein in the cell which can confer multidrug resistance on the transfected cell line. Thus, the recombinant expression vectors of the invention are useful for conferring multidrug resistance on a drug sensitive cell. Accordingly, the invention provides a method for protecting a drug sensitive cell from cytotoxicity due to exposure to a drug by transfecting the cell with nucleic acid comprising a nucleotide sequence shown in SEQ ID NO: 1 to confer drug resistance on the cell. In preferred embodiments, the drug sensitive cell is a cardiac muscle cell or a hematopoietic stem cell. The ability to confer drug resistance on a cell has important clinical applications. A major dose-limiting factor for chemotherapeutic agents is their cytotoxicity for normal cells in a patient as well as tumor cells. In patients with multi-drug resistant tumors, increasing the dosage of chemotherapeutic agents is prohibited by the toxicity of these agents for normal cells. In the case of anthracyclines, cardiotoxicity of the drugs can be a major clinical limitation. For chemotherapeutic drugs which target rapidly dividing cells, toxicity to hematopoietic cells can be a major clinical limitation. Additionally, neurotoxicity can occur. Protecting nonresistant nontumor cells from the effects of chemotherapeutic agents, by conferring on the cell multidrug resistance, thus has major clinical importance.

The transformant host cells of the invention, and recombinant expression vectors used to make them, are useful for testing potential therapeutic agents for their effectiveness against multidrug resistant cells. These agents include agents which are themselves cytotoxic for multidrug resistant cells or which are chemosensitizers of other therapeutic agents. As used herein, the term "chemosensitizer" refers to a substance which can increase the efficacy of a therapeutic agent against a multidrug resistant cell and/or decrease the resistance of a multidrug resistant cell for a therapeutic agent.

A method is provided for identifying a chemosensitizer of a therapeutic agent. The method involves incubating the therapeutic agent with a cell transfected with a nucleic acid which confers resistance to the therapeutic agent on the cell, both with and without a substance to be tested, determining resistance of the cell to the therapeutic agent when incubated with and without the substance to be tested and identifying a substance which is a chemosensitizer of the therapeutic agent by the ability of the substance to decrease the resistance of the cell to the therapeutic agent when incubated with the substance as compared to the resistance of the cell to the therapeutic agent when incubated without the substance. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential chemosensitizing substances can be a cell in culture, e.g. a transformant host cell of the invention, and the therapeutic agent and substance to be tested are incubated in culture with the cell. Alternatively, the cell can be a multidrug resistant cell in a transgenic animal, transgenic for a nucleic acid of the invention, and the therapeutic agent and substance to be tested are administered to the transgenic animal. Furthermore, the cell can be a cell in culture isolated from a multidrug resistant transgenic animal of the invention. The resistance of the cell for the therapeutic agent in the presence and absence of the potential therapeutic agent is assessed by determining the concentration of the therapeutic agent which is cytotoxic for the cell either in the presence or in the absence of the substance being tested.

The invention provides a method for identifying a substance which is directly cytotoxic to a multidrug resistant cell involving incubating a substance to be tested with a cell transfected with a nucleic acid which confers multidrug resistance on the cell and determining the cytotoxicity of the substance for the cell. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential cytotoxic substances can be a cell in culture, e.g. a transformant host cell of the invention, and the substance to be tested is incubated in culture with the cell. Alternatively, the cell can be a multidrug resistant cell in a transgenic animal, transgenic for a nucleic acid of the invention and the substance to be tested is administered to the transgenic animal. Furthermore, the cell can be a cell in culture isolated from a multidrug resistant transgenic animal of the invention.

Additionally, a multidrug resistant cell line such as H69AR, or an equivalent cell line, can be used in the same methods for identifying a chemosensitizer of a therapeutic agent or for identifying a substance which is directly cytotoxic to a multidrug resistant cell.

The isolated proteins of the invention are useful for making antibodies reactive against proteins having MRP activity, as described previously. Alternatively, the antibodies of the invention can be used to isolate a protein of the invention by standard immunoaffinity techniques. Furthermore, the antibodies of the invention, including bispecific antibodies and tetrameric antibody complexes, are useful for diagnostic purposes and for therapeutic purposes.

In one embodiment of the invention, antibodies labelled with a detectable substance, such as a fluorescent marker, an enzyme or a radioactive marker, can be used to identify multidrug resistant tumor cells in a tumor sample or in vivo. Tumor tissue removed from a patient can be used as the tumor sample. In order to prevent tumor samples from being degraded, the samples can be stored at temperatures below −20° C. A tissue section, for example, a freeze-dried or fresh frozen section of tumor tissue removed from a patient, can also be used as the tumor sample. The samples can be fixed and the appropriate method of fixation is chosen depending upon the type of labelling used for the antibodies. Alternatively, a cell membrane fraction can be separated from the tumor tissue removed from a patient and can be used as the tumor sample. Conventional methods such as differential or density gradient centrifugation can be used to separate out a membrane fraction.

A multidrug resistant tumor cell is identified by incubating an antibody of the invention, for example a monoclonal antibody, with a tumor cell to be tested for multidrug resistance. Binding of the antibody to the tumor cell is indicative of the presence on the tumor cell of a protein having MRP activity. The level of antibody binding to the tumor cell can be compared to the level of antibody binding to a normal control cell, and increased binding of the antibody to the tumor cell as compared to the normal cell can be used as an indicator of multidrug resistance. Binding of the antibody to a cell (e.g. a tumor cell to be tested or a normal control cell) can be determined by detecting a detectable substance with which the antibody is labelled. The detectable substance may be directly coupled to the antibody, or alternatively, the detectable substance may be coupled to another molecule which can bind the antibody. For example, an antibody of the invention which has a rabbit Fc region (e.g. which was prepared by immunization of a rabbit) can be detected using a second antibody directed against the rabbit Fc region, wherein the second antibody is coupled to a detectable substance.

A multidrug resistant tumor cell can be detected as described above in vitro in a tumor sample prepared as described above. For example, a tumor section on a microscope slide can be reacted with antibodies using standard immunohistochemistry techniques. Additionally, if a single cell suspension of tumor cells can be achieved, tumor cells can be reacted with antibody and analyzed by flow cytometry. Alternatively, a multidrug resistant tumor cell can be detected in vivo in a subject bearing a tumor. Labelled antibodies can be introduced into the subject and antibodies bound to the tumor can be detected. For example, the antibody can be labelled with a radioactive marker whose presence and location in a subject can be detected by standard imaging techniques.

The antibodies of the invention, and compositions thereof, can also be used to inhibit the multidrug resistance of a multidrug resistant cell. The invention provides a method for inhibiting the multidrug resistance of a multidrug resistant cell comprising inhibiting activity of a protein comprising an amino acid shown in SEQ ID NO: 2 expressed by the multidrug resistant cell. Preferably, the multidrug resistant cell is a tumor cell. In preferred embodiments, the molecule which binds to a protein comprising an amino acid sequence shown in SEQ ID NO: 2 is a monoclonal antibody, bispecific antibody or tetrameric immunological complex of the invention. Multidrug resistance can be inhibited by interfering with the MRP activity of the protein to which the molecule binds. For example, the ability of an MRP protein to transport drugs may be impaired. Accordingly, any molecule which binds to a protein having MRP activity and whose binding inhibits the MRP activity of the protein are encompassed by invention. Isolated proteins of the invention, comprising the amino acid sequence shown in SEQ ID NO: 2, can be used to identify molecules, including and in addition to the antibodies of the invention, which can bind to a protein having MRP activity in a standard binding assay. A multidrug resistant cell in which multidrug resistance is inhibited, by inhibiting the activity of an MRP protein, can further be treated with a therapeutic agent to which the cell is no longer resistant or less resistant due to inhibition of MRP activity in order to kill the cell.

Molecules which bind to a protein comprising an amino acid sequence shown in SEQ ID NO: 2 can also be used in a method for killing a multidrug resistant cell which expresses the protein. Preferably, the multidrug resistant cell is a tumor cell. Destruction of a multidrug resistant cells can be accomplished by labelling the molecule with a substance having toxic or therapeutic activity. The term "substance having toxic or therapeutic activity" as used herein is intended to include molecules whose action can destroy a cell, such as a radioactive isotope, a toxin (e.g. diptheria toxin or ricin), or a chemotherapeutic drug, as well as cells whose action can destroy a cell, such as a cytotoxic cell. The molecule binding to multidrug resistant cells can be directly coupled to a substance having toxic or therapeutic activity (e.g. a ricin-linked monoclonal antibody), or may be indirectly linked to the substance. For example, a bispecific antibody which is capable of crosslinking a tumor cell and a cytotoxic cell can be used, thereby facilitating lysis of the tumor cell. A bispecific antibody can crosslink a tumor cell and the cytotoxic cell by binding to the Fc receptors of cytotoxic cells.

The compositions and methods of the invention can be used to treat patients with tumors displaying multidrug resistance particularly those displaying resistance to anthracyclines, epipodophyllotoxins, vinca alkaloids, and hydrophobic drugs. The methods of the invention for inhibiting the multidrug resistance of a tumor cell and for killing a multidrug resistant tumor cell can be applied to patients having a multidrug resistant tumor. The compositions and methods can be particularly useful in treating breast cancer, leukemias, fibrosarcomas, cervical cancer, gliomas, thymomas, neuroblastomas and lung cancer, in particular small cell lung cancers and non small cell lung cancers.

The invention also provides a diagnostic kit for identifying multidrug resistant tumor cells comprising a molecule which binds to a protein comprising an amino acid sequence shown in SEQ ID NO: 2 for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. Other molecules which can bind a protein having MRP activity can be used, including the bispecific antibodies and tetrameric antibody complexes of the invention. The diagnostic kit can also contain an instruction manual for use of the kit.

The invention further provides a diagnostic kit for identifying multidrug resistant tumor cells comprising a nucleotide probe complementary to the sequence, or an oligonucleotide fragment thereof, shown in SEQ ID NO: 1 for hybridization with mRNA from a sample of tumor cells; means for detecting the nucleotide probe bound to mRNA; means for determining the amount of mRNA in the sample; and means for comparing the amount of mRNA in the sample with a standard. The diagnostic kit can also contain an instruction manual for use of the kit.

The invention is further illustrated by the following examples. However, the examples are merely intended to illustrate embodiments of the invention and are not to be construed to limit the scope of the invention. The contents of all references and published patents and patent applications cited throughout this application are hereby incorporated by reference.

EXAMPLE 1

ISOLATION OF cDNA SEQUENCES DERIVED FROM mRNAS OVEREXPRESSED IN H69AR CELLS

Figure 1A:
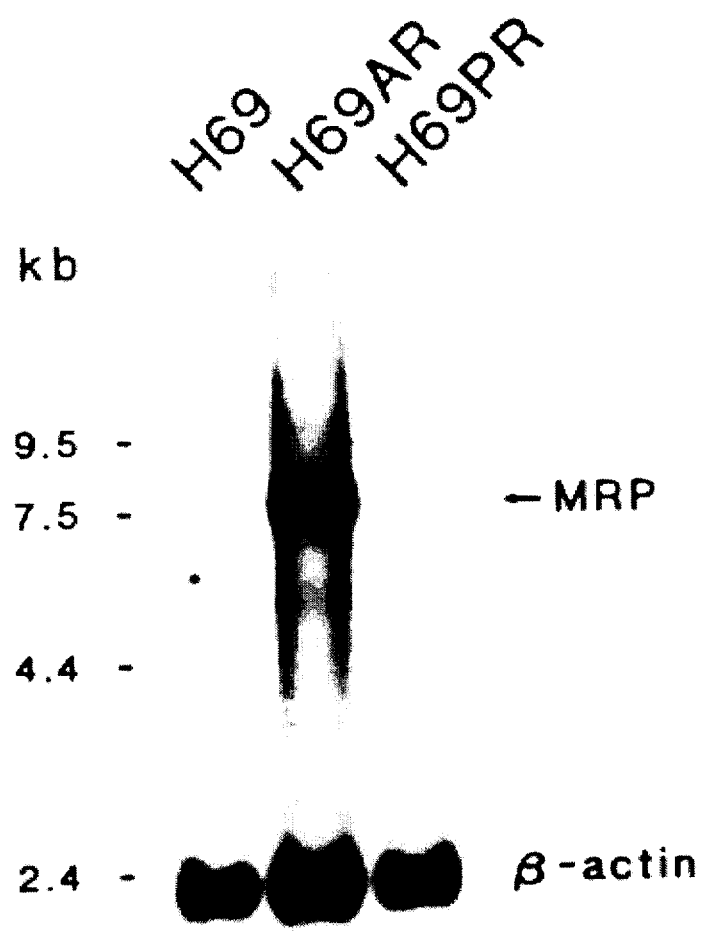
FIG. 1A is a Northern blot of poly(A⁺)RNA from H69, H69AR and H69PR cells hybridized with a 1.8 kb EcoR1 cDNA fragment of the multidrug resistance protein of the invention.

As part of a search of proteins responsible for the multidrug resistance displayed by H69AR cells, a randomly primed cDNA library constructed from H69AR mRNA was screened using differential hybridization with total cDNA prepared from H69 and H69AR mRNA. One of the clones isolated contained a 2.8 kb cDNA insert and gave a particularly strong differential signal when analyzed on northern blots (FIG. 1A). The analysis of 1 μg of poly(A$^+$)RNA from each cell line was carried out using standard procedures. Poly(A$^+$)RNA was obtained using a Fast Track™ mRNA isolation kit (Invitrogen) and 1 μg was electrophoresed on a denaturing formaldehyde agarose gel. The RNA was transferred to nitrocellulose membrane and prehybridized in 50% formamide, 533 SSPE(1×=150 mM NaCl, 10 mM NaH$_2$PO$_4$, 1 mM EDTA, pH 7.4), 2.5×Denhardt's solution (50×=1% bovine serum albumin, 1% polyvinylpyrrolidone, 1% ficoll) and sheared, denatured herring testes DNA (100 μg/ml) for 4–16 hours at 42° C. The blot was probed with a 1.8 kb EcoRI fragment of MRP, labelled to a specific activity of >5×10$^8$ cmp/μg DNA with α-[$^{32}$P]-dCTP (3000 Ci/mmol; Dupont/NEN) by the random priming method [A. P. Feinberg, B. Vogelstein, Analyt. Biochem. 132, 6 (1983)]. Hybridization was carried out for 16–20 hours at 42° C. Blots were washed three times in 0.1% SDS and 0.1×SSC (pH 7.0) for 30 minutes each at 52° C. and then exposed to film. To estimate variation in RNA loading of the gel, the blot was reprobed with a $^{32}$P-labelled β-actin cDNA (201pBv2.2)[H. Ueyama, H. Hamada, N. Battula, T. Kakunaga, Mol. Cell. Biol. 4, 1073 (1984)]. The autoradiograph shown in FIG. 1A is a 5 hour exposure with intensifying screens at −70° C. The size of the overexpressed mRNA in H69AR cells was estimated to be approximately 7 kb. Prolonged exposure of the film revealed low levels of this mRNA in H69 and H69PR cells. The concentration of this mRNA was increased 100 fold in H69AR cells relative to H69 cells. The level of this mRNA in H69PR, a drug sensitive revertant of H69AR, had decreased approximately 20-fold relative to that found in H69AR, further substantiating the correlation of overexpression of this particular mRNA with a multidrug resistance phenotype.

Figure 1B:
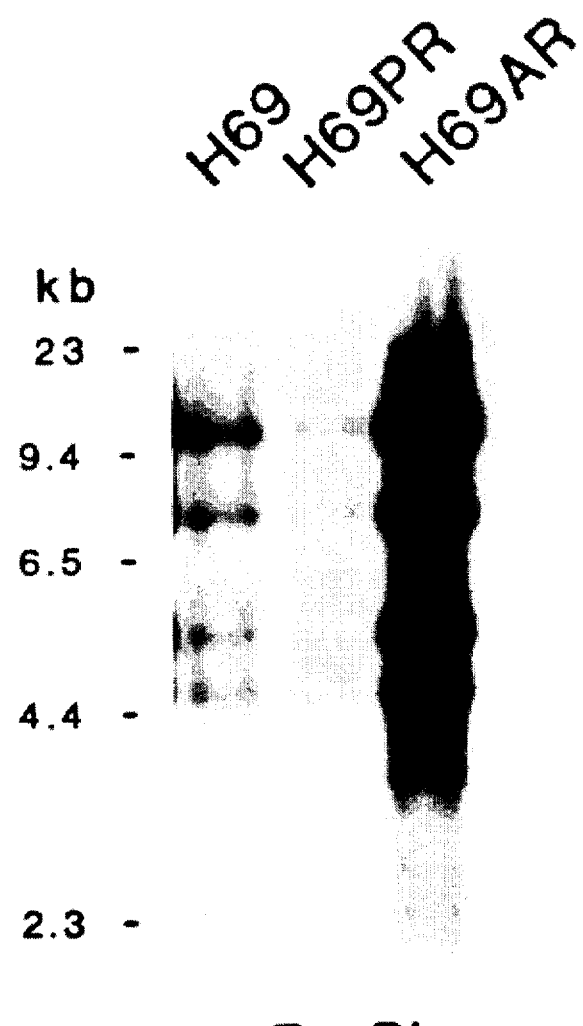
FIG. 1B is a Southern blot analysis of EcoRI—digested genomic DNA from H69, H69AR and H69PR cells hybridized with a 1.8 kb EcoR1 cDNA fragment of the multidrug resistance protein of the invention.

Southern blot analyses of H69, H69AR and H69PR DNA indicated that the major mechanism underlying overexpression was gene amplification. Ten μg of each DNA was digested with EcoRI, electrophoresed through a 0.7% agarose gel and blotted onto a nitrocellulose membrane. The DNA was hybridized with a 1.8 kb EcoRI cDNA fragment of MRP, labelled by random priming with $\alpha$-[$^{32}$P]-dCTP. The autoradiograph shown in FIG. 1B is a 6 hour exposure at $-70°$ C. Based on the examination of several restriction digests and normalization of the amounts of DNA loaded, the MRP gene was amplified 40–50 fold in resistant H69AR cells and no differences in the copy number of the gene in H69 and H69PR cells were detected.

The mRNA was also overexpressed 10–15 fold in a doxorubicin-selected multidrug resistant HeLa cell line that does not overexpress P-glycoprotein (FIG. 1C). S3 and J2c are drug sensitive and resistant HeLa cell lines obtained from the laboratory of Dr. R. M. Baker (Roswell Park Memorial Institute). Two μg of poly(A$^+$)RNA from each cell line was electrophoresed, blotted and probed with MRP cDNA as described for FIG. 1A. The MRP and β-actin autoradiographs shown in FIG. 1C are 18 hour and 1 hour exposures, respectively, at $-70°$ C. Southern blotting of DNA from S3 and J2c cells indicated that the MRP gene was amplified 10–15 fold in the resistant cell line. These findings provide further evidence of the association of elevated levels of this mRNA with multidrug resistance.

The initial 2.8 kb cDNA clone was sequenced, allowing the isolation of overlapping clones by rescreening the H69AR cDNA library with synthetic oligonucleotides. A single, extended open reading frame of 1531 amino acids was defined encoding a protein designated as multidrug resistance associated protein (MRP). The translated GenBank and SwissProt databases were searched for similarities to MRP using the FASTA program. The search revealed that MRP is a novel member of the ATP-binding cassette (ABC) superfamily of transport systems. Members of this superfamily are involved in the energy dependent transport of a wide variety of molecules across cell membranes in both eukaryotes and prokaryotes. Included in this superfamily are the human multidrug transporter P-glycoprotein (MDR1) and the cystic fibrosis transmembrane conductance regulator (CFTR).

EXAMPLE 2

RELATIONSHIP OF MRP TO OTHER MEMBERS OF THE ABC TRANSPORTER SUPERFAMILY

Figure 2:
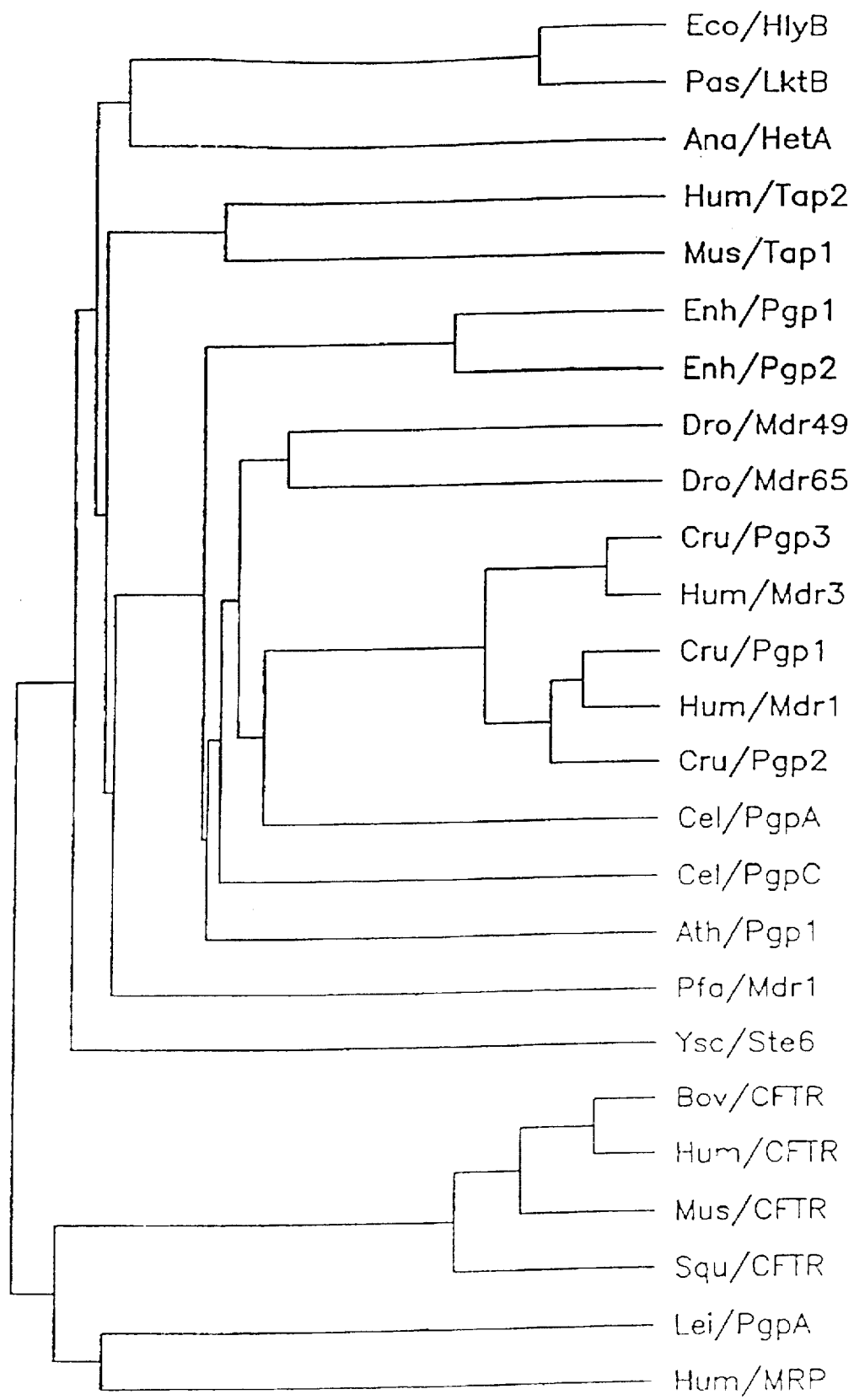
FIG. 2 is a cluster analysis of the relative similarity of the multidrug resistance protein of the invention to selected members of the ATP-binding cassette transporter superfamily that contain hydrophobic transmembrane regions followed by nucleotide binding folds.

The relationship of MRP to the various members of the ABC transporter superfamily was examined using the PILEUP program from the Genetics Computer Group package (version 7) using a modified version of the progressive alignment method of Feng and Doolittle [J. Mol. Evol. 25, 351 (1987)]. A representative selection of a phylogenetically broad range of ABC proteins that are comprised of hydrophobic transmembrane regions followed by nucleotide binding regions, and whose sequences could be retrieved from GenBank and SwissProt databases, were included in this analysis. The analysis divides this family of proteins into two major subgroups (FIG. 2). One of the major subgroups consists of the cluster containing MRP (Hum/MRP), the leishmania P-glycoprotein-related molecule (Lei/PgpA) and the CFTRs (Hum/CFTR, Bov/CFTR, Mus/CFTR and Squ/CFTR). The other subgroup consists of the P-glycoproteins, the MHC class II-linked peptide transporters (Hum/Tap2, Mus/Tap 1), the bacterial exporters (Eco/HlyB, Pas/LktB), the heterocyst differentiation protein (Ana/HetA), the malarial parasite transporter (Pfa/Mdr1) and the yeast mating factor exporter (Ysc/Ste6).

The dendrogram in FIG. 2 indicates that MRP is only distantly related to previously identified members of the ABC transporter superfamily. Although the analysis suggests that it is most closely related to Lei/PgpA, the similarity between MRP and Lei/PgpA resides predominantly in two regions, both containing signatures of nucleotide binding folds (NBFs) (FIGS. 3A-1 to 3A-5). The alignment was generated using PILEUP as described in FIG. 2. The MRP sequence shown was compiled from four overlapping lambda gt11 cDNA clones. The alignment begins at a methionine residue in MRP that aligns with the initiator methionine of Lei/PgpA. The predicted initiator methionine of MRP itself is located 66 amino acids upstream. Identical and conserved amino acids are identified in FIGS. 3A-1 to 3A-5 by double and single dots, respectively. The Walker A and B motifs and the 'active transport' family signature that are characteristic of nucleotide binding folds (NBFs) of ABC transporters are indicated by single lines and denoted A, B, and C, respectively. The predicted transmembrane regions of each protein are indicated by double lines. The region in Lei/PgpA indicated by a dashed line has a mean hydrophobicity value approaching that of a transmembrane region.

Figure 3B:
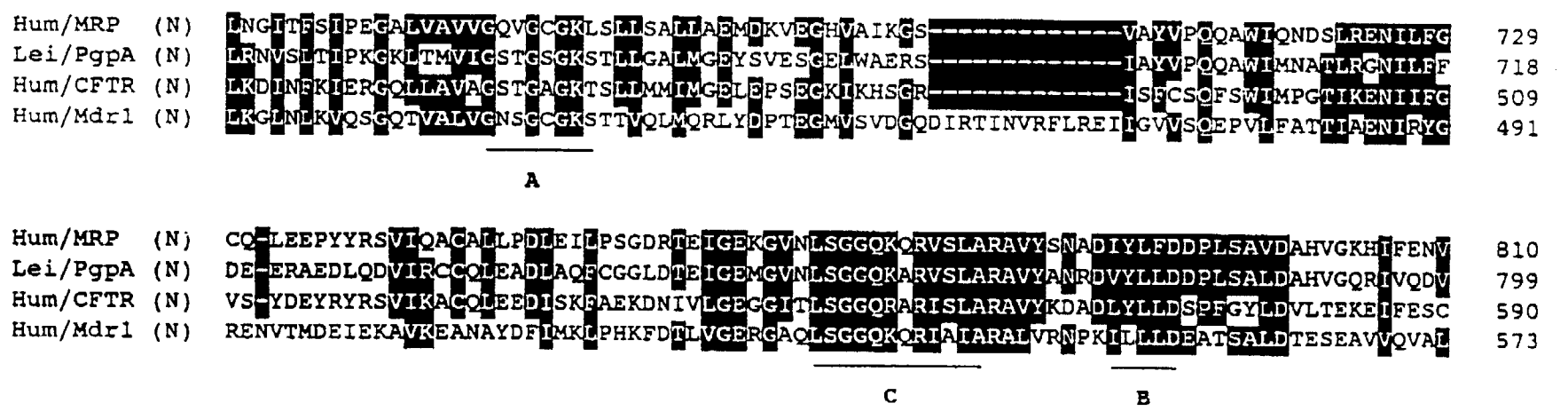
Figure 3B-1:
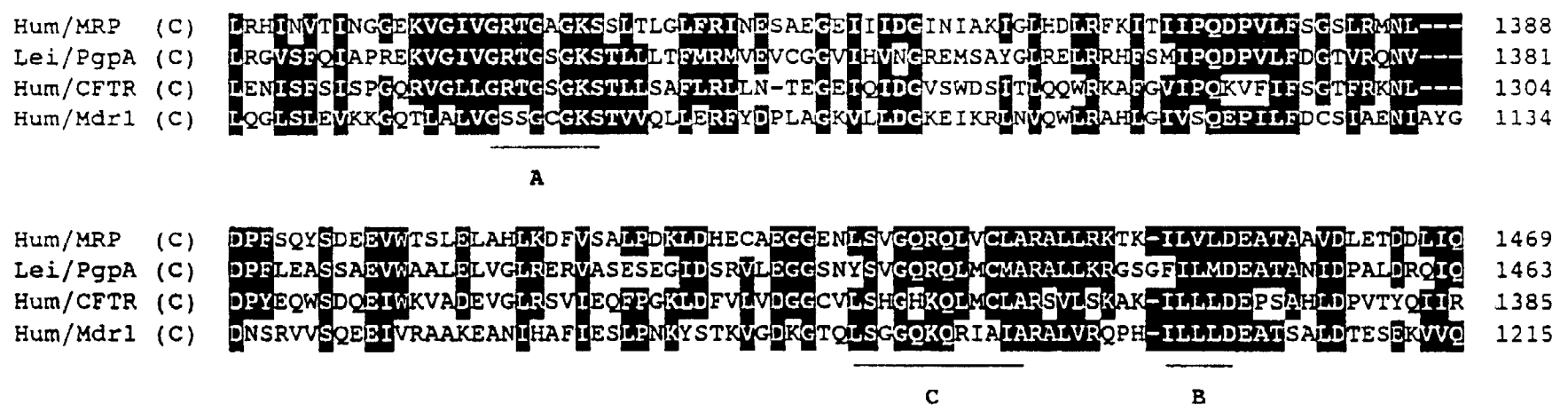

It has been proposed that the bipartite structure of P-glycoproteins reflects duplication of an ancestral gene that occurred prior to the evolutionary separation of animals and plants. However, comparison of the $NH_2$- and COOH-terminal NBFs of MRP and Lei/PgpA revealed less similarity than typically found between the two corresponding regions of P-glycoproteins. To determine whether this was a common structural feature of MRP, Lei/PgpA and Hum/CFTR, their $NH_2$- and COOH-terminal NBFs were aligned with each other and those of several P-glycoproteins. One such comparison using human P-glycoprotein (Hum/Mdr1) as an example is shown in FIGS. 3B and 3B-1. Shown in FIGS. 3B and 3B-1 are the $NH_2$-terminal (N) and COOH-terminal (C) halves of the deduced amino acid sequence of MRP corresponding to ltpgpA (Lei/PgpA) (amino acids 650–799 and 1303–1463), human CFTR (Hum/CFTR) (amino acids 441–590 and 1227–1385), and MDR1 (Hum/Mdr1)(amino acids 410–573 and 1053–1215). The sequences are presented as aligned by PILEUP. Reverse type indicates that 3 of 4 amino acids at that position are identical or conserved. The conserved motifs A, B, and C described in FIGS. 3A-1 to 3A-5 are underscored by a single line. The $NH_2$-terminal NBFs of MRP, Hum/CFTR and Lei/PgpA share structural features that clearly distinguish them from the $NH_2$-terminal NBF of Hum/Mdr1, particularly in the spacing of conserved motifs. This difference in spacing also contributes to the relatively low similarity between $NH_2$- and COOH-terminal NBFs in each of the three proteins. In addition, the COOH-terminal NBFs of MRP, Lei/PgpA and Hum/CFTR are more similar to each other than to either the COOH or $NH_2$-terminal NBFs of Hum/Mdr1. Similarity scores for the $NH_2$-terminal NBFs relative to MRP are: Lei/PgpA (0.93), Hum/CFTR (0.85) and Hum/Mdr1 (0.60). Comparable COOH-terminal scores are Lei/PgpA (0.87), Hum/CFTR (0.84) and Hum/Mdr1 (0.73). Similarity scores for $NH_2$- and COOH-terminal NBFs within the same protein are: MRP (0.61), Lei/PgpA (0.60), Hum/CFTR (0.62) and Hum/Mdr1 (1.10). These observations, combined with the overall analysis shown in FIG. 2, suggest that MRP, Lei/PgpA and CFTR evolved from a common ancestor containing both $NH_2$- and COOH-terminal NBFs, which was distinct, or diverged from the ancestral gene of the P-glycoproteins prior to the animal/plant separation.

EXAMPLE 3

EXPRESSION OF MRP IN NORMAL TISSUES

Figure 4:
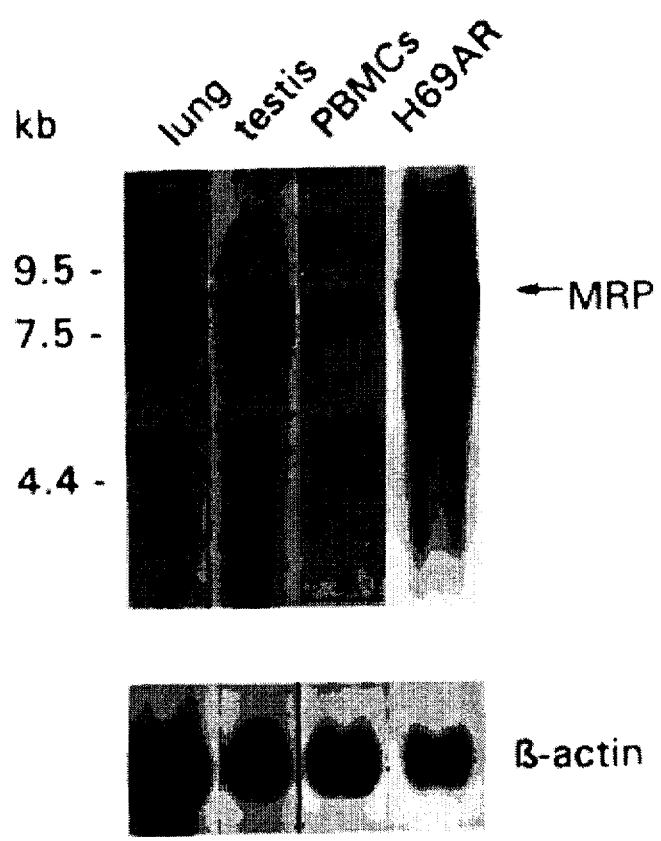
Figure 5:
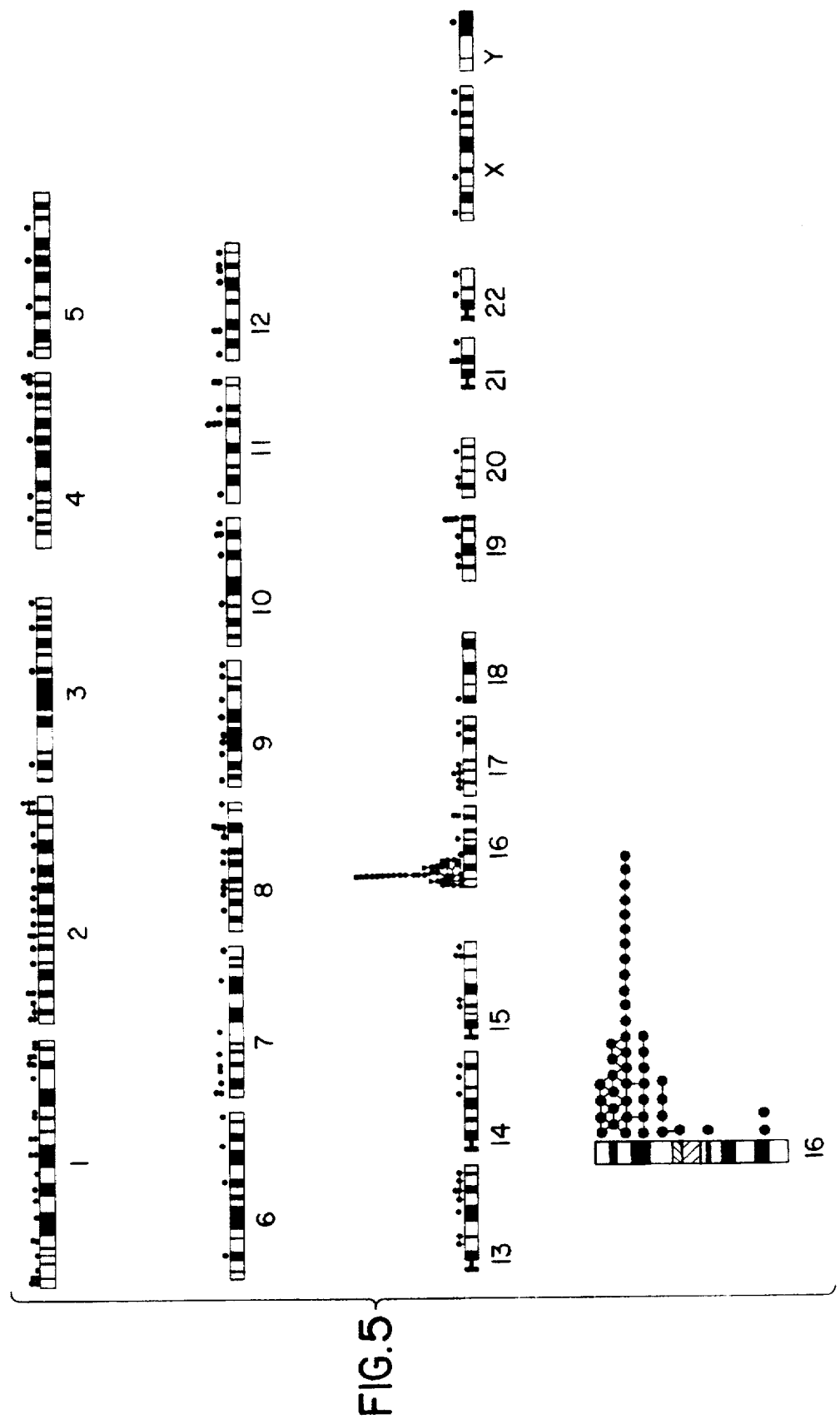

Despite knowledge of its structure and its ability to act as a drug efflux pump, the normal physiological role(s) of P-glycoprotein has not been elucidated. Some possible clues to its function have been provided by its distribution in normal tissues. P-glycoprotein is highly expressed in secretory organs and tissues, such as the adrenals, kidneys, lumenal epithelium of the colon and the murine gravid uterus. It has also been detected in the lung although this finding is variable. Based on the cell types in which it is expressed, it has been postulated that P-glycoprotein may be involved in steroid transport and/or protection against xenobiotics. Northern blot analyses of total RNA preparations from a range of human tissues shown that MRP is expressed at relatively high levels in lung, testis and peripheral blood mononuclear cells (PBMCs)(FIG. 4). Lung and testis RNAs were obtained from Clontech Laboratories (Palo Alto, Calif.). PBMC RNA was prepared from cells isolated by centrifugation over Ficoll-Isopaque (specific gravity 1.078 g/ml; Pharmacia) of peripheral blood from healthy volunteers. Total RNAs from lung, testis and PBMCs (30 μg) and H69AR cells (10 μg) were analyzed as for FIG. 1A. The autoradiograph shown in FIG. 4 is from a blot probed with a 0.9 kb EcoRI cDNA fragment of MRP and exposed for 38 hours for the normal tissue RNAs and for 24 hours for the H69AR RNA. The blot was stripped and reprobed with $^{32}$P-labelled β-actin cDNA. The actin autoradiograph is a 24 hour exposure. MRP transcripts were below the level of detection in placenta, brain, kidney, salivary gland, uterus, liver and spleen.

EXAMPLE 4

MAPPING OF THE HUMAN MRP GENE

The human CFTR and MDR1 genes have been mapped to chromosome 7 at bands q31 and q21, respectively. The possible evolutionary relationship of MRP to these proteins prompted examination of the possibility that the MRP gene may be linked to one of these previously identified loci. In situ hybridization of a 1.8 kb EcoRI fragment of MRP cDNA was performed using the method of Harper and Saunders [Chromosoma 8, 431 (1981)]. Metaphase chromosomes on slides were denatured for 2 minutes at 70° C. in 70% deionized formamide, 2×SSC and then dehydrated with ethanol. The hybridization mixture consisted of 50% deionized formamide, 10% dextran sulfate, 2×SSC (pH 6), 20 μg/ml sonicated salmon sperm DNA and 0.2 μg/ml $^3$H-labelled MRP cDNA. The cDNA probe was labelled to a specific activity of $8.5 \times 10^8$ cpm/μg DNA with [$^3$H]-dTTP and [$^3$H]-dATP (New England Nuclear) using a Multiprime DNA Labelling System (Amersham) and denatured in the hybridization solution at 70° C. for 5 minutes. Fifty μl of the probe solution was placed on each slide and incubated at 37° C. overnight. After hybridization, the slides were washed in 50% deionized formamide, 2×SSC followed by 2×SSC (pH 7) and then dehydrated sequentially in ethanol. The slides were coated with Kodak NTB/2 emulsion and developed after exposure for 5 weeks at 4° C. Chromosomes were stained with a modified fluorescence, 0.25% Wright's stain procedure [C. C. Lin, P. N. Daper, M. Braekeleer, Cytogenet. Cell Genet 39, 269 (1985)]. The positions of 200 silver grains directly over or touching well-banded metaphase chromosomes were recorded on the ISCN-derived idiogram of the human karyotype. A significant clustering of grains (40) was observed in the 16p region (p<0.0001) and the peak of the distribution was at 16p13.1, confirming that MRP was not linked to either CFTR or MDR genes. Approximately 160 metaphases were examined. These results are summarized in FIG. 5.

EXAMPLE 5

EXPRESSION OF MRP IN A DRUG SENSITIVE CELL CONFERS DOXORUBICIN RESISTANCE ON THE CELL

While increased concentrations of MRP and mRNA have been detected in multidrug resistant cell lines derived from a variety of tissues and several of these cell lines have also been shown to contain multiple copies of the MRP gene as a result of amplification and translocation of a region of chromosome 16 spanning the MRP gene at band p13.1, it remained possible, in view of the multistep selection procedures used to derive the cell lines, that overexpression of the MRP gene is only one component of a set of alterations required to confer multidrug resistance. The ability of MRP alone to confer drug resistance on a drug sensitive cell line was determined by constructing an MRP expression vector, transfecting the expression vector into drug sensitive cells and assessing the relative drug resistance of the transfected cell populations.

A DNA fragment corresponding to the complete coding region of MRP mRNA plus 86 nucleotides of 5' and 32 nucleotides of 3' untranslated sequence was assembled and transferred into the expression vector pRc/CMV under the control of the human cytomegalovirus promoter. A DNA fragment containing the complete coding region of MRP mRNA was assembled in the vector, pBluescript 11 KS$^+$ (Stratagene), using overlapping cDNA clones or PCR products generated from these clones. The fidelity of the MRP sequence was confirmed by DNA sequence analysis before moving the intact MRP fragment to the eukaryotic expression vector, pRc/CMV (Invitrogen). The integrity of the MRP fragment in the expression vector was assessed by detailed restriction mapping and DNA sequence analysis of the cloning sites. In the pRc/CMV vector, MRP expression is under the control of the enhancer/promoter sequence from the immediate early gene of human cytomegalovirus. The MRP transcript also contains part of the 3' untranslated region and the polyadenylation signal from bovine growth hormone mRNA which is provided by the vector. Thus, the pRc/CMV-MRP construct generates a transcript of 5.2 to 5.3 kb that includes the entire coding sequence (86 nucleotides of which are derived from MRP mRNA sequence), and approximately 250 nucleotides of 3' untranslated sequence (32 nucleotides of which are derived from MRP mRNA sequence). This vector also contains the bacterial aminoglycoside 3' phosphotransferase gene which confers resistance to geneticin (G418).

HeLa cells were transfected with either the parental vector, or the vector containing the MRP coding region, using supercoiled DNA and a standard calcium phosphate transfection procedure. HeLa cells were transfected with the pRc/CMV vector or the vector containing the MRP coding sequence using a standard calcium phosphate transfection procedure [J. Sambrook, E. F. Firtsch, T. Maniatis, *Molecular Cloning: A Laboratory Manual*, Cold Spring Harbor Laboratory Press, Cold Spring Harbor, N.Y. (1989)]. Approximately, 50,000 cells in each well of a 6-well tissue culture plate were exposed for 16 hours to 10 μg of supercoiled DNA in a calcium phosphate precipitate. After forty-eight hours, the growth medium was changed to include G418 at 200 μg/ml which selected for cells that expressed the neomycin resistance gene encoded by the pRc/CMV vector. Three weeks later, six independently transfected populations of cells were tested for resistance to doxorubicin using a tetrazolium salt microtiter plate assay (S. P. C. Cole, *Cancer Chemother. Pharmacol.* 26, 250 (1990)). Those populations demonstrating increased relative resistance to the drug were expanded for testing for cross-resistance to other cytotoxic drugs, and analysis of MRP mRNA and protein levels.

Poly(A)$^+$ RNA was isolated using the Micro-FastTrack RNA isolation kit (Invitrogen). The RNA was subjected to electrophoresis on a formaldehyde agarose gel and transferred to Zetaprobe membrane (Bio-Rad). The blots were hybridized with $^{32}$P-labeled cDNA fragment probes complementary to the mRNAs for MRP, MDR1 [A. M. Van der Bliek, F. Baas, T. Ten Houte de Lange, P. M. Kooiman, T. Van der Velde Koerts, P. Borst, EMBO J. 6, 3325 (1987)], topoisomerase 11 α [T. D. Y. Chung, F. H. Drake, K. B. Tan, S. R. Per, S. T. Crooke, C. K. Mirabelli, Proc. Natl. Acad. Sci. U.S.A. 86 9431 (1989)], topoisomerase 11 β [ibid.], annexin 11 (S. P. C. Cole, M. J. Pinkoski, G. Bhardwaj, R. G. Deeley, Br. J. Cancer 65, 498 (1992)), and a region of the pRc/CMV vector encoding part of the 3' untranslated region and polyadenylation signal from the bovine growth hormone gene. Hybridization of the probes was quantified by densitometry of the autoradiographs on a Molecular Dynamics Computing Densitometer. Care was taken to compare autoradiographic exposures that were within the linear range of the film. In addition, variations in loading of RNA on the gels were estimated by probing blots with a $^{32}$P-labeled glyceraldehyde-3-phosphate dehydrogenase (GAPDH) cDNA fragment (ATCC/NIH #57090), and by densitometric scanning of the ethidium bromide-stained ribosomal RNA bands on photographic negatives of the RNA gels.

The relative amounts of MRP protein were assessed by immunoblot analysis of total cell extracts and membrane-enriched fractions. Cell pellets were resuspended at $5 \times 10^7$ cells/ml in buffer containing 10 mM Tris-HCl, pH 7.4, 10 mM KCl, 1.5 mM $MgCl_2$, and protease inhibitors (2 mM phenylmethylsulfonyfluoride, 50 µg/ml antipain, 2 µg/ml aprotinin, 200 µg/ml EDTA, 200 µg/ml benzamidine, 1 µg/ml pepstatin). After 10 min on ice, cells were homogenized with approximately 80 strokes of a Tenbroeck homogenizer. The homogenate was adjusted to 250 mM in sucrose before remaining intact cells and nuclei were removed by centrifugation at 800×g at 4° C. for 20 min. To prepare a membrane-enriched fraction, the supernatant was centrifuged at 100,000×g at 4° C. for 20 min in a Beckman TL-100 ultracentrifuge and the pellet resuspended in 10 mM Tris-HCl, pH 7.4, 125 mM sucrose, and the protease inhibitors listed above. For sodium dodecyl sulphate (SDS) polyacrylamide gel electrophoresis and immunoblotting, appropriate amounts of protein were mixed 1:1 with solubilizing buffer (final concentration 4M urea, 0.5% SDS, 50 mM dithiothreitol). Samples were loaded without heating onto a 7% resolving gel with a 4% stacking gel. Proteins were transferred to Immobilon-P PVDF membranes (Millipore) using 50 mM 3-(cyclohexylamino)- 1-propanesulfonate, pH 11.0. For detection of MRP, blots were incubated with an affinity-purified, rabbit polyclonal antibody raised against a synthetic peptide, the sequence of which was predicted from that of the cloned MRP cDNA and which is not found in any other known protein. Antibody binding was visualized with horseradish peroxidase-conjugated goat anti-rabbit IgG and enhanced chemiluminescence detection (Amersham). The affinity-purified anti-MRP antibody recognizes a glycosylated, integral membrane protein with an apparent molecular weight of 190 kilodaltons. In its deglycosylated form, the molecular weight of the protein decreases to 165- to 170 kilodaltons which is in agreement with the molecular weight of 171 kilodaltons predicted from the primary amino acid sequence of MRP.

At this time, the level of G418 in the growth medium was increased to 400 or 800 µg/ml without any noticeable effect on the growth rate of cells transfected with either the parental vector or the vector containing the MRP coding sequence. Transfected populations have been grown continuously for up to four months in G418-containing medium without any change in the level of resistance to doxorubicin. Integration of these vectors into genomic DNA has the potential to alter the expression of endogenous genes that might adventitiously increase drug resistance. Consequently, chemotherapeutic drugs were not used as selecting agents. Populations of transfected cells were selected solely by their ability to grow in the presence of G418. Since cells overexpressing MRP do not display increased resistance to this antibiotic, variable levels of expression of MRP are to be expected in the transfected cell populations.

Figure 6:
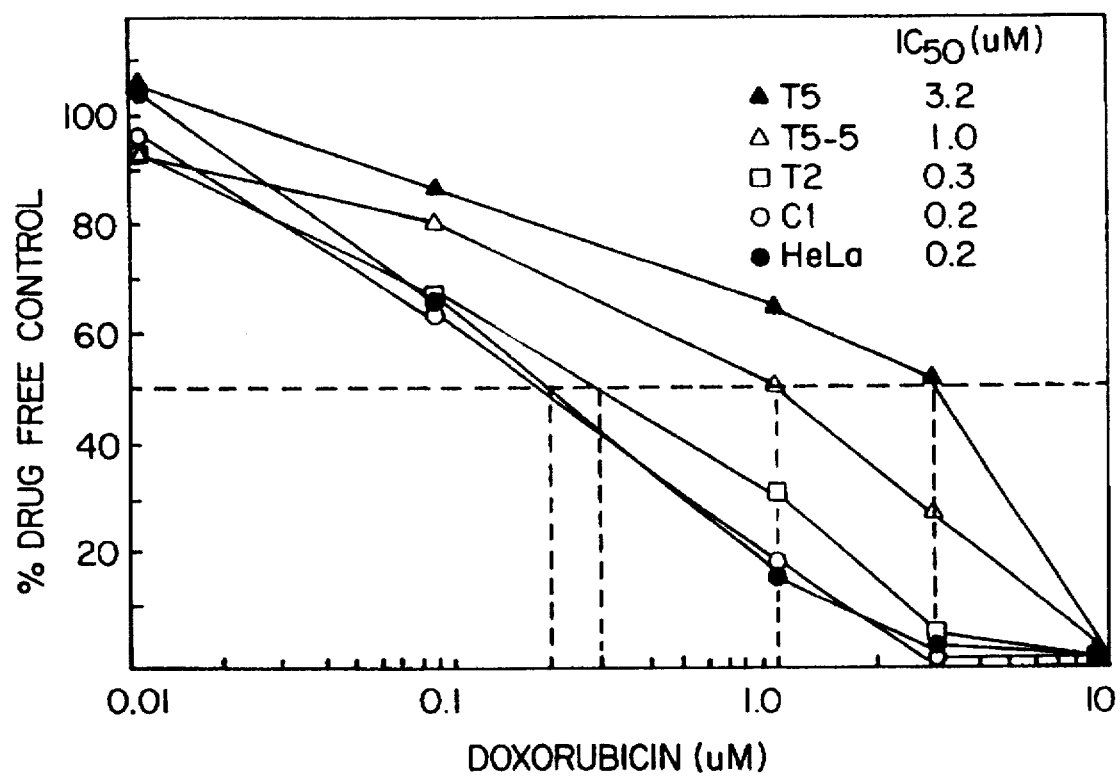
FIG. 6 is a graph depicting the relative cytotoxicity of doxorubicin on MRP-transfected HeLa cell populations (T2, T5), a clone of the T5 population (T5-5), untransfected HeLa cells and HeLa cells transfected with the parental expression vector (C1).

The relative resistances to doxorubicin are shown for two examples of G418 resistant cell populations transfected with the MRP expression vector (T2 and T5), as well as untransfected HeLa cells and a population transfected with the parental vector (C1) (FIG. 6). Key: HeLa cells (●); HeLa cells transfected with the expression vector pRc/CMV (C1, ○); HeLa cells transfected with the vector containing the MRP coding sequence (T2, □; T5, △); and a clone isolated from the doxorubicin-resistant transfected T5 cells shown (△, T5-5). Each point represents the mean of triplicate determinations in a single experiment and standard deviations were <5%. Similar results were obtained in three additional experiments. The $IC_{50}$ is indicated on the figure and is defined as the concentration of doxorubicin required to decrease by 50% the values obtained with untreated cells. In the examples shown, one of the populations transfected with the MRP expression vector (T2) displayed little change in doxorubicin resistance while resistance of the other (T5) was increased 15-fold. In addition, several clones from the resistant population were grown in the presence of G418 and their degree of doxorubicin resistance determined. Dose response curves for two of the transfectants (T2, T5) and for one of the clones (T5-5) were then compared to determine whether their resistance to doxorubicin correlated with the concentrations of MRP mRNA.

Figure 7A:
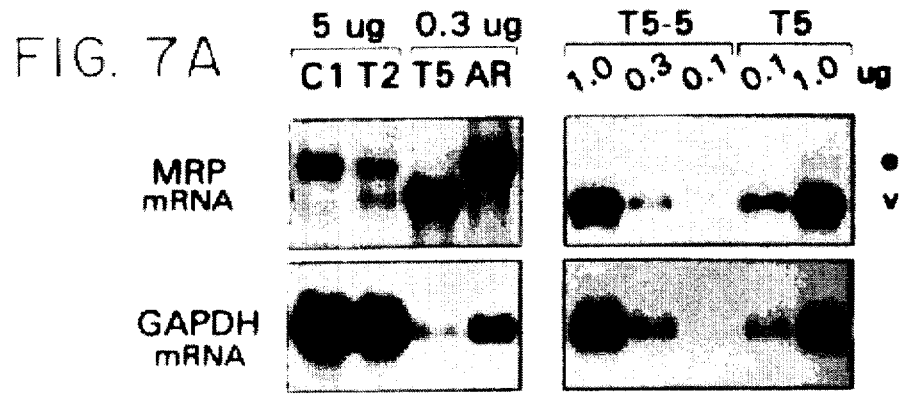
FIG. 7A is a Northern blot of poly(A)+ RNA from transfected and control HeLa cells hybridized with a 4 kb MRP cDNA fragment which hybridizes with endogenous MRP mRNA (e) and expression vector-derived MRP mRNA (v). Hybridization with a GAPDH cDNA demonstrates the relative amounts of poly(A)+ RNA in each lane.
Figure 7B:
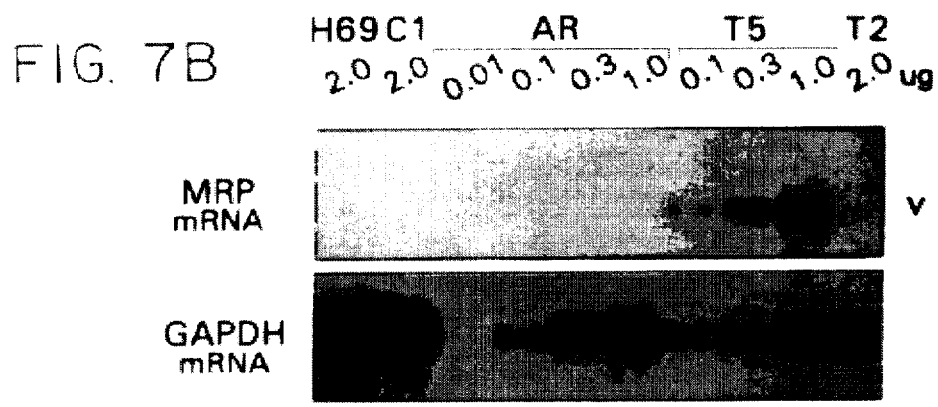
FIG. 7B is a Northern blot of poly(A)+ RNA from transfected HeLa cells and control cells hybridized with a DNA fragment from the pRc/CMV vector which hybridizes only to expression vector-derived MRP mRNA (v). Hybridization with a GAPDH cDNA demonstrates the relative amounts of poly(A)+ RNA in each lane.

The MRP mRNA produced from the expression vector has a predicted length of 5.2 to 5.3 kb including a poly(A) tail, thus allowing it to be distinguished from the longer, endogenous MRP mRNA by Northern analysis. A blot of poly(A)$^+$ RNA from the cell populations shown in FIG. 6 that was hybridized with a cloned cDNA probe corresponding to part of the MRP coding sequence, revealed a relatively abundant mRNA of approximately 5.3 Kb in the resistant transfectants and low levels of the endogenous MRP mRNA (FIG. 7A). The relative concentration of the 5.3 kb mRNA is 70- to 80-fold and 20- to 30-fold higher in the resistant cell population (T5) and clone (T5-5), respectively, than that of endogenous MRP mRNA present in the control population (C1). Relative levels of mRNAs were determined by densitometry and normalization to the levels of GAPDH mRNA. Expression of the 5.3 kb MRP mRNA in the transfected cell population which showed little change in resistance (T2) was only approximately half that of endogenous MRP mRNA. Similar RNA blots were also probed with a DNA fragment from the pRc/CMV plasmid that forms part of the 3 ' untranslated region of the vector encoded MRP mRNA. This probe hybridized only with the 5.3 kb MRP mRNA, confirming that it was transcribed from the vector and did not result from the increased expression of an endogenous MRP-related gene (FIG. 7B). Thus in cells transfected with the MRP expression vector the relative level of drug resistance increases with the concentration of MRP mRNA.

Figure 7C:
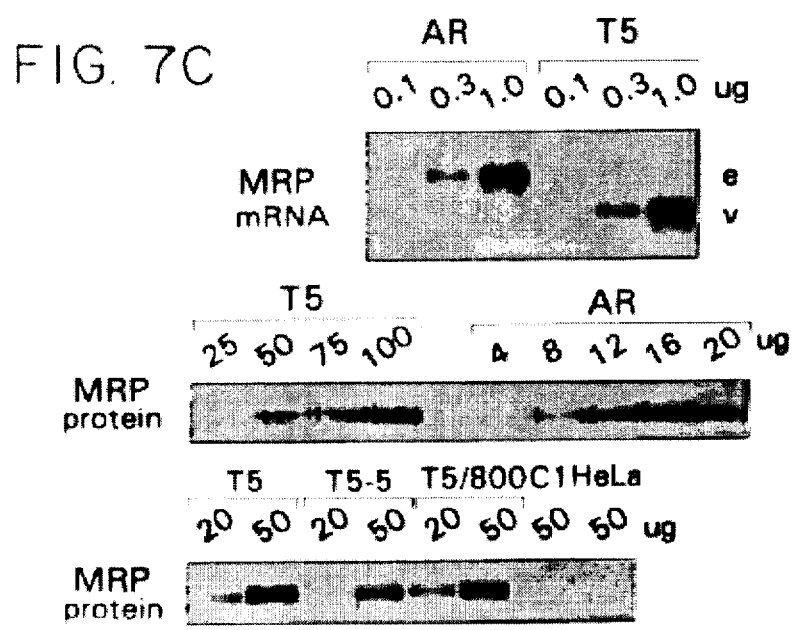
FIG. 7C is a Northern blot (MRP mRNA) and immunoblots (MRP protein) depicting the relative levels of expression vector-derived MRP mRNA and protein in transfected HeLa cells and endogenous MRP mRNA and protein in the H69AR cell line.

The concentration of endogenous MRP mRNA in the multidrug resistant H69AR cells (labeled AR in the figures) is approximately 100-fold higher than in the H69 parental cells (labeled H69 in the figures) and the relative resistances of the two cell lines to doxorubicin also differ by 50- to 100-fold. Vector encoded MRP mRNA levels in the T5 HeLa cell population are 70- to 80-fold higher than endogenous MRP mRNA levels in the parental cells. However, drug resistance is increased only 15-fold. To investigate why the relative increase in drug resistance was lower in the transfectants than in H69AR cells, we compared the levels of MRP mRNA and protein in the two different cell types. Northern analysis revealed that the levels of endogenous MRP mRNA in H69 cells and HeLa cells transfected with the pRc/CMV parental vector were similar. The relative abundance of vector encoded MRP mRNA in the drug resistant transfectant cell population (T5) was also comparable to that of endogenous MRP mRNA in H69AR cells (FIG. 7C). However, a protein blot with affinity purified anti-MRP antibody indicated that the level of protein in the T5 HeLa cell transfectants was 5- to 8-fold lower than in H69AR cells (FIG. 7C). These findings are consistent with the 15-fold increase in resistance observed in the transfected T5 cells compared to the 50- to 100-fold increase in H69AR cells. The lower level of protein in the transfected cells in most likely attributable to a difference in translational efficiency between the vector encoded and endogenous MRP mRNAs, although a difference in rates of degradation of the protein between the two cell types cannot be excluded.

Figure 8A:
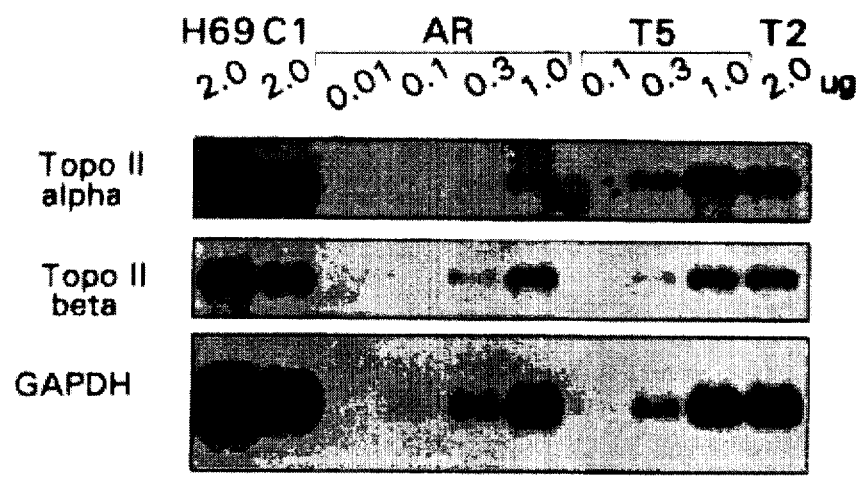
FIG. 8A is a Northern blot of poly(A)+ RNA from transfected HeLa cells and control cells hybridized with cDNA probes for topoisomerase II (Topo II) alpha and beta mRNAs. Hybridization with a GAPDH cDNA demonstrates the relative amounts of poly(A)+ RNA in each lane.
Figure 8B:
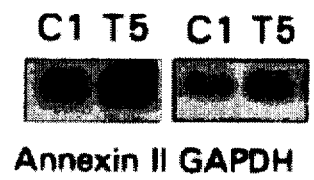
FIG. 8B is a Northern blot of poly(A)+ RNA from transfected HeLa cells and control cells hybridized with a cDNA probe for annexin II mRNA. Hybridization with a GAPDH cDNA demonstrates the relative amounts of poly (A)+ RNA in each lane.

Since H69AR cells were obtained by multistep selection, it is possible that additional alterations have occurred which may, either independently or in concert with MRP, influence their degree of resistance to some drugs. H69AR cells have been shown to have decreased levels of topoisomerase 11 α and β mRNA and protein which could enhance their resistance to anthracyclines and epipodophyllotoxins. They have also been shown to overexpress annexin 11 which may affect the trafficking of membrane proteins. Annexin 11 has been shown to be involved in formation of fusogenic vesicles and in exocytosis. S. P. C. Cole, M. J. Pinkoski, G. Bhardwaj, R. G. Deeley, Br. J Cancer 65, 498 (1992). It is unknown to what extent these additional changes influence the degree of resistance of H69AR cells or whether they are linked in any way to overexpression of MRP. However, overexpression of MRP in the transfected cells does not alter the levels of mRNAs specifying either topoisomerase 11 isoform (FIG. 8A) or annexin 11 (FIG. 8B), nor do the transfected HeLa cells display any alterations in the level of Mdr1 mRNA. These observations strongly support the conclusion that increased resistance to doxorubicin in the transfected cells is directly attributable to overexpression of MRP.

EXAMPLE 6

EXPRESSION OF MRP IN A DRUG SENSITIVE CELL CONFERS MULTIDRUG RESISTANCE ON THE CELL

Figure 9A:
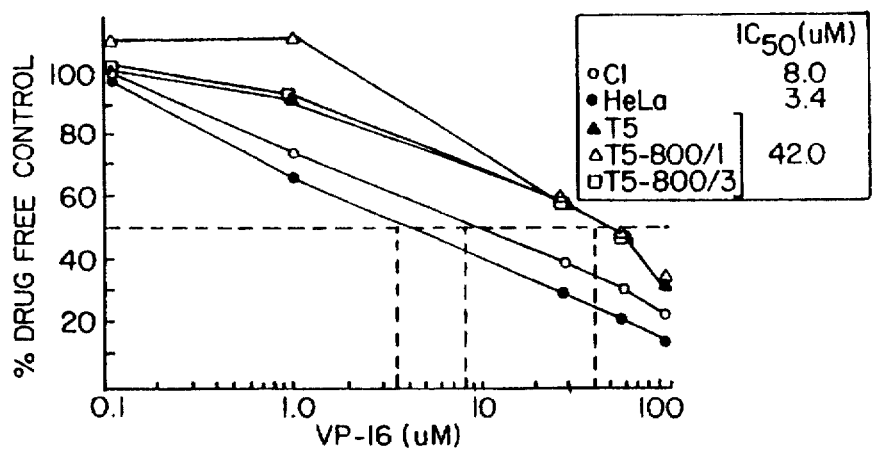
FIGS. 9A to 9C show the relative cytotoxicity of VP-16, vincristine and cisplatin, respectively, on MRP-transfected HeLa cell populations (T5-800/1, T5-800/3), a clone of the T5 population (T5), untransfected HeLa cells and HeLa cells transfected with the parental expression vector (C1).
Figure 9B:
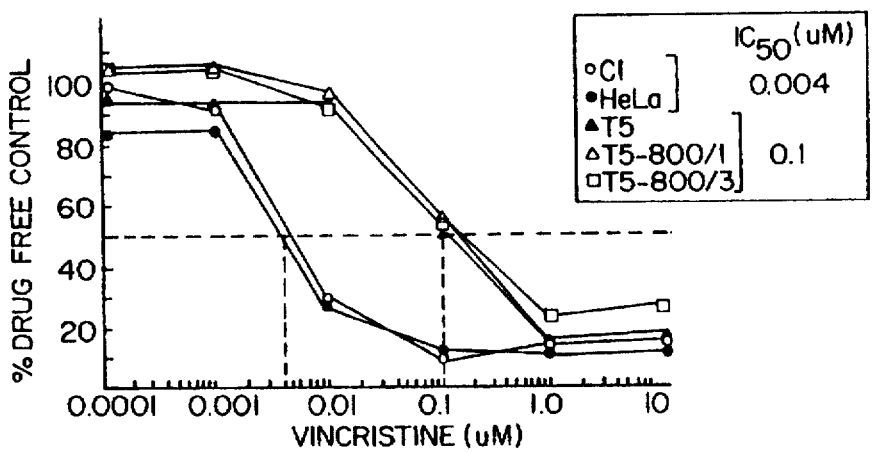
Figure 9C:
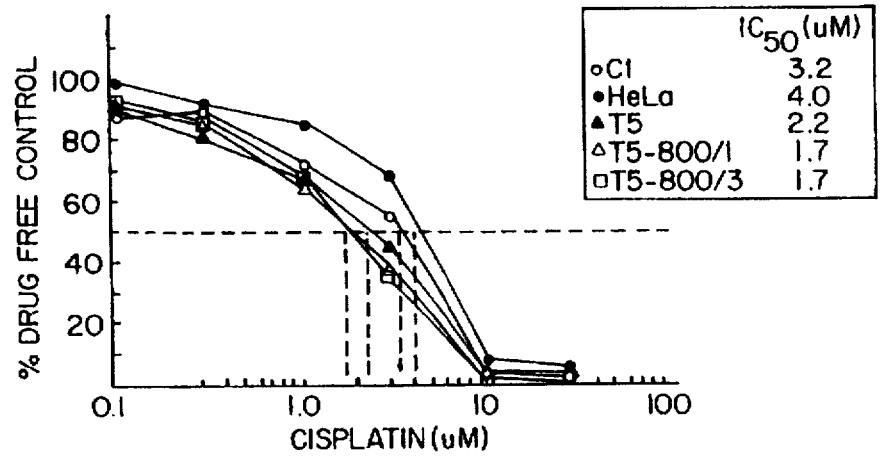

To determine whether the increased doxorubicin resistance of transfected cells was accompanied by increased resistance to other classes of chemotherapeutic drugs, the cells were tested for cross-resistance to VP-16 (an epipodophyllotoxin), vincristine (a Vinca alkaloid), and cisplatin (FIGS. 9A to 9C). Cytotoxicity assays were performed on untransfected HeLa cells (●), HeLa cells transfected with the expression vector pRc/CMV (C1, ○), HeLa cells transfected with the expression vector pRc/CMV-MRP and maintained in G418 at 400 µg/ml for 4 months (T5, ▲), and T5 cells maintained at 800 µg/ml G418 for 1 month (T5-800/1, △) and 3 months (T5-800/3,□). Each point represents the mean of triplicate determinations in a single experiment and standard deviations were <5%. Similar results with vincristine and VP-16 were obtained in two to three additional experiments. The $IC_{50}$'s of the various cell lines are indicated on the figure. Dose response curves for several independently propagated cultures of MRP transfectants indicate that they are approximately 25-fold and 5- to 10-fold resistant to vincristine and VP-16, respectively, relative to untransfected HeLa cells or cells transfected with parental vector (C1). The transfectants showed no increase in cisplatin resistance which is consistent with the pharmacological phenotype of H69AR cells and which is also characteristic of cells that overexpress P-glycoprotein. These results demonstrate for the first time that this phenotype can be conferred by a member of the ABC superfamily of transporters that is structurally very different from the P-glycoproteins.

EXAMPLE 7

PREPARATION OF ANTI-MRP ANTIBODIES USING MRP PEPTIDES AS THE IMMUNOGEN

MRP is encoded by a mRNA of approximately 6.5 kb with an extended open reading frame of 1531 amino acids. The protein is predicted to contain two nucleotide binding folds (NBFs) and 12 transmembrane regions, divided 8 and 4 between the NH2- and COOH-proximal halves of the molecule, respectively. To confirm that a protein of the predicted size and sequence is overexpressed in resistant H69AR cells, polyclonal antibodies were prepared against synthetic peptides based on the deduced amino acid sequence of MRP and used in immunoanalyses.

One peptide of sequence AELQKAEAKKEE was selected from the highly divergent cytoplasmic linker domain of MRP (MRP-L, position 932–943) while the second peptide (GENLSVGQRQLVCLA) was chosen from the second nucleotide binding domain of MRP (MRP-2, position 1427–1441). Both peptides were synthesized on Ultrasyn D resin for direct immunization by the Biotechnology Service Centre at the Hospital for Sick Children (Toronto, Ont.). Approximately 400 µg of bound peptide was resuspended in distilled water and sonicated. The resulting suspension was emulsified in an equal volume of complete Freund's adjuvant (Difco) and injected s.c. at four sites in 3-month old female New Zealand White rabbits. At 2- to 3-week intervals, the same amount of immunogen emulsified in incomplete Freund's adjuvant was injected s.c. Rabbits were bled by arterial puncture beginning 2 weeks following the third immunization and their sera were tested for the presence of antibodies by an enzyme-linked immunosorbent assay (ELISA) and by immunoblotting.

Rabbit antisera obtained after immunization with peptide MRP-L that were positive by ELISA or western blotting were concentrated by ammonium sulfate precipitation and purified by affinity chromatography. Affinity columns were constructed by coupling the MRP-L peptide to CNBr-activated Sepharose (5 µmole peptide/ml gel) according to the instructions of the supplier (Pharmacia LKB Biotechnology Inc.) followed by extensive washing with 10 mM Tris, pH 7.5. The ammonium sulfate precipitate was dissolved in phosphate-buffered saline, dialyzed extensively against the same buffer and then applied to the prewashed affinity column. The loaded column was washed first with 10 mM Tris pH 7.5 followed by 10 mM Tris, pH 7.5, 0.5M NaCl before eluting the antibody with 0.1M glycine, pH 2.5. Fractions were neutralized in collection tubes containing 1M Tris, pH 8.0. The desired fractions were pooled, dialyzed extensively against phosphate-buffered saline and concentrated by Amicon concentrators/filtration. The final protein concentration of the purified antibody was adjusted to 0.7–1.5 mg/ml. Rabbit antisera obtained after immunization with peptide MRP-2 were used without further purification.

ELISA positive antisera from these rabbits were used in immunoblot analyses. Polyacrylamide gel electrophoresis was carried out by the method of Laemmli with a 5% or 7% separating gel and a 4% stacking gel. Samples were diluted 1:1 in solubilizing buffer to a final concentration of 4M urea, 0.5% SDS, 50 mM DTT and loaded on the gels without heating. For immunoblotting, proteins were transferred after gel electrophoresis to Immobilon-P PVDF membranes (Millipore, Mississauga, Ont.) using 50 mM CAPS, pH 11.0. Blots were incubated for 1 h in blocking solution (5% normal goat serum/5% HyClone serum/1% BSA) in TBS-T (10 mM Tris, pH 7.5, 0.05% Tween 20, 150 mM NaCl). Anti-MRP antibodies were added directly to the blocking solution and incubated for 2 h. The blot was washed 3×5 min in TBS-T and goat anti-rabbit IgG horseradish peroxidase-conjugate [affinity purified F(ab')2 fragment (Jackson ImmunoResearch) or whole molecule (ICN Biomedicals)] diluted in blocking buffer added. After a 1 h incubation, the blot was washed 5×5 min in TBS-T, and antibody binding detected by ECL (Amersham, UK) and exposure on Kodak XOMAT film. The antisera detected a 190 kD protein in resistant H69AR cells which was not detectable in sensitive H69 and revertant H69PR cells.

The antisera were also used in immunoprecipitation experiments using cell membrane preparations of cells metabolically labelled with $^{35}$S-methionine. Cells were cultured in 50 µCi/ml $^{35}$S-methionine (Tran $^{35}$S-label; cell labelling grade; specific activity, 710 Ci/mmol) (Dupont NEN) overnight in methionine-deficient RPMI 1640 medium (Sigma) or with 500 µCi/ml $^{32}$P-orthophosphoric acid (Carrier free, 500 mCi/ml) (Dupont NEN) in phosphate-deficient RPMI 1640 medium (ICN) for 4 h. Crude radiolabelled 100,000×g membrane-enriched fractions were prepared and immunoprecipitated as follows. Frozen or fresh cells (50×10$^6$/ml) were suspended in 10 mM Tris-HCl, pH 7.4 containing 10 mM KCl, 1.5 mM MgCl$_2$ with protease inhibitors (2 mM phenylmethylsulfonylfluoride, 50 µg/ml antipain, 2 µg/ml aprotinin, 200 µg/ml EDTA, 200 µg/ml benzamidine, 0.5 µg/ml leupeptin, 1 g/ml pepstatin) and 0.025 mg/ml RNase A and 0.05 mg/ml DNase 1. After 10 min., the suspension was homogenized in a chilled Tenbroeck homogenizer with 80 strokes of the pestle. The homogenate was then centrifuged at 800×g at 4° C. for 15 min. to remove nuclei and remaining intact cells. A membrane-enriched fraction was prepared by ultracentrifugation of the supernatant at 100, 000×g at 4° C. for 20 min. The pellets were resuspended in 10 mM Tris HCl, pH 7.6 with 125 mM sucrose and protease inhibitors as above. Protein concentrations were determined by the Peterson modification of the Lowry assay and aliquots were stored at −80° C.

Proteins were solubilized in 1% CHAPS, 100 mM KCl, 50 mM Tris-HCl, pH 7.5, at a detergent to protein ratio of 20:1 for 1 h at 4° C. with frequent vortexing followed by centrifugation at 100,000×g for 20 min using a T100.3 rotor in a Beckman Ultracentrifuge. The supernatant (whatever percentage of protein is solubilized from an initial 40 µg of membrane protein) was incubated with affinity purified MRP-L antisera (25 µg solubilized in 1% CHAPS, 100 mM KCl, 50 mM Tris-HCl, pH 7.5) overnight at 4° C. The samples were made up 700 µl with 1% CHAPS buffer then incubated with 50 µl (10% w/v) Protein A Sepharose Cl-4B (Pharmacia) for 3 h at 4° C. with gentle rocking. The samples were centrifuged for 10 sec at 14,000×g and sequentially washed for 5 min with 1 ml each of Buffer 1 (10 mM Tris-HCl, pH 8.0, 0.5 mM NaCl, 0.5% Nonidet P-40, 0.05% SDS), Buffer 2 (10 mM Tris-HCl, pH 8.0, 0.15M NaCl, 0.5% Nonidet P-40, 0.05% SDS, 0.5% deoxycholate) and Buffer 3 (10 mM Tris-HCl, pH 8.0, 0.05% SDS). The washed beads were incubated with 100 µl of 4M urea, 0.5% SDS, 50 mM DTT for 1 h at room temperature with frequent vortexing. The samples were centrifuged and the supernatants analyzed on 7% polyacrylamide gels. The gels were fixed in isopropanol:water:acetic acid (25:65:10) for 30 min followed by the addition of the fluorographic reagent Amplify (Amersham). The gels were dried and then exposed to film overnight at −80° C. A 190 kD protein was detectable by immunoprecipitation of membrane-associated proteins from $^{35}$S-methionine labelled H69AR cells with the immunoreactive antisera.

The apparent molecular weight of the immunodetectable 190 kD protein in the H69AR cell membranes is approximately 20 kD greater than the predicted 171 kD molecular weight of MRP based upon the deduced primary amino acid sequence. However, analysis of the MRP sequence indicates the presence of three potential N-glycosylation sites in regions predicted to be asymmetrically distributed about a membrane bilayer. To determine whether or not the 190 kD protein was N-glycosylated, two sets of experiments were carried out. First, resistant H69AR cells were grown in the presence of tunicamycin, a potent inhibitor of N-linked glycosylation. N-linked glycosylation was inhibited in H69AR cells by culturing in 15 µg/ml tunicamycin (Sigma) for 24 h. Treated cells were washed twice with phosphate-buffered saline and then whole cell lysates were prepared by homogenization in lysis buffer (20 mM Tris HC, pH 7.5, 20 mM KCl, 3 mM MgCl2, 0.5 mg/ml DNase 1, 0.25 mg/ml RNase A) with protease inhibitors as described above. Polyacrylamide gel electrophoresis and immunoblotting of the whole cell lysates were carried out as before. In the second approach, H69AR 100,000×g membranes were incubated with the deglycosylase PNGase F. Membrane-enriched fractions (200 µg protein) were diluted to a final concentration of 1 µg/µl in 50 mM Na phosphate buffer, pH 7.5, containing 25,000 NEB units PNGase F (New England Biolabs). After 8 h at 37° C., an additional 25,000 NEB units PNGase F was added followed by incubation overnight at 37° C. Sample buffer was added directly and SDS-PAGE and immunoblotting carried out as before. In both cases, a 170 kD protein was detected by immunoblot analyses which correlates well with the 171 kD predicted molecular weight of MRP. Similar results were observed with cells transfected with a full-length MRP cDNA (T5 cells) (see Almquist, et al. *Cancer Research* 55:102–110 (1995).

To confirm that MRP is an ATP-binding protein, as suggested by the presence of ATP-binding signature motifs, membranes from resistant H69AR and sensitive H69 cells were photolabelled with $^{32}$P-8-azido ATP. Crude membrane-enriched fractions were resuspended at 1 µg/µl protein in 10 mM Tris-HCl, pH 7.6, buffer containing 1 mM MgCl$_2$ and protease inhibitors as described above. After the addition of 3-4 µCi$^{32}$P-8-azido-ATP (specific activity 2–10 Ci/mmol; ICN Biomedical, Mississauga, Ont.), incubation on ice was continued for 1–5 min. The azido-ATP was cross-linked to the protein on ice by irradiation at 366 nm about 10 cm from the light source for 8 min. using a Stratalinker set at 1100 µW. The labelled proteins were stored at −80° C. until polyacrylamide gel electrophoresis or immunoprecipitations were carried out. Specificity of the labelling was confirmed by competition with cold excess ATP (Boehringer Mannheim, Laval, Que.) which was added to the membrane preparations prior to the addition of $^{32}$P-8-azido-ATP. These studies revealed strong, specific labelling of a 190 kD protein in membranes from the H69AR cells that was not detected in drug sensitive H69 cells. Our results indicate that in H69AR cells, the MRP gene encodes an N-glycosylated ATP-binding protein of 190 kD.

EXAMPLE 8

PREPARATION OF ANTI-MRP MONOCLONAL ANTIBODIES

In this Example, monoclonal antibodies reactive against MRP were prepared by immunizing mice with a multidrug resistant cell (H69AR) that expresses MRP followed by isolation of antibody-producing cells, fusion with immortalized cells and selection of specific monoclonal antibodies. The following methodologies were used:

Cell Culture

The parental H69, doxorubicin-selected multidrug resistant H69AR, and revertant H69PR small cell lung cancer cell lines were maintained as described in Mirski, S. E. L. et al. (1987) Cancer Res. 47:2594–2598; Cole, S. P. C. et al. (1992) Br. J. Cancer 65:498–502. T5 cells (HeLa cells that have been made multidrug resistant by transfection with a full length MRP cDNA expression vector, pRc/CMVMRP1) and C1 cells (HeLa cells that have been transfected with pRc/CMV vector alone), were maintained in the same medium as the lung cancer cells, supplemented with 400 µg/ml G-418 (Sigma Chemical Co., St. Louis, Mo.). SP2/0Ag14 myeloma cells (ATCC# CRL 1581) were maintained in DMEM (Hybri-Max, Sigma) supplemented with 4 mM L-glutamine and 5% heat inactivated bovine calf serum. Approximately one week prior to fusion, Sp2/0 cells were challenged with 0.132 mM 8-azaguanine (Sigma) for one passage.

Generation of Hybridomas

Membrane-enriched cell fractions were prepared and resuspended in Tris-sucrose buffer (10 mM Tris HCl, pH 7.5, 0.25M sucrose) containing protease inhibitors. Female BALB/c mice (6–8 weeks old) received three i.p. injections of 150 µg H69AR membrane protein (without detergent) in PBS and mixed 1:1 with an emulsion of monophosphoryl lipid A (MPL), synthetic trehalose dicorynomycolate (TDM) and cell wall skeleton (CWS) (obtained commercially from RIBI ImmunoChem Research, Inc., Hamilton, Mont.) at approximately three week intervals. Three days before fusion, 100 µg H69AR membrane protein was injected i.v. into a tail vein. Spleen cells were fused with SP2/0 myeloma cells with polyethylene glycol 4000 (Sigma Chemical Co., St. Louis, Mo.) according to standard methods (see e.g., Kennett, R. H. (1979) Meth. Enzymol. 58:345–359; Mirski, S. E. L. et al. (1989) Cancer Res. 49:5719–5724). Cultures were fed with DMEM medium containing 100 µM hypoxanthine, 0.4 µM aminopterin, 16 µM thymidine, 20% heat-inactivated fetal bovine serum and gentamycin (25 µg/ml) (ICN Biomedicals, St. Laurent, Quebec, Canada). After initial screening, aminopterin was omitted from the growth medium.

Screening, Cloning, Isotyping and Ascites Production

After 11 days of growth in selective medium, 459 hybridoma supernatants were tested for the presence of MRP-specific antibody by immunodot blot analysis. H69, H69AR, and H69PR membrane proteins in TBS were blotted (4 µg protein/dot) onto Immobilon-P PVDF membrane (Millipore, Mississauga, Ontario, Canada) using a 96-well vacuum manifold and blots were kept wet at all times. The blots were cut into strips such that each strip had spots of membrane proteins from each of the three cell lines. After transfer to 24-slot incubation trays, strips were blocked for 1 h in blocking solution (5% bovine calf serum/5% normal goat serum/1% BSA in TBS-T). Hybridoma supernatants were added directly to the blocking solution at a final dilution of 1:9. After 90 min, the strips were washed 3×5 min in TBS-T, and secondary antibody (horseradish peroxidase-conjugated goat anti-mouse IgG+IgM (H+L), F(ab')2 fragment) (Pierce, Edmonton, Alberta) was added (diluted 1:10,000 in blocking buffer). After 1 h, the strips were washed 5×5 min in TBS-T, and antibody binding was determined by enhanced chemiluminescence detection (Amersham, Oakville, Ontario, Canada) and exposure on Kodak X-OMAT film.

Hybridomas which showed preferential reactivity with H69AR membrane dots were subjected to a second immunodot blot, using strips with C1 and T5 membrane protein dots in addition to the H69, H69AR, and H69PR dots. Hybridomas which reacted preferentially with H69AR and T5 membrane dots compared to H69, H69PR, and C1 dots were cloned twice by limiting dilution and then expanded.

Immunoglobulin subtypes of the MAbs produced by the five stable hybridoma clones obtained were determined using an isotyping reagent kit (Sigma). To produce ascites, $5 \times 10^6$ hybridoma cells resuspended in PBS were injected i.p. into pristane-pretreated BALB/c (nu/nu) mice. Ascites fluid was collected over the next 1–2 weeks and MAbs were purified by passage over Econo-Pac DEAE Blue cartridges (BioRad, Mississauga, Ontario, Canada) according to manufacturer's instructions.

Immunoblotting and Immunoprecipitation of MRP

Membrane protein was solubilized in Laemmli buffer (Laemmli, U.K. (1970) Nature 227:680–685), and subjected to SDS-PAGE and electroblotting by standard methods. Immunoblotting was performed as described above for dot blot strips. For H69, H69AR and H69PR membrane proteins, 2.5 µg/dot were used. For C1 and T5 membrane proteins, 5 µg/dot were used. The blots were incubated with hybridoma supernatants or with an anti-P glycoprotein mAb, C219 (Centocor, Malvern, Pa.; used at 1 µg/ml). In some experiments, a polyclonal antiserum (MRP-2) that was raised against a peptide corresponding to amino acids 1418 to 1432 of MRP, and which is known to cross-react with P-gp, was used as a positive control for MRP detection.

Immunoprecipitations were carried out as follows. Cells were incubated for 24 h in L-methionine-deficient RPMI 1640 medium (Sigma) supplemented with 10% dialyzed bovine calf serum and 50 µCi/ml [$^{35}$S]methionine (1110 Ci/mmol, cell labelling grade) (Dupont NEN, Markham, Ontario, Canada). Cells were washed twice with PBS and resuspended at approximately $6 \times 10^7$ cells/ml in solubilizing buffer (1% CHAPS, 100 mM KCl, 50 mM Tris-HCl, pH 7.5) containing protease inhibitors. After 1 h on ice, insoluble matter was removed by ultracentrifugation. Aliquots of the supernatant were brought up to 250 µl with solubilizing buffer, and incubated for at least 2 h at 4° C. with hybridoma supernatant diluted 1:6. Antibody-MRP complexes were recovered by incubation with 25% w/v GammaBind Plus Protein G Sepharose (30 µl) or 10% w/v Protein A Sepharose CL-4B (25 µl) (Pharmacia, Baie D'Urfe, Quebec, Canada) in solubilization buffer for at least 2 h at 4° C. The samples were sequentially washed and precipitated proteins were eluted from the beads with Laemmli buffer and analyzed by SDS-PAGE and fluorography.

Indirect Immunofluorescence and Flow Cytometry

Cells were washed twice with cold PBS and fixed with either 0.5% paraformaldehyde (Sigma) in PBS for 30 min at 4° C. or with 70% methanol at −20° C. for 10 min. All subsequent procedures were done at 4° C. Cells were washed once with blocking solution (1% BSA/5% normal goat serum/PBS). For MAbs QCRL-2 and QCRL-3, the cells were incubated in blocking solution with 0.1% Triton X-100 for 30 min, followed by direct addition of hybridoma supernatant or ascites diluted as required. After incubation for 1 h, the cells were washed once in blocking solution with 0.1% Triton X-100 followed by a wash in blocking solution alone. The washed cells were incubated with fluorescein-conjugated goat anti-mouse IgG (H+L) F(ab')2 fragment (Pierce) diluted 1:50 in blocking solution for 30 min, and then washed twice in blocking solution with 0.1% Triton X-100. For MAb QCRL-1, cells were treated similarly except Tween-20 was used at 0.1% instead of Triton X-100, and was included in all washes and incubations. Finally, cells were resuspended in 1% paraformaldehyde in PBS and either analysed on a Coulter Epic flow cytometer or cytospins were prepared for examination by fluorescence microscopy.

RESULTS

Using spleens from mice immunized with MRP-enriched membranes, murine hybridomas were generated and screened for their ability to detect MRP in non-denatured membranes. Five stable cloned hybridoma cell lines, designated QCRL-1, QCRL-2, QCRL-3, QCRL-4, and QCRL-6, were obtained.

Figure 10:
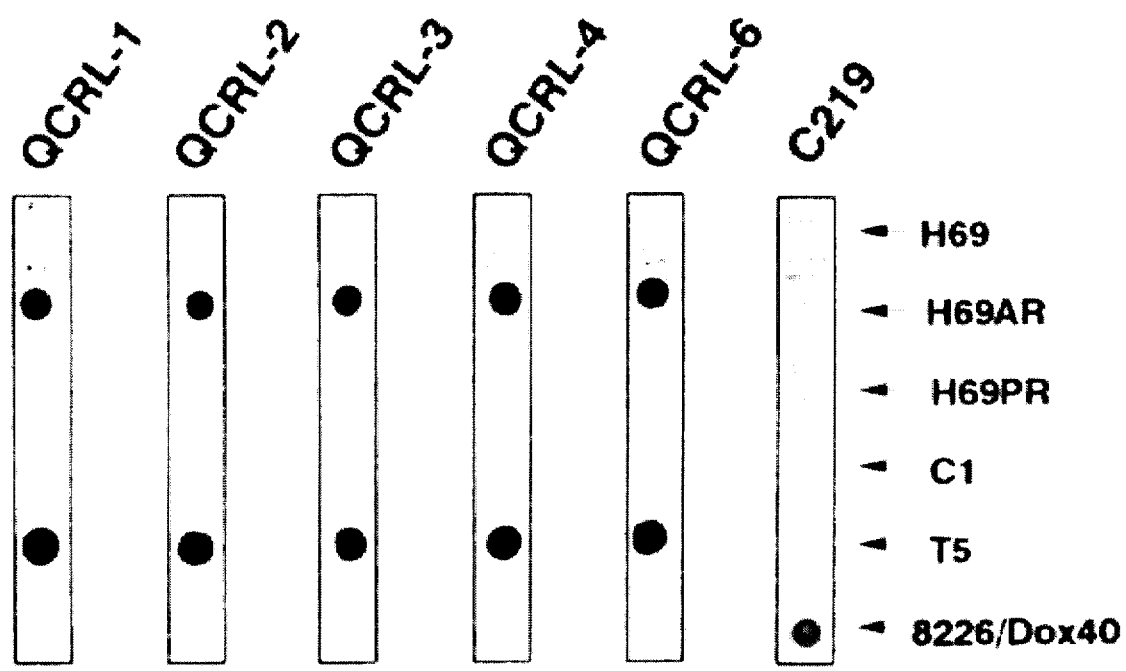
FIG. 10 is a photograph of immunodot blots of MRP-overexpressing cells (H69AR and T5), P-glycoprotein-overexpressing cells (8226/Dox40) or control cells (H69, H69PR and C1) screened with anti-MRP mAbs (QCRL-1, -2, -3, -4 or -6) or an anti-Pgp mAb (C219).

MAbs QCRL-1, QCRL-4, and QCRL-6 were determined to be of the IgG, subclass. MAb QCRL-2 was an IgG2b, and MAb QCRL-3 was an IgG2a. The MAbs reacted strongly with MRP-rich membrane fractions from both drug-selected H69AR cells and MRP-transfected T5 cells and weakly or not at all with parental H69, revertant H69PR and control C1 cell membranes (see the immunoblot analysis shown in FIG. 10). None of the MAbs cross-react with P-gp, since they showed no reactivity with membrane fractions from 8226/Dox40 cells which are known to overexpress this 170 kDa protein and which reacted with the P-gp-specific MAb C219.

To confirm the MRP-specificity of these MAbs, immunoprecipitation and immunoblot analyses were carried out. MAb QCRL-3 immunoprecipitated a single 190 kDa protein from [35S]methionine-labelled H69AR cells when protein A was used to bind immune complexes (see FIG. 11A). MAb QCRL-2 also precipitated this 190 kDa protein. This precipitated protein had the same electrophoretic mobility as the protein precipitated by the polyclonal antiserum MRP-2 which was raised against an MRP-derived peptide. To immunoprecipitate MRP with MAb QCRL-1, protein G was required to bring down immune complexes (see FIG. 11B). Protein G was also effective in precipitating MRP with MAbs QCRL-2 and QCRL-3. A 190 kDa protein was precipitated with all three MAbs from the MRP-transfected T5 cells but not from C1 control cells. Taken together, these data provide confirmation of the MRP-specificity of MAbs QCRL-1, -2 and -3.

Immunoblot analyses (Western blots) with the MAbs were carried out under both reducing and non-reducing conditions. The results for reducing conditions are shown in FIGS. 12A–C. In panels A and C, 5 μg of H69, H69AR or H69PR protein were used, 10 μg T5 or C1 protein were used, and 25 μg 8226/Dox40 protein were used. In panel B, 15 μg T5 protein were used and 75 μg of H69PR protein were used.

As shown in FIGS. 12A and B, MAb QCRL-1 detected a protein of 190 kDa. This protein is easily detectable at high levels in membranes from H69AR and T5 cells using QCRL-1 hybridoma supernatant and the relative levels in the two cell types are approximately the same as those observed using MRP-specific polyclonal antisera. The very low levels of the 190 kDa protein found in the drug-sensitive revertant H69PR cells could also be detected with a very high degree of specificity using MAb QCRL-1 ascites (see FIG. 12B). The 170 kDa P-gp, detectable in 8226/Dox40 cells with MAb C219 (see FIG. 12C), was not detected in immunoblots with MAb QCRL-1, consistent with the immunodot blot analyses.

To demonstrate that MRP-specific MAbs are able to recognize MRP epitopes in fixed cells and tissues, labelling of H69, H69AR, H69PR, C1, and T5 cells with MAbs QCRL-1, QCRL-2 and QCRL-3 was examined by flow cytometry and indirect immunofluorescence microscopy. None of the MAbs reacted with unfixed cells, suggesting that the MRP epitopes detected by these MAbs are not exposed on the cell surface. However, the epitopes recognized by these three MAbs remained intact after fixation of cells with either 0.5% paraformaldehyde or 70% methanol. MRP reactivity with MAbs QCRL-1 and QCRL-3 also remains intact after fixation with 10% formalin. Representative flow cytometry histograms obtained with MAb QCRL-3 and cells fixed with 0.5% paraformaldehyde are shown in FIGS. 13, panels A and B. MAb QCRL-3 clearly discriminated between H69AR cells, in which high levels of MRP are detected in essentially all cells, and parental H69 cells, in which the 190 kDa protein is not detected. A small difference in immunofluorescent labelling was also observed between the parental H69 cells and revertant H69PR cells, which express slightly higher levels of MRP than H69 cells. When MRP-transfected T5 cells were labelled with MAb QCRL-3, an asymmetric distribution of relative fluorescence intensity was observed. Since T5 cells are an uncloned population, individual cells within this population are likely to express different levels of MRP. Similar histograms were obtained with MAbs QCRL-1 and QCRL-2.

Using indirect immunofluorescence microscopy, all three MAbs were observed to react intensely with resistant T5 and H69AR cells but not with C1 and H69 cells. Labelling of H69AR cells was uniform while staining of T5 cells was somewhat heterogeneous, consistent with the flow cytometric analyses. Both MRP positive T5 cells and H69AR cells showed predominantly plasma membrane labelling. These data are consistent with subcellular fractionation studies which also indicate a predominantly plasma membrane localization of MRP in these cells. However, some granular cytoplasmic staining was also evident in the T5 and H69AR cells, suggesting that some MRP may be associated with intracellular membranes.

In an attempt to generate mAbs reactive against conformational epitopes of MRP, denaturing detergents were not used in the preparation of the membranes used for immunization and or in the immunodot blotting screening procedure. Only one of the five MAbs obtained, MAb QCRL-1, recognizes a linear epitope, as demonstrated by its reactivity with denatured protein in immunoblots. In contrast, the other four MAbs only detect MRP in non-denaturing immunodot blots or under relatively non-denaturing conditions in immunoprecipitations, and in fixed cells. These observations strongly suggest that these latter MAbs recognize conformation dependent epitopes. Because of its unique ability to detect MRP in immunoblots, it may be inferred that MAb QCRL-1 reacts with an MRP epitope distinct from those recognized by the other four MAbs. The ability of MAbs QCRL-2 and QCRL-3 to immunoprecipitate MRP, while MAbs QCRL-4 and QCRL-6 are unable to do so under the same conditions, suggests that these two pairs of MAbs also recognize at least two different epitopes.

EXAMPLE 9

ISOLATION OF A MOUSE MRP-ENCODING cDNA

In this Example, an MRP-encoding cDNA was isolated from a mouse cDNA library. The following methodologies were used:

Cloning and Sequence Analysis of Murine MRP

A mouse skeletal muscle 5'-stretch plus cDNA Library (Clontech Laboratories, Inc., Palo Alto, Calif.) was screened as described in Sambrook et al. (1989) *Molecular Cloning: A Laboratory Manual*, 2nd edition, Cold Spring Harbor Press, Cold Spring Harbor, N.Y., using a mouse genomic DNA fragment which was isolated previously from a 129SV-CP mouse genomic library using a human MRP cDNA as a probe. The murine genomic fragment contained an exon corresponding to exon 2 of the human MRP gene. The muscle cDNA library was also screened with a 3' proximal cDNA fragment corresponding to nucleotides 4080 to 5011 of the human MRP mRNA.

Approximately $5 \times 10^5$ plaques were screened and 4 positive cDNA clones were selected and plaque purified (clones 14B, 16, 37 and 41). The cDNA inserts of clones 14B (nucleotides 124 to 2111), 16 (nucleotides 1607 to 5888) and 41 (nucleotides 2796 to 5883) were subcloned into a pBluescript vector (Stratagene) and both strands were sequenced using the dideoxy chain termination method and Sequenase version 2.0 (U.S. Biochemicals)

Polymerase Chain Reaction (PCR) Methods

Standard PCR conditions were used to amplify regions of the isolated cDNAs for sequencing (clone 37 nucleotides 1 to 146) or for use as probes in Southern blot analysis. Reverse transcriptase (RT)-PCR using Poly A+ RNA isolated from the L138C3-109 murine mastocytoma cell line was used to confirm the sequence of some regions of the MRP mRNA.

Genomic DNA Preparation and Southern Blot Analysis

Genomic DNA was isolated from CD1 mice, digested with EcoR1 and subjected to agarose gel electrophoresis. DNA was transferred to Zetaprobe membrane (Biorad, Mississuaga, Ontario, Canada), and cross-linked using a W Stratalinker (Stratagene). The blot was prehybridized at 37° C. for 4–6 h in 50% formamide, 5×SSPE, 4×Denhardt's, 0.5% SDS and 100 µg/ml sheared and denatured herring testes DNA. It was then hybridized under the same conditions for 12–16 h with a [γ-$^{32}$P]dATP-labelled MRP cDNA fragment, and subsequently washed four times for 15 min in 2×SSC and 0.1% SDS at 42° C. In some experiments, higher stringency washes were also carried out in 2×SSC or 0.1× SSC and 0.1% SDS at 52° C.

RNA Isolation and Northern Blot Analysis

Total RNA was obtained using TRIzoL reagent (Gibco BRL, Toronto, Ontario, Canada), from various tissues dissected from sexually mature CD1 mice as well as the murine mastocytoma L138C3-109 cells and Hela cells (T5) transfected with a human MRP expression vector. PolyA enriched RNA was subsequently isolated from the total RNA using either a PoLyATtract mRNA isolation system (Promega, Madison, Wis.) or a Micro-FastTrack RNA isolation kit (Invitrogen, San Diego, Calif.). RNA was separated by electrophoresis on formaldehyde-agarose denaturing gels (Fourney, R. M. et al. (1988) *Focus* 10:5–7), blotted, prehybridized at 42° C. for 4–6 h and hybridized at 42° C. for 12–16 hours with [γ-$^{32}$P]-cDNA fragments under standard conditions (NEN Products, Boston, Mass.). The blot was washed four times with 0.1×SSC and 0.1% SDS for 15 min at 52° C. and then exposed to film. Blots were subsequently hybridized without stripping with cDNAs corresponding to glyceraldehyde-3-phosphate dehydrogenase(GAPDH) and/or β-actin. Relative levels of MRP and β-actin were determined by densitometric analysis of the autoradiographs (Molecular Dynamics, Sunnyvale, Calif.).

In Situ Hybridization

Single stranded antisense RNA probes were produced by run-off in vitro transcription in the presence of digoxygenin-UTP (Boehringer-Mannheim). The template for the MRP probe was a 1593 bp EcoRI-SacI fragment of clone 14B which corresponds to nucleotides 119 to 1610 of the murine mRNA, subcloned in pBluescript II SK+ (Stratagene). As a control, tissue sections were hybridized with an antisense probe complementary to the coding region of rabbit β-globin. Cryosections (6–8 µm) were mounted onto poly-L-lysine coated glass microscope slides, fixed for 1 h in 4% paraformaldehyde, treated with proteinase K (1 µg/µl for 10–20 min), and post-fixed in 4% paraformaldehyde for 20 min, before being hybridized overnight in 50% formamide, 5×SSC, 0.5 mg/ml tRNA, 0.005% heparin, 0.1% Tween-20 and 250 µg/ml denatured herring testes DNA. The next day the slides were washed twice in 2×SSC for 30 min each, at room temperature and once for 30 min at 65° C., followed by a 30 min high stringency wash at 65° C. in 0.1×SSC/0.1% SDS. Unhybridized probe still remaining was removed by 30 min digestion with 20 µg/ml RNase A (Pharmacia) at 37° C., followed by 15 min in 2×SSC/0.1% SDS at 65° C., and 30 min in 1×SSC/0.1% SDS at 65° C. Hybridized probe was detected with an alkaline phosphatase conjugated sheep anti-digoxigenin antibody (Boehringer-Mannheim) and the chromogenic substrates nitro blue tetrazolium and 5-bromo-4-chloro-3-indolyl-phosphate.

RESULTS

Molecular Cloning of a Mouse MRP cDNA

Preliminary Northern blotting analyses of RNA from a number of murine tissues was carried out to identify an appropriate source from which to clone the murine MRP homologue. Analyses using a human MRP cDNA probe revealed a single cross-hybridizing mRNA species of 6.0–6.4 kb that was present at relatively high levels in skeletal muscle. A mouse skeletal muscle cDNA library was then screened to isolate clones containing cDNA fragments corresponding to the cross-hybridizing murine mRNA. The first probe used for screening was a DNA fragment isolated from a 129SV-CP mouse genomic library that contained a putative exon which was 90% identical to nucleotides 48 to 226 of the coding region of human MRP mRNA. The second was a 3' proximal human cDNA fragment encompassing nucleotides 3881 to 4815 of the MRP mRNA. Sequencing of the 4 cDNA clones isolated revealed a potential open reading frame of 1528 amino acids which was 88% identical with the coding sequence of the human MRP mRNA. This open reading frame was interrupted in one clone by a stretch of 65 nucleotides bracketed by potential intron acceptor and donor sites. The region spanning the possible intron was amplified by RT-PCR using RNA from a mouse mastocytoma cell line which has been shown previously to express relatively high levels of MRP. Sequencing of the RT-PCR product confirmed that the additional sequence present in clone 14B was not present in the majority of the mRNA and most probably represents an unspliced intron. The most 5' proximal of the clones isolated, clone 37, contained a methionine codon at a position corresponding to the initiator methionine of human MRP plus 5 nucleotides of 5' untranslated sequence. In addition to an open reading frame of 1528 amino acids, the compiled sequence contained a 3' untranslated region of 1295 nucleotides. The nucleotide and encoded amino acid sequences of the isolated mouse MRP cDNA clone are shown in SEQ ID NOs: 5 and 6, respectively.

Comparison of Mouse and Human MRP Amino Acid Sequences

The deduced amino acid sequences of the murine protein and human MRP are 88% identical. The sequences of predicted Walker A and B motifs in both the NH2-and COOH-proximal nucleotide-binding folds (NBF) of the two proteins was completely conserved, as is the atypical spacing of these motifs in the NH$_2$-proximal domain. The highest variability in amino acid sequence between human MRP and the cloned murine mRNA was found to occur in the linker region which joins the two functional halves of the molecule. The most striking similarity found between murine and human MRP was the complete conservation of 114 amino acids between positions 1123 and 1236 of the murine MRP coding sequence and positions 1126 and 1139 of the human MRP coding sequence.

Analysis of the Tissue Distribution of Murine MRP mRNA

Using clone 16 as a probe, an mRNA of approximately 6–6.4 kb was detected at variable levels in all tissues examined. The highest levels of expression were in testes, lung, kidney, heart and skeletal muscle. The murine mRNA was detectable in liver only when the quantity of liver Poly A+ mRNA was increased 4-fold. This tissue profile of expression is similar to that of human MRP. The spatial pattern of expression of the cloned murine mRNA in testis and lung was also analyzed by in situ hybridization. In the testis, detection of the mRNA was restricted to germ cells. Examination of cross sections of the testis revealed that positive staining was confined to seminiferous tubules. It was also observed at low magnification that only a subset of the seminiferous tubules was stained and that staining intensity within this subset was highly variable. On the basis of their location within the seminiferous epithelium, the positively staining cells were identified as haploid spermatids. The pattern of mRNA localization observed herein indicates that expression is developmentally regulated in the testis, and that spermatogenic cells accumulate the mRNA in a stage specific fashion. The expression of the cloned murine MRP mRNA in spermatids suggests a role in the dramatic morphogenetic transformation that takes place during spermiogenesis.

In the lung high levels of the cloned murine MRP mRNA were detected in the epithelia lining both bronchi and bronchioles.

Identical results were obtained when hybridization was carried out with another of the isolated cDNAs as a probe, corresponding to a region of the transcript distinct from 14B. The specificity of the staining pattern was also assessed by hybridization with the rabbit β-globin probe. This resulted in only a low level of background staining, without any discernible pattern, in both testis and lung.

Genomic Southern Blot Analysis

To look for the existence of other genes closely related to the gene from which the murine mRNA was transcribed Southern blot analysis was performed with mouse genomic DNA. This was performed under low stringency conditions using a PCR product encompassing nucleotides 53 to 231 of the coding sequence of the murine mRNA as a probe. Since the probe did not contain any EcoR1 restriction sites and there are no EcoR1 restriction sites in the murine mRNA coding sequence, the genomic fragment(s) recognized by the probe would have been generated by cleavage within intron sequence. Conservation of restriction sites in intron sequence among closely related family members is unlikely, indicating that should a family of genes exist, the probe would have been expected to hybridize to more than one fragment under the conditions used. However, the probe hybridized to a single discrete fragment in an EcoR1 genomic digest suggesting that in contrast to the murine Pgps, the isolated murine mRNA does not belong to a multigene family.

Forming part of the present disclosure is the appended Sequence Listing for the multidrug resistance proteins of the present invention.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. An isolated nucleic acid molecule encoding a protein comprising an amino acid sequence selected from the group consisting of SEQ ID NO: 4 and SEQ ID NO: 6.

2. A recombinant expression vector suitable for transformation of a host cell comprising a nucleic acid molecule as claimed in claim 1 and at least one regulatory sequence operatively linked to the nucleic acid molecule.

3. The recombinant expression vector of claim 2, wherein the nucleic acid molecule is operatively linked to the at least one regulatory sequence to allow expression of a multidrug resistance-associated protein.

4. The recombinant expression vector of claim 2, wherein the nucleic acid molecule is operatively linked to the at least one regulatory sequence to allow expression of an RNA molecule which is antisense to the nucleic acid molecule.

5. A transformant host cell including a recombinant expression vector as claimed in claim 2.

6. A transformant host cell including a recombinant expression vector as claimed in claim 3.

7. A method for preparing an isolated multidrug resistance-associated protein comprising culturing a transformant host cell including a recombinant expression vector as claimed in claim 3 in a suitable medium until a multidrug resistance-associated protein is formed and isolating the protein.

8. A transformant host cell including a recombinant expression vector as claimed in claim 4.

9. The transformant host cell of claim 5 which is drug sensitive prior to transformation.

10. The transformant host cell of claim 5 which is a hematopoietic stem cell.

11. The transformant host cell of claim 5 which is a cardiac muscle cell.

12. An isolated nucleic acid molecule having a nucleotide sequence selected from the group consisting of SEQ ID NO: 3 and SEQ ID NO: 5.

13. An isolated nucleic acid molecule having a nucleotide sequence that is the coding region of the nucleotide sequence shown in SEQ ID NO: 3 or of the nucleotide sequence shown in SEQ ID NO: 5.

14. An isolated nucleic acid molecule which is antisense to the full length of a nucleic acid molecule encoding a protein having an amino acid sequence selected from the group consisting of SEQ ID NO: 4 and SEQ ID NO: 6.

15. An isolated nucleic acid molecule which is antisense to the full length of a nucleic acid molecule selected from the group consisting of the nucleic acid molecule shown in SEQ ID NO: 3 and the nucleic acid molecule shown in SEQ ID NO: 5.

16. A diagnostic kit for identifying multidrug resistant tumor cells comprising a nucleotide probe complementary to the full length of a nucleotide sequence selected from the group consisting of SEQ ID NO: 3 and SEQ ID NO: 5, for hybridization with mRNA from a sample of tumor cells; means for detecting the nucleotide probe bound to mRNA; means for determining the amount of mRNA in the sample; and means for comparing the amount of mRNA in the sample with a standard.

* * * * *